United States Patent
Fuerst et al.

(12) 
(10) Patent No.: US 6,291,641 B1
(45) Date of Patent: *Sep. 18, 2001

(54) HEPATITIS E VIRUS ANTIGENS AND USES THEREFOR

(75) Inventors: Thomas R. Fuerst, San Antonio, TX (US); C. Patrick McAtee, Mountain View, CA (US); Patrice O. Yarbough, Fremont, CA (US); Yi-Fan Zhang, Mountain View, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/477,292

(22) Filed: Jun. 7, 1995

Related U.S. Application Data

(60) Division of application No. 08/327,952, filed on Oct. 24, 1994, now abandoned, which is a continuation-in-part of application No. 08/240,049, filed on May 9, 1994, now Pat. No. 5,686,239, which is a continuation-in-part of application No. 07/876,941, filed on May 1, 1992, now Pat. No. 5,885, 768, and a continuation-in-part of application No. 07/870, 985, filed on Apr. 20, 1992, which is a continuation-in-part of application No. 07/822,335, filed on Jan. 7, 1992, now abandoned, which is a continuation-in-part of application No. 07/681,078, filed on Apr. 5, 1991, now abandoned, which is a continuation-in-part of application No. 07/505, 888, filed on Apr. 5, 1990, now abandoned, which is a continuation-in-part of application No. 07/420,921, filed on Oct. 13, 1989, now abandoned, which is a continuation-in-part of application No. 07/367,486, filed on Jun. 16, 1989, now abandoned, which is a continuation-in-part of application No. 07/336,672, filed on Apr. 11, 1989, now abandoned, which is a continuation-in-part of application No. 07/208, 997, filed on Jun. 17, 1988, now abandoned.

(51) Int. Cl.[7] .................................................. C07K 14/08

(52) U.S. Cl. .............................................. 530/350; 435/5

(58) Field of Search ...................... 424/189.1; 435/320.1, 435/5, 69.3; 530/806, 810, 826, 350; 536/23.72

(56) References Cited

U.S. PATENT DOCUMENTS 5,686,239 * 11/1997 Reyes et al. ............................. 435/5

FOREIGN PATENT DOCUMENTS

| WO 91/15603 | 10/1991 | (WO) . |
| WO 93/14116 | 7/1993 | (WO) . |
| WO 93/14208 | 7/1993 | (WO) . |
| WO 94/06913 | 3/1994 | (WO) . |

OTHER PUBLICATIONS

Boswell et al. "Sequence comparison and alignment: the measurement and interpretation of sequence similarity". Computational Molecular Biology. Arthur Lesk, eds. Oxford University Press, pp. 161–178, 1988.*

Bradley, D.W., et al., "Enterically transmitted non–A, non–B hepatitis: Serial passage of disease in cynomolgus macaques and tamarins and recovery of disease–associated 27– to 34–nm viruslike particles," *Proc. Natl. Acad. Sci. USA* 84(17) :6277–6281 (1987).

Dawson, G.J., et al., "Solid–phase enzyme–linked immunosorbent assay for hepatitis E virus IgG and IgM antibodies utilizing recombinant antigens and synthetic peptides," *J. Virol. Methods* 38(1) :175–186 (1992).

He, et al., "Expression and Diagnostic Utility of Hepatitis E Virus Putative Structural Proteins Expressed in Insect Cells," *J. Clin. Microbiol.* 31(8) :2167–2174 (1993).

Huang, C.–C, et al., "Molecular Cloning and Sequencing of the Mexico Isolate of Hepatitis E Virus (HEV)," *Virol.* 191(2) :550–558 (1992).

Jameel, S., "Virology (HEV) Indian HEV Strain Shows High–Level Endemicity," Dialog No. 02979317, ISSN 1074–2921. Salynn Boyles, Senior Ed., *Vaccine Weekly*, pp. 161–178.

Kaur, M., et al., "Human linear B–cell epitopes encoded by the hepatitis E virus include determinants in the RNA–dependant RNA polymerase," *Proc. Natl. Acad. Sci. USA* 89:3855–3858 (1992).

Khudyakov, Y.E., et al., "Epitope Mapping in Proteins of Hepatitis E Virus," *Virol.* 194(4) :89–96 (1993).

Lok, A.S.F., et al., "Comparison of Reactivity to ORF 2 and ORF 3 HEV Antigens in IgG and IgM Anti–HEV Assays," *Int. Symp. Virol Hepatitis and Liver Dis.*, Scientific Program and Abstract Volume, Abstract No. 694, pp. 262.

Purdy, M.A., et al., "Preliminary Evidence that a TrpE Fusion Protein Cynomolgus Macaques Against Challenge with Wild Type Hepatitis E Virus (HEV)," *J. Med. Virol.* 41:90–94.

Purdy, M.A., et al., "Expression of a hepatitis E virus (HEV)—trpE fusion protein containing epitopes recognized by antibodies in sera from human cases and experimentally infected primates," *Arch. Virol.* 123(3–4) :335–349 (1992).

Purdy, M.A., et al., "Preliminary Evidence that a trpE–HEV Fusion Protein Protects Cynomolgus Macaques Against Challenge with Wild–Type Hepatitis E Virus (HEV)," *J. Med. Virol.* 41:90–94 (1993).

(List continued on next page.)

*Primary Examiner*—Donna C. Wortman
(74) *Attorney, Agent, or Firm*—Gary Fabian; Peter J. Dehlinger; Iota Pi Law Group

(57) ABSTRACT

Antigens are provided which are derived from the enterically transmitted non-A/non-B viral hepatitis agent, known as hepatitis E virus (HEV). The HEV antigens and in particular, a soluble 62 kDa species of the capsid protein encoded by ORF2, are immunoreactive with sera from individuals infected with HEV. The 62K antigen may be produced by a baculovirus expression vector and forms virus-like particles (VLPs). The antigens are useful as diagnostic reagents in diagnostic methods and kits for determining infection of an individual with HEV. The antigens are also useful in vaccine compositions effective in methods for preventing HEV infection.

1 Claim, 16 Drawing Sheets

OTHER PUBLICATIONS

Reyes, G.R., et al., "Isolation of a cDNA from the Virus Responsible for Enterically Transmitted Non–A, Non–B Hepatitis," *Science* 247(4948):1335–1339 (1990).

Tam, A.W., et al., "Hepatitis E Virus (HEV): Molecular Cloning and Sequencing of the Full–Length Viral Genome," *Virol.* 185(1):120–131 (1991).

Tsarev, S.A., et al., "ELISA for Antibody to Hepatitis E Virus (HEV) Based on Complete Open–Reading Frame–2 Protein Expressed in Insect Cells: Identification of HEV Infection in Primates," *J. Infect. Dis.* 168(2):369–378 (1993).

Tsarev, S.A., et al., "Successful passive and active immunization of cynomolgus monkeys against hepatitis E," *Proc. Natl. Acad. Sci. USA* 91:10198–10202 (1984).

Yarbough, P.O., et al., "Hepatitis E Virus: Identification of Type–Common Epitopes," *J. Virol.* 65(11):5790–5797 (191).

Yarbough, P.O., et al., "Assay Development of Diagnostic Tests for Hepatitis E," in *Viral Hepatitis and Liver Disease* (Nishoka, K., et al., Eds.), Springer–Verlag, Tokyo, Japan, pp. 367–370 (1994).

* cited by examiner

```
           I-ORF3-->                                        I-ORF2-->
          5110v      5120v     5130v      5140v      5150v      5160v
-BURMA    TGGAATGAATAACATGTCTTTTGCTGCGCCCATGGGTTCGCGACCATGCGCCCTCGGCCT
          GAATGAATAACATGT   TTTGCTGCGCCCATGGGTTCGC ACCATGCGCCCT GGCCT
-MEXICO   CTGAATGAATAACATGTGGTTTGCTGCGCCCATGGGTTCGCCACCATGCGCCCTAGGCCT 5170v      5180v     5190v      5200v      5210v      5220v
-BURMA    ATTTTGTTGCTGCTCCTCATGTTTTTGCCTATGCTGCCCGCGCCACCGCCCGGTCAGCCG
          TTTTG TG TG TCCTC TGTTT TGCCTATG TGCCCGCGCCACCG CCGGTCAGCCG
-MEXICO   CTTTTGCTGTTGTTCCTCTTGTTTCTGCCTATGTTGCCCGCGCCACCGACCGGTCAGCCG 5230v      5240v     5250v      5260v      5270v      5280v
-BURMA    TCTGGCCGCCGTCGTGGGCGGCGCAGCGGCGGTTCCGGCGGTGGTTTCTGGGGTGACCGG
          TCTGGCCGCCGTCGTGGGCGGCGCAGCGGCGGT CCGGCGGTGGTTTCTGGGGTGACCGG
-MEXICO   TCTGGCCGCCGTCGTGGGCGGCGCAGCGGCGGTACCGGCGGTGGTTTCTGGGGTGACCGG 5290v      5300v     5310v      5320v      5330v      5340v
-BURMA    GTTGATTCTCAGCCCTTCGCAATCCCCTATATTCATCCAACCAACCCCTTCGCCCCCGAT
          GTTGATTCTCAGCCCTTCGCAATCCCCTATATTCATCCAACCAACCCCTT GCCCC GA
-MEXICO   GTTGATTCTCAGCCCTTCGCAATCCCCTATATTCATCCAACCAACCCCTTTGCCCCAGAC

I-406.4-2-->
          5350v      5360v     5370v      5380v      5390v      5400v
-BURMA    GTCACCGCTGCGGCCGGGGCTGGACCTCGTGTTCGCCAACCCGCCCGACCACTCGGCTCC
          GT  CCGCTGCG CCGGG CTGGACCTCG TTCGCCAACC GCCCG CCACT GGCTCC
-MEXICO   GTTGCCGCTGCGTCCGGGTCTGGACCTCGCCTTCGCCAACCAGCCCGGCCACTTGGCTCC 5410v      5420v     5430v      5440v      5450v      5460v
-BURMA    GCTTGGCGTGACCAGGCCCAGCGCCCCGCCGTTGCCTCACGTCGTAGACCTACCACAGCT
          CTTGGCG GA CAGGCCCAGCGCCCC CCG TGCCTC CGTCG  GACCT CCACAGC
-MEXICO   ACTTGGCGAGATCAGGCCCAGCGCCCCTCCGCTGCCTCCCGTCGCCGACCTGCCACAGCC

<--406.4-2-I
            <-ORF3--I
          5470v      5480v     5490v      5500v      5510v      5520v
-BURMA    GGGGCCGCGCCGCTAACCGCGGTCGCTCCGGCCCATGACACCCCGCCAGTGCCTGATGTC
          GGGGC GCG CGCT AC GC GT GC CC GCCCATGACACC C CC GT CC GA GT
-MEXICO   GGGGCTGCGGCGCTGACGGCTGTGGCGCCTGCCCATGACACCTCACCCGTCCCGGACGTT 5530v      5540v     5550v      5560v      5570v      5580v
-BURMA    GACTCCCGCGGCGCCATCTTGCGCCGGCAGTATAACCTATCAACATCTCCCCTTACCTCT
          GA TC CGCGG GC AT  T CGCCG CAGTATAA  T TC AC TC CCCCT AC TC
-MEXICO   GATTCTCGCGGTGCAATTCTACGCCGCCAGTATAATTTGTCTACTTCACCCCTGACATCC 5590v      5600v     5610v      5620v      5630v      5640v
-BURMA    TCCGTGGCCACCGGCACTAACCTGGTTCTTTATGCCGCCCCTCTTAGTCCGCTTTTACCC
          TC GTGGCC C GGCACTAA  T GT CT TATGC GCCCC CTTA TCCGC T T CC
-MEXICO   TCTGTGGCCTCTGGCACTAATTTAGTCCTGTATGCAGCCCCCCTTAATCCGCCTCTGCCG
```

Fig. 2A

```
              5650v      5660v      5670v      5680v      5690v      5700v
-BURMA   CTTCAGGACGGCACCAATACCCATATAATGGCCACGGAAGCTTCTAATTATGCCCAGTAC
         CT CAGGACGG AC AATAC CA AT ATGGCCAC GA GC TC AATTATGC CAGTAC
-MEXICO  CTGCAGGACGGTACTAATACTCACATTATGGCCACAGAGGCCTCCAATTATGCACAGTAC 5710v      5720v      5730v      5740v      5750v      5760v
-BURMA   CGGGTTGCCCGTGCCACAATCCGTTACCGCCCGCTGGTCCCCAATGCTGTCGGCGGTTAC
         CGGGTTGCCCG GC AC ATCCGTTACCG CC CT GT CC AATGC GT GG GG TA
-MEXICO  CGGGTTGCCCGCGCTACTATCCGTTACCGGCCCCTAGTGCCTAATGCAGTTGGAGGCTAT trpE-(C2) I->
              5770v      5780v      5790v      5800v      5810v      5820v
-BURMA   GCCATCTCCATCTCATTCTGGCCACAGACCACCACCACCCCGACGTCCGTTGATATGAAT
         GC AT TCCAT TC TTCTGGCC CA AC ACCAC ACCCC AC TC GTTGA ATGAAT
-MEXICO  GCTATATCCATTTCTTTCTGGCCTCAAACAACCACAACCCCTACATCTGTTGACATGAAT 5830v      5840v      5850v      5860v      5870v      5880v
-BURMA   TCAATAACCTCGACGGATGTTCGTATTTTAGTCCAGCCCGGCATAGCCTCTGAGCTTGTG
         TC AT AC TC AC GATGT  G ATT T GT CA CC GGCATAGC TCTGA  T GT
-MEXICO  TCCATTACTTCCACTGATGTCAGGATTCTTGTTCAACCTGGCATAGCATCTGAATTGGTC 5890v      5900v      5910v      5920v      5930v      5940v
-BURMA   ATCCCAAGTGAGCGCCTACACTATCGTAACCAAGGCTGGCGCTCCGTCGAGACCTCTGGG
         ATCCCAAG GAGCGCCT CACTA CG AA CAAGG TGGCGCTC GT GAGAC TCTGG
-MEXICO  ATCCCAAGCGAGCGCCTTCACTACCGCAATCAAGGTTGGCGCTCGGTTGAGACATCTGGT 5950v      5960v      5970v      5980v      5990v      6000v
-BURMA   GTGGCTGAGGAGGAGGCTACCTCTGGTCTTGTTATGCTTTGCATACATGGCTCACTCGTA
         GT GCTGAGGAGGA GC ACCTC GGTCTTGT ATG T TGCATACATGGCTC C  GT
-MEXICO  GTTGCTGAGGAGGAAGCCACCTCCGGTCTTGTCATGTTATGCATACATGGCTCTCCAGTT 6010v      6020v      6030v      6040v      6050v      6060v
-BURMA   AATTCCTATACTAATACACCCTATACCGGTGCCCTCGGGCTGTTGGACTTTGCCCTTGAG
         AA TCCTATAC AATAC CC TATACCGGTGCCCT GG  T TGGACTTTGCC T GAG
-MEXICO  AACTCCTATACCAATACCCCTTATACCGGTGCCCTTGGCTTACTGGACTTTGCCTTAGAG 6070v      6080v      6090v      6100v      6110v      6120v
-BURMA   CTTGAGTTTCGCAACCTTACCCCCGGTAACACCAATACGCGGGTCTCCCGTTATTCCAGC
         CTTGAGTTTCGCAA CT ACC CC GTAACACCAATAC CG GT TCCCGTTA TCCAGC
-MEXICO  CTTGAGTTTCGCAATCTCACCACCTGTAACACCAATACACGTGTGTCCCGTTACTCCAGC I-SG3-->
              6130v      6140v      6150v      6160v      6170v      6180v
-BURMA   ACTGCTCGCCACCGCCTTCGTCGCGGTGCGGACGGGACTGCCGAGCTCACCACCACGGCT
         ACTGCTCG CAC C  CG G G    GACGGGACTGC GAGCT ACCAC AC GC
-MEXICO  ACTGCTCGTCACTCCGCCCGAGGGGCC---GACGGGACTGCGGAGCTGACCACAACTGCA
```

Fig. 2B

```
         6190v      6200v      6210v      6220v      6230v      6240v
-BURMA   GCTACCCGCTTTATGAAGGACCTCTATTTTACTAGTACTAATGGTGTCGGTGAGATCGGC
         GC ACC G TT ATGAA GA CTC A TTTAC  G    TAATGG GT GGTGA  TCGGC
-MEXICO  GCCACCAGGTTCATGAAAGATCTCCACTTTACCGGCCTTAATGGGGTAGGTGAAGTCGGC 6250v      6260v      6270v      6280v      6290v      6300v
-BURMA   CGCGGGATAGCCCTCACCCTGTTCAACCTTGCTGACACTCTGCTTGGCGGCCTGCCGACA
         CGCGGGATAGC CT AC  T  T AACCTTGCTGACAC CT CT GGCGG CT CCGACA
-MEXICO  CGCGGGATAGCTCTAACATTACTTAACCTTGCTGACACGCTCCTCGGCGGGCTCCCGACA 6310v      6320v      6330v      6340v      6350v      6360v
-BURMA   GAATTGATTTCGTCGGCTGGTGGCCAGCTGTTCTACTCCCGTCCCGTTGTCTCAGCCAAT
         GAATT ATTTCGTCGGCTGG GG CA CTGTT TA TCCCG CC GTTGTCTCAGCCAAT
-MEXICO  GAATTAATTTCGTCGGCTGGCGGGCAACTGTTTTATTCCCGCCCGGTTGTCTCAGCCAAT 6370v      6380v      6390v      6400v      6410v      6420v
-BURMA   GGCGAGCCGACTGTTAAGTTGTATACATCTGTAGAGAATGCTCAGCAGGATAAGGGTATT
         GGCGAGCC AC GT AAG T TATACATC GT GAGAATGCTCAGCAGGATAAGGGT TT
-MEXICO  GGCGAGCCAACCGTGAAGCTCTATACATCAGTGGAGAATGCTCAGCAGGATAAGGGTGTT 6430v      6440v      6450v      6460v      6470v      6480v
-BURMA   GCAATCCCGCATGACATTGACCTCGGAGAATCTCGTGTGGTTATTCAGGATTATGATAAC
         GC ATCCC CA GA AT GA CT GG GA TC CGTGTGG ATTCAGGATTATGA AAC
-MEXICO  GCTATCCCCACGATATCGATCTTGGTGATTCGCGTGTGGTCATTCAGGATTATGACAAC 6490v      6500v      6510v      6520v      6530v      6540v
-BURMA   CAACATGAACAAGATCGGCCGACGCCTTCTCCAGCCCCATCGCGCCCTTTCTCTGTCCTT
         CA CATGA CA GATCGGCC AC CC TC CC GC CCATC CG CCTTT TCTGT CT
-MEXICO  CAGCATGAGCAGGATCGGCCCACCCCGTCGCCTGCGCCATCTCGGCCTTTTCTGTTCTC 6550v      6560v      6570v      6580v      6590v      6600v
-BURMA   CGAGCTAATGATGTGCTTTGGCTCTCTCTCACCGCTGCCGAGTATGACCAGTCCACTTAT
         CGAGC AATGATGT CTTTGGCT TC CTCAC GC GCCGAGTATGACCAGTCCACTTA
-MEXICO  CGAGCAAATGATGTACTTTGGCTGTCCCTCACTGCAGCCGAGTATGACCAGTCCACTTAC 6610v      6620v      6630v      6640v      6650v      6660v
-BURMA   GGCTCTTCGACTGGCCCAGTTTATGTTTCTGACTCTGTGACCTTGGTTAATGTTGCGACC
         GG TC TC ACTGGCCC GTTTAT T TC GAC   GTGAC TTGGT AATGTTGCGAC
-MEXICO  GGGTCGTCAACTGGCCCGGTTTATATCTCGGACAGCGTGACTTTGGTGAATGTTGCGACT 6670v      6680v      6690v      6700v      6710v      6720v
-BURMA   GGCGCGCAGGCCGTTGCCCGGTCGCTCGATTGGACCAAGGTCACACTTGACGGTCGCCCC
         GGCGCGCAGGCCGT GCCCG TCGCT GA TGG CCAA GTCAC CT GACGG CG CCC
-MEXICO  GGCGCGCAGGCCGTAGCCCGATCGCTTGACTGGTCCAAAGTCACCCTCGACGGGCGGCCC 6730v      6740v      6750v      6760v      6770v      6780v
-BURMA   CTCTCCACCATCCAGCAGTACTCGAAGACCTTCTTTGTCCTGCCGCTCCGCGGTAAGCTC
         CTC C AC  T  AGCA TA TC AAGAC TTCTTTGT CT CC CT CG GG AAGCTC
-MEXICO  CTCCCGACTGTTGAGCAATATTCCAAGACATTCTTTGTGCTCCCCCTTCGTGGCAAGCTC
```

Fig. 2C

```
          6790v      6800v      6810v      6820v      6830v      6840v
-BURMA  TCTTTCTGGGAGGCAGGCACAACTAAAGCCGGGTACCCTTATAATTATAACACCACTGCT
        TC TT TGGGAGGC GGCACAAC AAAGC GG TA CCTTATAATTATAA AC ACTGCT
-MEXICO TCCTTTTGGGAGGCCGGCACAACAAAAGCAGGTTATCCTTATAATTATAATACTACTGCT 6850v      6860v      6870v      6880v      6890v      6900v
-BURMA  AGCGACCAACTGCTTGTCGAGAATGCCGCCGGGCACCGGGTCGCTATTTCCACTTACACC
        AG GACCA  T CT  T GA AATGC GCCGG CA CGGGTCGC ATTTC AC TA ACC
-MEXICO AGTGACCAGATTCTGATTGAAAATGCTGCCGGCCATCGGGTCGCCATTTCAACCTATACC 6910v      6920v      6930v      6940v      6950v      6960v
-BURMA  ACTAGCCTGGGTGCTGGTCCCGTCTCCATTTCTGCGGTTGCCGTTTTAGCCCCCCACTCT
        AC AG CT GG GC GGTCC GTC CCATTTCTGCGG  GC GTTTT GC CC C CTC
-MEXICO ACCAGGCTTGGGGCCGGTCCGGTCGCCATTTCTGCGGCCGCGGTTTTGGCTCCACGCTCC

I-406.3-2-->
          6970v      6980v      6990v      7000v      7010v      7020v
-BURMA  GCGCTAGCATTGCTTGAGGATACCTTGGACTACCCTGCCCGCGCCCATACTTTTGATGAT
        GC CT GC  TGCT GAGGATAC TT GA TA CC G  CG GC CA AC TTTGATGA
-MEXICO GCCCTGGCTCTGCTGGAGGATACTTTTGATTATCCGGGGCGGGCGCACACATTTGATGAC 7030v      7040v      7050v      7060v      7070v      7080v
-BURMA  TTCTGCCCAGAGTGCCGCCCCCTTGGCCTTCAGGGCTGCGCTTTCCAGTCTACTGTCGCT
        TTCTGCCC GA TGCCGC C  T GGCCT CAGGG TG GCTTTCCAGTC ACTGTCGCT
-MEXICO TTCTGCCCTGAATGCCGCGCTTTAGGCCTCCAGGGTTGTGCTTTCCAGTCAACTGTCGCT

<--SG3-I
                                 <--406.3-2-I
          7090v      7100v      7110v      7120v      7130v      7140v
-BURMA  GAGCTTCAGCGCCTTAAGATGAAGGTGGGTAAAACTCGGGAGTTGTAGTTTATTTGCTTG
        GAGCT CAGCGCCTTAA  T AAGGTGGGTAAAACTCGGGAGTTGTAGTTTATTTG  TG
-MEXICO GAGCTCCAGCGCCTTAAAGTTAAGGTGGGTAAAACTCGGGAGTTGTAGTTTATTTGGCTG 7150v      7160v                 7170v      7180v      7190v
-BURMA  TGCCCCCCTTCTTTCTGTTGC---------TTATTTCTCATTTCTGCGTTCCGCGCTCCC
        TGCCC CCT CTT      TGC         TTATTTC  TTTCT GT CCGCGCTCCC
-MEXICO TGCCCACCTACTTATATCTGCTGATTTCCTTTATTTCCTTTTTCTCGGTCCCGCGCTCCC

<-I ORF2        <-I trpE-C2
         v 7195
-BURMA  TGA
        TGA
-MEXICO TGA
```

Fig. 2D

```
            10         20         30         40         50         60
HEV(B) MNNMSFAAPMGSRPCALGLFCCCSSCFCLCCPRHRPVSRLAAVVGGAAAVPAVVSGVTGL
       X:::  ::::::.:::::::::::::::::::::::::::::::::::::::::::::::
HEV(M) MNNMWFAAPMGSPPCALGLFCCCSSCFCLCCPRHRPVSRLAAVVGGAAAVPAVVSGVTGL
            10         20         30         40         50         60

406.4-2
            70         80         90        100        110        120
HEV(B) ILSPSQSPIFIQPTPSPPMSPLRPGLDLVFANPPDHSAPLGVTRPSAPPLPHVVDLPQLG
       ::::::::::::::: :.  ::::::::::::.:.: ::::  .:::::::.:.:::: :
HEV(M) ILSPSQSPIFIQPTPLPQTLPLRPGLDLAFANQPGHLAPLGEIRPSAPPLPPVADLPQPG
            70         80         90        100        110        120

HEV(B) PRRZ
        ::X
HEV(M) LRRZ
```

Fig. 3

```
              10         20         30         40         50         60
HEV(B)  MRPRPILLLLLMFLPMLPAPPPGQPSGRRRGRRSGGSGGGFWGDRVGDRVDSQPFAIPYIHPTN
        X:::::.::.:.:::::::::::::::::::::::.::::::::::::::::::::
HEV(M)  MRPRPLLLLFLLFLPMLPAPPTGQPSGRRRGRRSGGTGGGFWGDRVDSQPFAIPYIHPTN
              10         20         30         40         50         60

62K
              70         80         90        100        110        120
HEV(B)  PFAPDVTAAAGAGPRVRQPARPLGSAWRDQAQRPAVASRRRPTTAGAAPLTAVAPAHDTP
        :::::::.:.:..:.:::::::::::.::::::::.:::::..:::.:::::::::.
HEV(M)  PFAPDVAAASGSGPRLRQPARPLGSTWRDQAQRPSAASRRRPATAGAAALTAVAPAHDTS
              70         80         90        100        110        120

130        140        150        160        170        180
HEV(B)  PVPDVDSRGAILRRQYNLSTSPLTSSVATGTNLVLYAAPLSPLLPLQDGTNTHIMATEAS
        ::::::::::::::::::::::::::::.::::::::::.::.::::::::::::::::
HEV(M)  PVPDVDSRGAILRRQYNLSTSPLTSSVASGTNLVLYAAPLNPPLPLQDGTNTHIMATEAS
             130        140        150        160        170        180

C-2
             190        200        210        220        230        240
HEV(B)  NYAQYRVARATIRYRPLVPNAVGGYAISISFWPQTTTTPTSVDMNSITSTDVRILVQPGI
        ::::::::::::::::::::::::::::::::::::::::::::::::::::::::::::
HEV(M)  NYAQYRVARATIRYRPLVPNAVGGYAISISFWPQTTTTPTSVDMNSITSTDVRILVQPGI
             190        200        210        220        230        240

250        260        270        280        290        300
HEV(B)  ASELVIPSERLHYRNQGWRSVETSGVAEEEATSGLVMLCIHGSLVNSYTNTPYTGALGLL
        :::::::::::::::::::::::::::::::::::::::::::: :::::::::::::::
HEV(M)  ASELVIPSERLHYRNQGWRSVETSGVAEEEATSGLVMLCIHGSPVNSYTNTPYTGALGLL
             250        260        270        280        290        300

SG3
             310        320        330        340        350        360
HEV(B)  DFALELEFRNLTPGNTNTRVSRYSSTARHRLRRGADGTAELTTTAATRFMKDLYFTSTNG
        :::::::::::.: ::::::::::::::::  :::::::::::::::::::::.:: ::
HEV(M)  DFALELEFRNLTTCNTNTRVSRYSSTARHS-ARGADGTAELTTTAATRFMKDLHFTGLNG
             310        320        330        340        350

370        380        390        400        410        420
HEV(B)  VGEIGRGIALTLFNLADTLLGGLPTELISSAGGQLFYSRPVVSANGEPTVKLYTSVENAQ
        :::.::::::::::.:::::::::::::::::::::::::::::::::::::::::::::
HEV(M)  VGEVGRGIALTLLNLADTLLGGLPTELISSAGGQLFYSRPVVSANGEPTVKLYTSVENAQ
         360        370        380        390        400        410

430        440        450        460        470        480
HEV(B)  QDKGIAIPHDIDLGESRVVIQDYDNQHEQDRPTPSPAPSRPFSVLRANDVLWLSLTAAEY
        ::::.:::::::::::.:::::::::::::::::::::::::::::::::::::::::::
HEV(M)  QDKGVAIPHDIDLGDSRVVIQDYDNQHEQDRPTPSPAPSRPFSVLRANDVLWLSLTAAEY
         420        430        440        450        460        470
```

Fig. 4A

```
             490        500        510        520        530        540
HEV(B) DQSTYGSSTGPVYVSDSVTLVNVATGAQAVARSLDWTKVTLDGRPLSTIQQYSKTFFVLP
       :::::::::::::::.:::::::::::::::::::::::::::.:..:::::::::::
HEV(M) DQSTYGSSTGPVYISDSVTLVNVATGAQAVARSLDWSKVTLDGRPLPTVEQYSKTFFVLP
         480        490        500        510        520        530

550        560        570        580        590        600
HEV(B) LRGKLSFWEAGTTKAGYPYNYNTTASDQLLVENAAGHRVAISTYTTSLGAGPVSISAVAV
       :::::::::::::::::::::::::::::.::.:::::::::::::.:::::.:::.::
HEV(M) LRGKLSFWEAGTTKAGYPYNYNTTASDQILIENAAGHRVAISTYTTRLGAGPVAISAAAV
         540        550        560        570        580        590

406.3-2
             610        620        630        640        650
HEV(B) LAPHSALALLEDTLDYPARAHTFDDFCPECRPLGLQGCAFQSTVAELQRLKMVGKTR
       :::.:::::::::::.:::::.:::::::::::::::::::::::::::::.:::::
HEV(M) LAPRALALLEDTFDYPGRAHTFDDFCPECRALGLQGCAFQSTVAELQRLKVKVGKTR
         600        610        620        630        640        650

HEV(B) ELZ
       :::
HEV(M) ELZ
```

Fig. 4B

SDS-PAGE

HEPATITIS E VIRUS ANTIGENS AND USES THEREFOR

This application is a division, of application Ser. No. 08/327,952, filed Oct. 24, 1994, abandoned, herein incorpoarated by reference which is a continuation-in-part of U.S. application Ser. No. 08/240,049, filed May 9, 1994, now U.S. Pat. No. 5,686,239, which is a continuation-in-part of U.S. application Ser. No. 07/876,941, filed May 1, 1992, now U.S. Pat. No. 5,885,768, and U.S. application Ser. No. 07/870,985, filed Apr. 20, 1992, which are both continuation-in-part applications of U.S. application Ser. No. 07/822,335, filed Jan. 17, 1992, now abandoned, which is a continuation-in-part of U.S. application Ser. No. 07/681, 078, filed Apr. 5, 1991, now abandoned, which is a continuation-in-part of U.S. application Ser. No. 07/505, 888, filed Apr. 5, 1990, now abandoned, which is a continuation-in-part of U.S. application Ser. No. 07/420, 921, filed Oct. 13, 1989, now abandoned, which is a continuation-in-part of U.S. application Ser. No. 07/367, 486, filed Jun. 16, 1989, now abandoned, which is a continuation-in-part of U.S. application Ser. No. 07/336, 672, filed Apr. 11, 1989, now abandoned, which is a continuation-in-part of U.S. application Ser. No. 07/208, 997, filed Jun. 17, 1988, now abandoned, all of which except for application Ser. No. 07/681,078 are herein incorporated by reference.

FIELD OF THE INVNETION

This invention relates to antigens derived from enterically transmitted nonA/nonB hepatitis viral agent, also referred to herein as hepatitis E virus (HEV), and to diagnostic methods, diagnostic assays, vaccine compositions and vaccine methods, which employ such antigens.

REFERENCES

Arankalle, V. A., et al., The Lancet, 550 (Mar. 12, 1988).
Bradley, D., et al., J. Gen. Virol., 69:731 (1988).
Bradley, D. W., et al., Proc. Nat. Acad. Sci., USA, 84:6277 (1987).
Chauhan, et al., Lancet, 341:149 (1993).
Chomczynski, P., et al., Anal. Biochem. 162:156 (1987).
Harlow, E., et al., *Antibodies: a Laboratory Manual*, Cold Spring Harbor Laboratory Press, Cold Spring Harbor, N.Y. (1988).
Huang, C-C., et al., Virology, 1991:550 (1992).
Khuroo, M. S., Am. J. Med., 48:818 (1980).
Khuroo, M. S., et al., Am. J. Med., 70:58 (1981).
Koonin, E. V., et al., Proc. Nat. Acad. Sci. USA, 89:8259 (1992).
Lanford, R. E., et al., In Vitro Cellular and Devel Biol, 25 (2):174 (1989).
Maniatis, T., et al., *Molecular Cloning: A Laboratory Manual*, Cold Spring Harbor Laboratory (1982).
Reyes, G., et al., Science 247:1335 (1990).
Reyes, G. R., Arch. Virol. Supp. (Review) 7:15 (1993).
Rozanov, M. N., et al., J. Gen. Virol., 73:2129 (1992).
Sambrook, J., et al., *Molecular Cloning: A Laboratory Manual*, Cold Spring Harbor Laboratory. (1989).
Summers, M. D., et al., *A Manual of Methods for Baculovirus Vectors and Insect Cell Culture Procedures*, Texas Agricultural Experimental Station Bulletin No. 1555, 1988,
Tam, A., et al., Virology, 185:120 (1991-a).
Tam, A., et al., Hepatitis E virus: CDNA isolation and sequencing, p. 521–524. In Hollinger, F. B. et al. (ed.), Viral Hepatitis and Liver Disease. Williams and Wilkens, Baltimore. (1991-b).
Yarbough, P. O., In: Nishioka, K., Suzuki, H., Mishiro, S., Oda, T. eds. *Viral Hepatitis and Liver Disease*, Tokyo:Springer-Verlag. 367–370 (1994).
Yarbough, P. O., J. Virol., 65(11):5790 (1991).

BACKGROUND OF THE INVENTION

Enterically transmitted non-A/non-B hepatitis viral agent (ET-NANB; also referred to herein as HEV) is the reported cause of hepatitis in several epidemics and sporadic cases in Asia, Africa, Europe, Mexico, and the Indian subcontinent. Infection is usually by water contaminated with feces, although there is some evidence of person to person transmission. The virus does not seem to cause chronic infection. The viral etiology in ET-NANB has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of ET-NANB hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. ET-NANB is characteristically an acute infection, often associated with fever and arthralgia, and with portal inflammation and associated bile stasis in liver biopsy specimens (Arankalle, 1988). Symptoms are usually resolved within six weeks. Parenterally transmitted NANB, by contrast, produces a chronic infection in about 50% of the cases. Fever and arthralgia are rarely seen, and inflammation has a predominantly parenchymal distribution (Khuroo, 1980). The course of ET-NANBH is generally uneventful in healthy individuals, and the vast majority of those infected recover without the chronic sequelae seen with HCV. Occasionally the course of disease can be severe, however, as was recently shown by a human volunteer (Chauhan 1993). One peculiar epidemiologic feature of this disease, however, is the markedly high mortality observed in pregnant women; this is reported in numerous studies to be on the order of 10–20% (Khuroo 1981, Reyes 1993). This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. ET-NANB, but not the parenterally transmitted agent, can be transmitted to cynomolgus monkeys. The parenterally transmitted agent is more readily transmitted to chimpanzees than is ET-NANB (Bradley, 1987).

In the earlier-filed parent applications, HEV clones, peptide antigens, and the sequence of the entire HEV genome sequence were disclosed. From HEV ORF-2 expression constructs, recombinant proteins and viral particles were produced.

SUMMARY OF THE INVENTION

In one aspect the invention includes, a nucleic acid sequence encoding a 62K antigen, preferably, having an amino acid sequence selected from the group consisting of SEQ ID NO:3 and SEQ ID NO:4 and homologous sequences therewith.

In a related aspect the invention includes, an expression vector and an expression system for producing a 62K antigen. The expression vector comprises a nucleic acid sequence selected from the group consisting of SEQ ID NO:3 and SEQ ID NO:4, wherein the nucleic acid sequence is inserted into the genome of an expression vector such that the nucleic acid sequence is operationally linked to a promoter able to initiate transcription in a cell. The expression system includes a cell transfected with the above expression vector.

In another aspect the invention includes, a 62K antigen wherein the antigen consists essentially of an amino acid sequence selected from the group consisting of SEQ ID NO:15 and SEQ ID NO:16. The 62K HEV antigen may be produced by a process comprising the steps of inserting a DNA sequence encoding a capsid protein of HEV, into a baculovirus expression vector, transfecting an insect cell with the baculovirus expression vector, and culturing the insect cell under conditions sufficient to express the HEV antigen. The 62K antigen may also be produced by the process comprising the steps of, obtaining an HEV capsid derived antigen having at least 549 C-terminal amino acids of an HEV capsid protein and incubating the HEV capsid derived antigen with a baculoviral infected cell lysate under conditions sufficient to cleave the HEV capsid protein to the 62K antigen.

The invention also includes a kit and method for detecting HEV infection in a test individual. In the detecting method, an antigen of the type described is reacted with serum from the test individual, and then examined for the presence of bound antibody. The assay system includes a solid phase system, in which the antigen is carried on a solid support, or a homogeneous system, in which the antigen is associated with a reporter, where antibody binding to the antigen modulates the reporter signal when detected.

The invention further includes a vaccine composition containing in a pharmacologically acceptable carrier, a 62K antigen.

In a related aspect the invention includes a method of inhibiting infection by HEV, by administering to the subject, by parenteral injection, such as intramuscular or intravenous injection, the 62K antigen vaccine composition.

These and other objects and features of the invention will become more fully understood when the following detailed description of the invention is read in conjunction with the accompanying figures.

BRIEF DESCRIPTION OF THE DRAWINGS

FIGS. 2A–2D present the nucleotide sequences of the HEV ORF2 and ORF3 for Burma (upper line) and Mexico (lower line) strains of HEV;

FIG. 3, presents the amino acid sequences of the ORF3 protein for Burma (upper line) and Mexico (lower line) strains of HEV;

FIGS. 4A and 4B present the amino acid sequences of the ORF2 protein for the Burma (upper line) and Mexico (lower line) strains of HEV as well as the amino-terminus of each of the 62K, C-2, SG3, 406.3–2 antigens;

FIG. 6A shows PBS-soluble (S) and insoluble (I) proteins from lysate of Sf9 spinner cells infected with-recombinant baculovirus ORF2-rAcMNPV at various days post infection (DPI) which were analyzed by SDS-PAGE. The arrow points to the recombinant ORF-2 protein produced. FIG. 6B is essentially the same as that in FIG. 6A except that immunoblot, instead of Coomassie blue staining, was carried out. The arrows point to the migration of 73K and 62K proteins, respectively.

FIG. 11A has a magnification of ×95,000 and FIG. 11B ×200,000.

DETAILED DESCRIPTION OF THE INVENTION

I. Definitions

Figure 1:
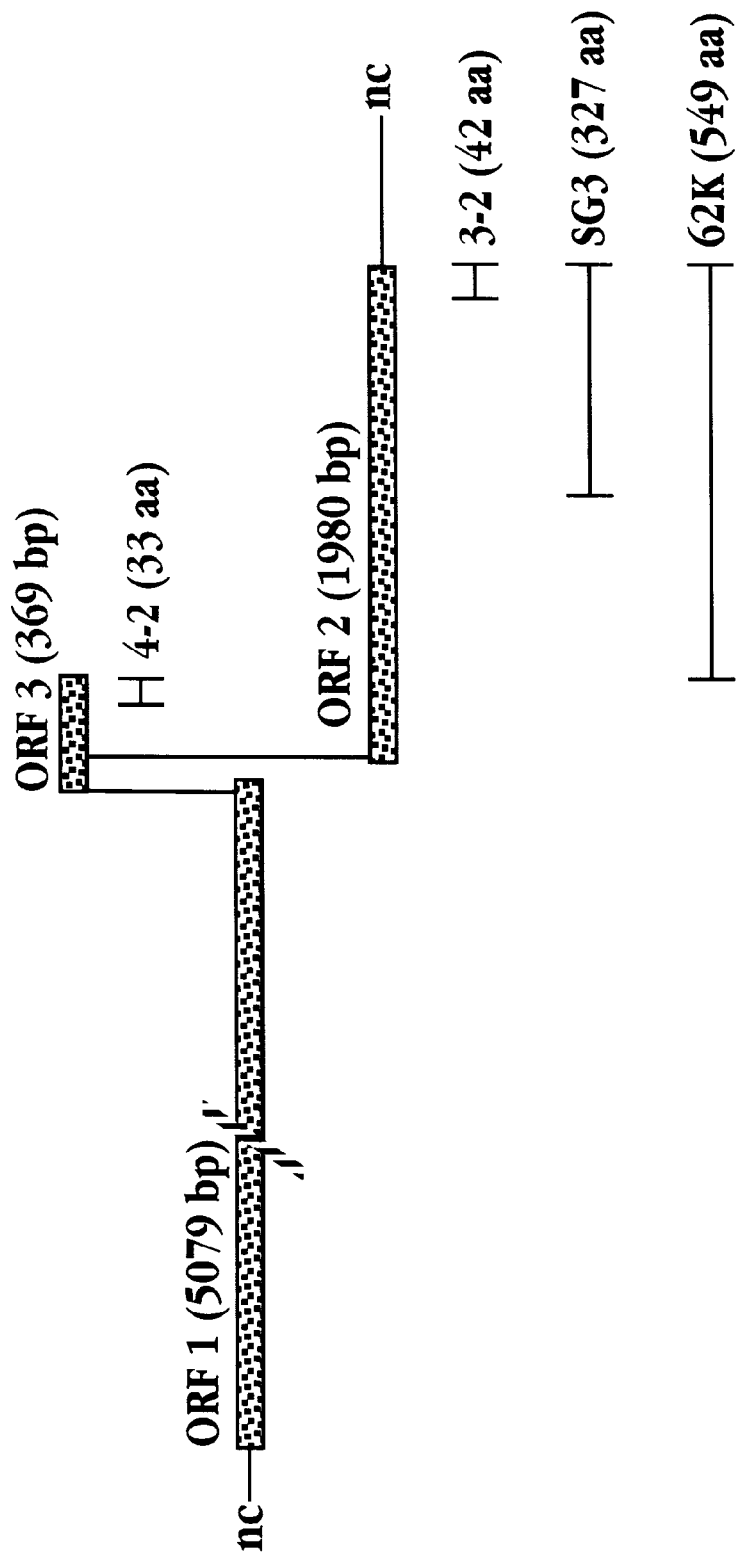
FIG. 1, presents a schematic diagram of the genomic organization of HEV, showing shows the HEV genome, the arrangement of open reading frames in the genome, and the approximate coding regions for HEV antigens 406.3-2, 406.4-2, SG3, and 62K.

The terms defined below have the following meaning herein:

1. "Enterically transmitted non-A/non-B hepatitis viral agent", "hepatitis E virus", or "HEV" means a virus, virus type, or virus class which (i) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1 (ET1.1) carried in *E. coli* strain BB4 identified by ATCC deposit number 67717.

2. Two nucleic acid fragments are "homologous" if they are capable of hybridizing to one another under hybridization conditions described by Maniatis et al., at pp. 320–323, herein incorporated by reference. However, using the following wash conditions: 2×SSC, 0.1% SDS, room temperature twice, 30 minutes each; then 2×SSC, 0.1% SDS, 50° C. once, 30 minutes; then 2×SSC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

3. Two amino acid sequences or two nucleotide sequences are considered homologous (as this term is preferably used in this specification) if they have an alignment score of >5 (in standard deviation units) using the program ALIGN with the mutation gap matrix and a gap penalty of 6 or greater. See Dayhoff, M. O., in *Atlas of Protein Sequence and Structure* (1972) Vol. 5, National Biomedical Research Foundation, pp. 101–110, and Supplement 2 to this volume, pp. 1–10, both of which are herein incorporated by reference. The two sequences (or parts thereof, preferably at least 30 amino acids in length) are more preferably homologous if their amino acids are greater than or equal to 50% identical when optimally aligned using the ALIGN program mentioned above.

4. A DNA fragment is "derived from" an HEV viral agent if it has the same or substantially the same basepair sequence as a region of the viral agent genome.

5. A protein or peptide is "derived from" an HEV viral agent if it is encoded by an open reading frame of a DNA or RNA fragment derived from an ET-NANB viral agent.

6. In two or more known peptide sequences which are more than about 70% homologous in amino acid sequence, a third amino acid sequence will be "internally consistent with the known sequences" if each amino acid in the third sequence is identical to at least one of the amino acids in the known sequences.

7. The term "antigen" refers to a molecule which is specifically recognized and bound by antibodies contained in human sera. The terms "immunogenic region" or "epitope" are used interchangeably herein to indicate that region of an antigen which is specifically recognized by an antibody in human sera.

8. The "epitope formed by" a given amino acid sequence is the epitope produced by the secondary/tertiary structure of that sequence in aqueous solution.

9. The "antigen binding site" is that region of an antibody molecule contained within the variable regions of the antibody which directly participates in binding the antigen.

10. A specified "peptide antigen containing the epitope formed by" a specified amino acid sequence includes the specified sequence itself or a portion thereof which is sufficient to define the epitope present in the specified sequence, as evidenced by immunoreactivity to an antibody contained in a human sera sample. The specified peptide antigen may include amino acid substitutions which preserve the epitope.

11. "62K antigen" is the generic term for a protein consisting essentially of the carboxyl terminal 549 amino acids encoded by ORF2 of HEV, the 549 amino acids (which have a molecular weight of 62 kDa determined by its relative rate of migration through a polyacrylamide gel). Included within the meaning of "62K antigen" are proteins which are larger than 549 amino acids so long as they contain the carboxyl terminal 549 amino acids encoded by HEV ORF2. For example, a re-engineered 62K antigen "r62K" may optionally have an N-terminal methionine; i.e., a sequence of 550 amino acids.

II. HEV Antigens

This section describes methods for preparing HEV antigens useful as diagnostic reagents and in vaccine compositions in accordance with the invention.

A. HEV Genomic Sequences

HEV genomic clones, and sequences corresponding to the entire HEV genome for different HEV strains were obtained according to published methods (Huang 1992, Yarbough 1991) and as described in the parent applications referenced above. Briefly, RNA isolated from the bile of a cynomolgus monkey having a known HEV infection was cloned, as cDNA fragments, to form a fragment library, and the library was screened by differential hybridization to radiolabeled cDNAs from infected and non-infected bile sources.

The basepair sequence of cloned regions of the HEV fragments in identified clones was determined by standard sequencing methods. With reference to FIG. 1, HEV is a virus with an approximately 7.5 kilo base (kb) single-stranded and polyadenylated RNA genome of positive-sense polarity. Three open reading frames (ORFs) have been assigned to HEV as ORF1, encoding polypeptides with domains of the RNA-directed RNA polymerase and a helicase, ORF2, encoding the putative capsid protein of the virus, and ORF3, a second putative structural protein.

The genomic organization of HEV assigns its non-structural gene(s) at the 51' terminus with the structural gene(s) at the 3' end. Two subgenomic polyadenlated transcripts of approximately 2.0 kb and 3.7 kb in sizes are detected in infected liver and co-terminated at their 3' ends with the 7.5 kb full-length genomic transcript. The genomic organization and expression strategy of HEV suggest that it might be the prototype human pathogen for a new class of RNA virus or perhaps a separate genus within the Caliciviridae family.

The genomic and peptide sequences shown in FIG. 2 correspond to the ORF-2 and ORF-3 regions of Burma (B) (upper lines) and Mexico (M) strains (lower lines) of HEV. The bases indicated in the middle lines represent conserved nucleotides. The numbering system used in the comparison is based on the Burma sequence. The region corresponding to ORF2 has SEQ ID Nos. 1 and 2 for the Burma and Mexico strains, respectively. The region corresponding to the 62 kDa antigen has SEQ ID Nos. 3 and 4 for the Burma and Mexico strains, respectively. The region corresponding to SG3 has SEQ ID Nos. 5 and 6 for the Burma and Mexican strains, respectively. The region corresponding to 406.3-2 has SEQ ID Nos. 7 and 8 for the Burma and Mexico strains, respectively. The region corresponding to ORF3 has SEQ ID Nos. 9 and 10 for the Burma and Mexico strains, respectively. The region corresponding to 406.4-2 has SEQ ID Nos. 11 and 12 for the Burma and Mexico strains, respectively.

B. HEV Antigen Sequences

The amino acid sequences corresponding to the third and second open reading frames of the Burma and Mexico strains of HEV are given in FIGS. 3 and 4, respectively. The sequence listings shown are as follows:

SEQ ID Nos. 13 and 14 correspond to the amino acid sequences for the entire putative capsid protein encoded by the Burma and Mexico strain ORF2, respectively.

SEQ ID Nos. 15 and 16 correspond to the amino acid sequences for the 62K antigens from the Burma and Mexico strain ORF2, respectively.

SEQ ID Nos. 17 and 18 correspond to the amino acid sequences for the peptides SG3 (B) and SG3 (M), respectively. Each peptide includes the carboxyl 327 amino acids of the HEV capsid.

SEQ ID Nos. 19 and 20 correspond to the amino acid sequences for the 406.4-2 (B) and 406.4-2 (M), respectively (FIG. 3). These are 33 amino acid sequences encoded by the ORF3.

SEQ ID Nos. 21 and 22 correspond to the amino acid sequences for the entire protein encoded by ORF3 of the Burma and Mexico strains, respectively.

SEQ ID Nos. 23 and 24 correspond to the amino acid sequences for the peptides 406.3-2 (B) and 406.3-2 (M), respectively. Each peptide is a 42 amino acid peptide in the C-terminal end region of capsid protein encoded by the ORF2, as indicated in the ORF2 sequence (FIG. 4).

Also contemplated are sequences which are internally consistent with the above specified sequences from different strains of HEV antigens. These include Sequence ID No. 13; Sequence ID No. 14, and internally consistent variations between Sequence ID Nos. 13 and 14; Sequence ID No. 15; Sequence ID No. 16, and internally consistent variations between Sequence ID Nos. 15 and 16; Sequence ID No. 17; Sequence ID No. 18; and internally consistent variations between Sequence ID Nos. 17 and 18; Sequence ID No. 19; Sequence ID No. 20; and internally consistent variations between Sequence ID Nos. 19 and 20; Sequence ID No. 21; Sequence ID No. 22, and internally consistent variations between Sequence ID Nos. 21 and 22; Sequence ID No. 23; Sequence ID No. 24, and internally consistent variations between Sequence ID Nos. 23 and 24.

For example, the HEV 406.4-2 antigens have the sequence homology shown below for the Burma (B) and Mexico (M) strains. The single dots in the sequence comparison indicate recognized high-probability or "neutral" amino acid substitutions. The blank spaces indicate a non-neutral substitution.

A sequence which is internally consistent with these two sequences would have one of the sequences: AN(Q/P)P(G/D)H(L/S)APLG(E/V) (I/T)RPSAPPLP(P/H) V(A/V)DLPQ (P/L)G(L/P)RR, where X/Y means either amino acid X or amino acid Y.

The ORF3 amino acid sequences, 124 amino acids in length, for the Burma and Mexican strains have an 87.1% identity in the 124 amino acids. The ORF2 amino acid sequences, having 659 amino acids of overlap, have a 93.0% identity in the 659 amino acids.

C. Preparation of HEV Antigens

To prepare the 406.3-2 (M) peptide, DNA fragments from the lambda gt11 406.3-2 described in Example 1 was subcloned into the glutathione S-transferase vector pGEX™ to express the 406.3-2(M) antigen, as detailed in Example 1, and in the Tam (1991-b) reference.

The 406.3-2(B) antigen can be prepared by PCR amplification of the Burma SEQ ID No. 5 from above by PCR amplification of the pBET1 plasmid (Tam 1991-b). This plasmid contains a 2.3 kb insert covering the ORF2 and ORF3 for Burma strain HEV sequence. The plasmid is amplified by PCR amplification, using a 5' primer containing an NcoI site and a 3' primer containing a BamHI site (Sakai). The amplified fragment is inserted into the NcoI/BamHI site of a pGEX™ vector, and expressed in an *E. coli* expression system as described in Example 1.

The SG3(B) peptide was prepared by first amplifying the SEQ ID No. 7 sequence with 5' EcoRI-NcoI and 3' BamHI linkers, using a pBET1 clone plasmid containing the entire ORF2 and ORF3 regions of HEV (B). The amplified fragment was inserted into the EcoRI/BamHI site of a Bluescript™ vector (Stratagene, La Jolla, Calif.), according to the manufacturer's instructions. After vector propagation and harvesting, the cloned insert was released by digestion with NcoI and BamHI, and gel purified. The purified fragment was inserted into the NcoI/BamHI site of a pGEX™ vector, and expressed in an *E. coli* expression system as described in Example 1. The SG3(M) peptide can be prepared similarly, using the SEQ ID No. 8 in place of the SEQ ID No. 7.

The capsid protein (B) was prepared substantially as described above by PCR amplification of the SEQ ID No. 1, from a pBET1 plasmid using a 5' primer containing an NcoI site and a 3' primer containing a BamHI site. The amplified fragment was inserted into the NcoI/BamHI site of a pGEX™ vector, and expressed in an *E. coli* expression system as described in Example 1. The capsid protein (M) is similarly prepared.

To prepare the 406.4-2(M) peptide, the lambda gt11 406.4-2 described in Example 1 was subcloned into the glutathione S-transferase vector pGEX™ to express the 406.4-2(M) antigen, as detailed in Example 1.

The 406.4-2(B) antigen can be prepared by PCR amplification of the Burma SEQ ID No. 9 from above by PCR amplification, using a 5' primer containing an NcoI site and a 3' primer containing a BamHI site. The amplified fragment is inserted into the NcoI/BamHI site of a pGEX™ vector, and expressed in an *E. coli* expression system as described in Example 1.

```
                                  10        20        30
MEXICAN (SEQ ID NO.20)   ANQPGHLAPLGEIRPSAPPLPPVADLPQPGLRR
                         ::..:.: ::::: .:::::::::.:.:::: : ::
BURMA (SEQ ID NO.19)     ANPPDHSAPLGVTRPSAPPLPHVVDLPQLGPRR
                                  10        20        30
```

D. Mature Capsid Protein

HEV peptide antigens may also be obtained from purified HEV virus propagated in primary hepatocytes obtained from primate liver, preferably from human or cynomolgus monkey liver. Methods for preparing primary primate hepatocytes for culture, and culture medium conditions effective to preserve liver-specific functions for extended periods in culture are detailed for human hepatocytes in Example 2 below.

After 3 days of growth in culture, the cells are infected with a pooled inoculum of HEV-infected cynomolgus monkey stool pool (fourth passage), as detailed in Example 3. The presence and level of propagating HEV virus in the cells can be measured by indirect immunofluorescence. Where, for example, the primary cells are cynomolgus cells, the cells can be immunoreacted with human HEV anti-sera, followed by immunoreaction with rabbit anti-human IgG antibodies.

Alternatively, the HEV virus can be detected and measured by selective amplification methods involving initial cDNA formation, and PCR amplification of HEV cDNA sequences by PCR amplification, as detailed in Example 3.

Virus particles can be isolated from HEV infected human hepatocytes in culture medium by pelleting the virus through a 30% sucrose cushion by ultracentrifugation. The pelleted virus may be further purified, if desired, by zonal centrifugation through a 10–40% sucrose gradient, combining peak virus fractions.

Other methods for separating virus particles from soluble culture-medium components may be used. For example, clarified culture medium can be passed through a size-exclusion matrix, to separate soluble components by size exclusion.

Alternatively, the clarified culture medium can be passed through an ultrafiltration membrane having a 10–20 nm pore size capable of retaining virus particles, but passing solute (non-particulate) culture medium components.

The present invention allows for glycosylation and other post-translation modifications in intact HEV capsid protein. Capsid isolation from the viral particles can be carried out by standard methods, such as ion exchange and size-exclusion chromatography, and HPLC purification, after solubilization of the virus particles in a solubilizing medium, such as a solution of a non-ionic surfactant. The protein may be purified by affinity chromatography, employing, for example, antibodies purified from anti-HEV antisera. Degradative processes may be employed to obtain partial fragments and peptides from the intact capsid protein (as well as recombinantly produced proteins); e.g. proteases may be employed. Such procedures are known to those skilled in the art.

E. Production of Capsid Antigen, Cleaved 62K Antigen, and Recombinant 62K Antigen, in Insect Cells This section describes the production of a full length ORF2 (73K), a cleaved 62K species of ORF2 (c62K), and a re-engineered 62K species of ORF2 (r62K), in insect cells.

1. Expression of ORF2 in Insect Cells.

General methods, for example, for handling and preparing baculovirus vectors and baculoviral DNA, as well as insect cell culture procedures, are outlined in A Manual of Methods for Baculovirus Vectors and Insect Cell Culture Procedures (Summers, M. D. et al., 1988), incorporated herein by reference. The recombinant baculovirus ORF2-*Autographica californica* Nuclear Polyhedrosis Virus (ORF2-rAcNPV) was constructed as described previously, He, J. et al., J. Clin. Microbiology, 31:2167 (1993), herein incorporated by reference. Recombinant baculovirus ORF2-rAcMNPV expressing HEV ORF2 protein was used to infect both *Spodoptera frugiperda*-9 (Sf9) spinner and monolayer cell cultures in accordance with the methods detailed in He (1993), and described in Example 4, below.

Infected cell lysates prepared after various times post infection were separated by centrifugation to generate both phosphate-buffered saline (PBS)-soluble and insoluble fractions. Proteins from both fractions were electrophoresed on SDS-polyacrylamide gels, which were either stained with Coomassie-blue solution (FIG. 6A) or transferred to nitrocellulose paper followed by a Western blot analysis (FIG. 6B), in accordance with Example 5.

A prominent viral protein of approximately 73 kDa in size was observed almost exclusively in PBS-insoluble fractions of spinner cells from 2–7 days post infection (FIG. 6A). Migration of this protein correlates well with predicted molecular weight of full length ORF-2. A separate Western blot confirmed that this 73K protein was reactive with ORF2 specific antiserum 1L6 that recognizes the extreme C-terminus of ORF2 (data not shown). Although degradation of host proteins is obvious at late stages of the infection (soluble fractions from days 4–7 post infection), the 73K ORF2 protein appeared to be stable throughout the infection.

When the same recombinant virus was used to infect the Sf-9 monolayer cells, a different pattern of expression was observed (FIG. 6B). Instead of observing an insoluble 73K protein species, the ORF2 protein was converted to a soluble form of approximately 62 kDa in size from day 4–7 post infection. These observations suggested that the insoluble ORF-2 (73K) protein undergoes a proteolytic cleavage to generate a soluble or cleaved 62K protein, referred to as "c62K", in the monolayer cells. Several smaller species migrating around or below 30 kDa were also observed at late stage of the infection. We suspected and confirmed later that the smaller species were degradation products of the 73K protein.

2. Proteolytic Processing of ORF2.

The conversion of the 73K protein to the soluble c62K species was observed to occur progressively during the course of infection. Thus, this conversion could be the result of autocatalytic cleavage, stimulating protease activity during the course of infection or at the time of cell harvest, or the combination of these events. To address this question, cell lysates were prepared at day 5 post infection, followed by incubation for various times before proteins in the lysates were denatured. The 73K to c62K conversion was monitored against incubation time as shown in FIG. 7. When cell lysates were denatured immediately after the cell breakage (0 min. incubation time), the ORF2 protein was present mainly as a 73K insoluble polypeptide, and very little soluble c62K protein was observed. However, when the incubation time was increased between 30 to 300 minutes, the amount of c62K proteins in the soluble fractions increased proportionally. In contrast, the amount of 73K protein in the insoluble fractions decreased, indicating an important role played by proteinase after the cell breakage. The conclusion of this experiment is that a majority of the 73K protein was cleaved to c62K by proteinase activity after cell breakage. The c62K protein observed in vivo at late infections, as shown in FIG. 6B, could be explained by the prolonged viral infection in which a significant percentage of cells were not viable, causing release of the proteinase activity.

3. Conversion of 73K to c62K may be Baculovirus Specific.

The source of the proteinase responsible for the 73K to c62K cleavage could be from Sf9 cells, baculovirus infected

Figure 8A:
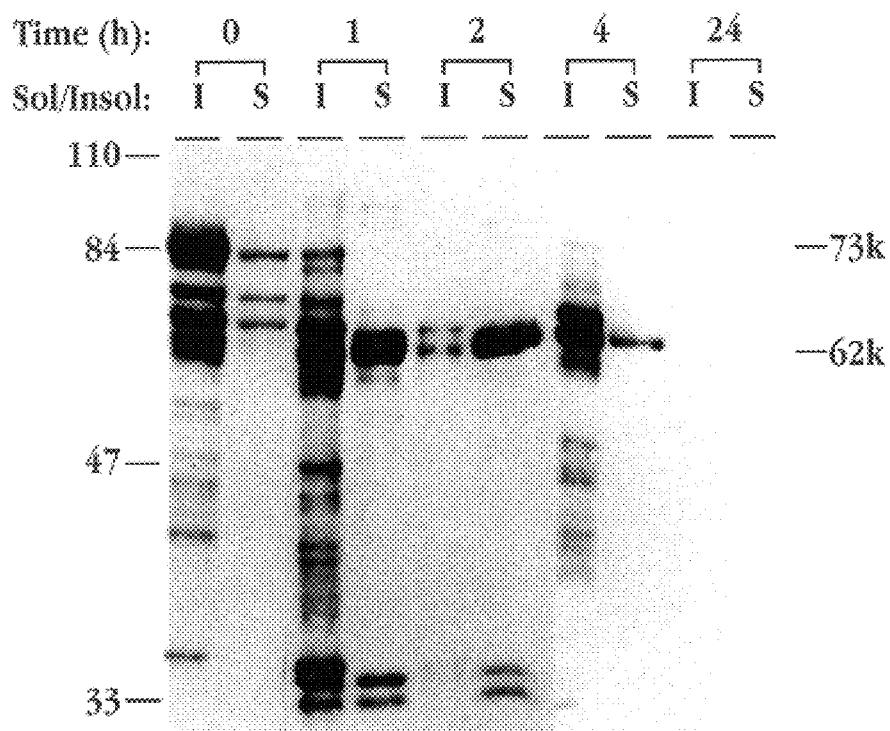
FIGS. 8A and 8B show a comparison of the cleavage of 73K to 62K between the soluble extracts of wild type baculovirus-infected (top panel) or that of uninfected (bottom panel) spinner cells. The loading of the samples in two right-most lanes of the bottom panel was reversed.
Figure 8B:
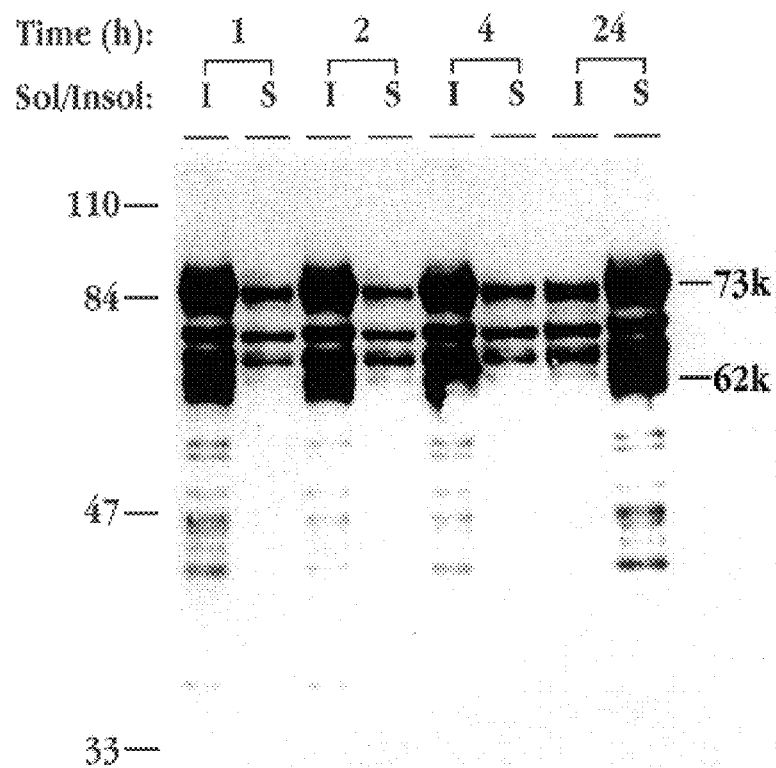

Sf9 cells, or both. To address this question, an extract mixing experiment was carried out to distinguish between these possibilities. An insoluble 73K preparation from Sf9 spinner cells was mixed with various soluble extracts and cleavage was monitored by immunoblot analysis (FIG. 8, top panel). Uninfected cell extracts, both from spinner and monolayer, had no effect on cleavage, suggesting that cleavage was mediated by viral infection. PBS did not show any effect as expected. Only when extract from an infected cell extract was used, was the cleavage of the 73K protein observed. The concurrent cleavage of the 73K and accumulation of the c62K protein was further demonstrated in a second experiment in which insoluble 73K preparation was mixed with soluble extract from spinner cells infected by wild type baculovirus (FIG. 8, bottom panel). Although cleavage could be observed 1 hr after incubation, it did not occur for as long as 24 hr when an uninfected cell extract was substituted for the infected cell extract (FIG. 8, bottom panel).

4. Purification of 73K and c62K proteins.

Figure 9:
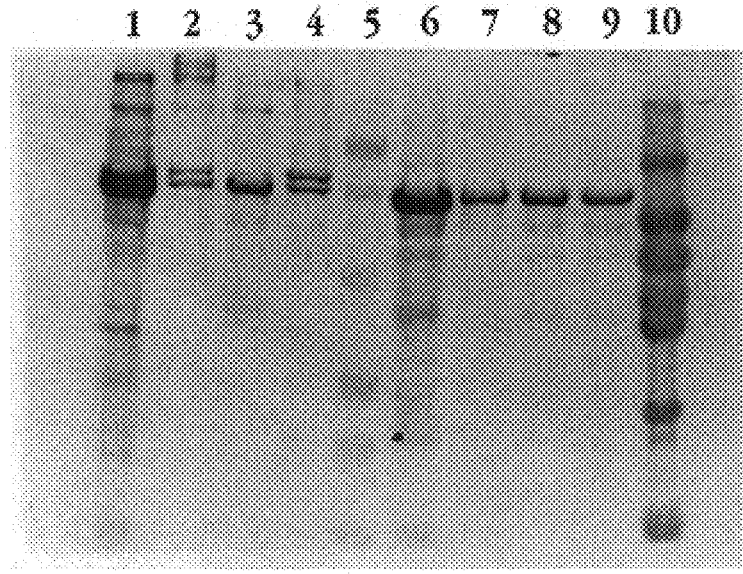
FIG. 9 shows various fractions taken during the 73K purification process and run on a 4–20% SDS PAGE and corresponding Western blot. Lane 1, Hyper-D-S Load; lane 2, pooled fractions pH 8.5; lane 3, flow through pH 7.5; lane 4 flow through pH 8.5; lane 5, BioRad MW standards; lane 6, Hyper-D-S Load; lane 7, pooled fractions pH 8.5; lane 8, flow through pH 7.5; lane 9, flow through pH 8.5; lane 10, Promega MW standards. MW standards (Promega midrange) as follows (top to bottom): phosphorylase B, 97-kDa; BSA, 66-kDa; glutamic dehydrogenase, 55-kDa; ovalbumin, 43-kDa; aldolase, 40-kDa; carbonic anhydrase, 31-kDa; soybean trypsin inhibitor, 21-kDa; lysozyme, 14-kDa. Lanes 1–5, nonreducing conditions; lanes 6–10, reduced with beta mercaptoethanol in the sample preparation buffer.

To determine whether the ORF2 proteins expressed in baculovirus infected cells were forming complex protein structures, as well as determining the cleavage site within ORF2 resulting in the formation of the c62K protein, highly purified protein preparations were prepared. The SDS-PAGE summarizing the purification of the 73K protein is shown in FIG. 9. Details of the purification process are described in Example 6a. The Hyper-D-S column load is shown in lanes 1 and 6 with subsequent flow through and eluted column fractions shown in lanes 2–4 and 7–9. In the lanes where beta mercaptoethanol was removed from the sample disruption buffer (lanes 2–4) it is clear that intrachain disulfide bonding is occurring within the 73K protein and that this association is readily eliminated under reducing conditions.

Recombinant proteins expressed at high levels in both prokaryotic and baculovirus expression systems can accumulate inside the cell in the form of inclusion bodies as was observed for the 73K protein. Under these conditions, it was necessary to develop a procedure for the extraction, solubilization, and refolding of the protein. Standard approaches were used to isolate and wash the inclusion bodies in a buffer to remove cellular contaminants followed by the solubilization of the pellets with 0.5% SDS as strong denaturant. The denaturant was then removed by rapid dilution and dialysis to allow the protein to refold to its native state. In order to avoid aggregation during the refolding process, polyethylene glycol (PEG) was added to the dilution buffer as a co-solvent which seemed to enhance the refolding of the 73K protein into a stable, soluble form.

Figure 10:
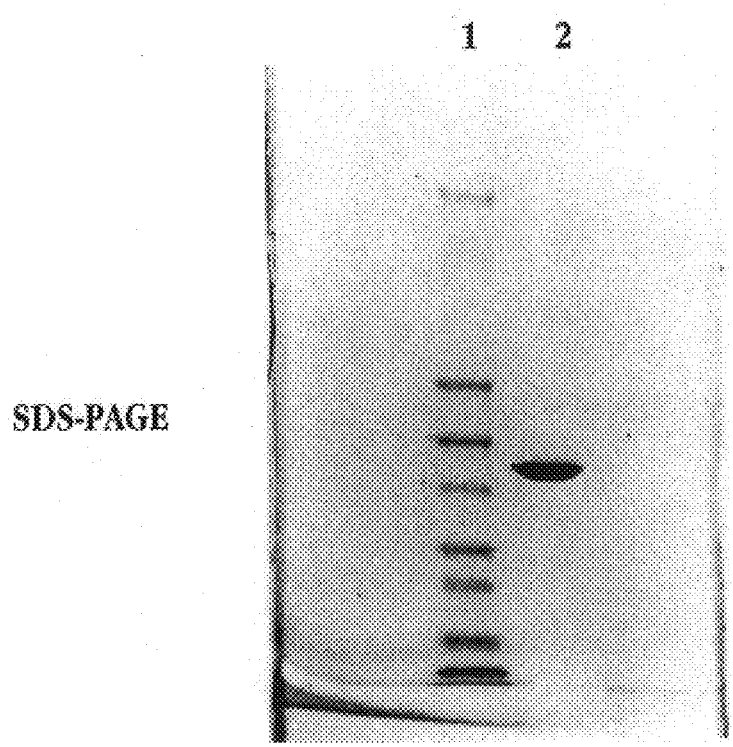
FIG. 10 shows purified soluble c62K protein run on a 4–20% SDS-PAGE. Lane 1, Novex "SeeBlue™" prestained MW standards; lane 2, final purified c62K protein. MW standards range as follows (top to bottom): myosin, 250-kDa; BSA, 98-kDa; glutamic dehydrogenase, 64-kDa; alcohol dehydrogenase, 50-kDa; carbonic anhydrase, 36-kDa; myoglobin, 30-kDa; lysozyme, 16-kDa; aprotinin, 6-kDa; insulin B chain, 4-kDa. The purification process for c62K is described in detail in Example 6B.

The final product of the c62K purification process in shown in FIG. 10. Details of the purification process are described in Example 6b. Briefly, the c62K/Sf9 cell lysate was spun out and the supernatant was then loaded onto an E. Merck DEAE EMD 650(S) column where the 62-kDa was captured and eluted at greater than 80% purity. The DEAE peak fractions were pooled and chromatographed on a Sephacryl S-100 column. Fractions containing c62K from the Sephacryl S-100 column were then purified and concentrated on a Poros HQ/F column. The protein band seen in lane 2 of FIG. 10 represents the final purified protein from the Poros HQ/F column.

A key step in the purification of the c62K protein is the addition of DTT to the lysis supernatant followed by the two-step exchange of the reducing buffer to an initially lower reducing environment (50 mM DTT to 0.5 mM DTT) to a final nonreducing environment. It is under these conditions that potential aggregation of the c62K protein to contaminating cellular proteins is eliminated. The c62K protein is then easily recovered in a highly purified, homogenous form. Based on Coomassie blue stain, we estimated the purity of both the 73K and c62K proteins to be 95 to 99 percent.

5. Evidence of VLPs-Electron Microscopy.

Figure 11A:
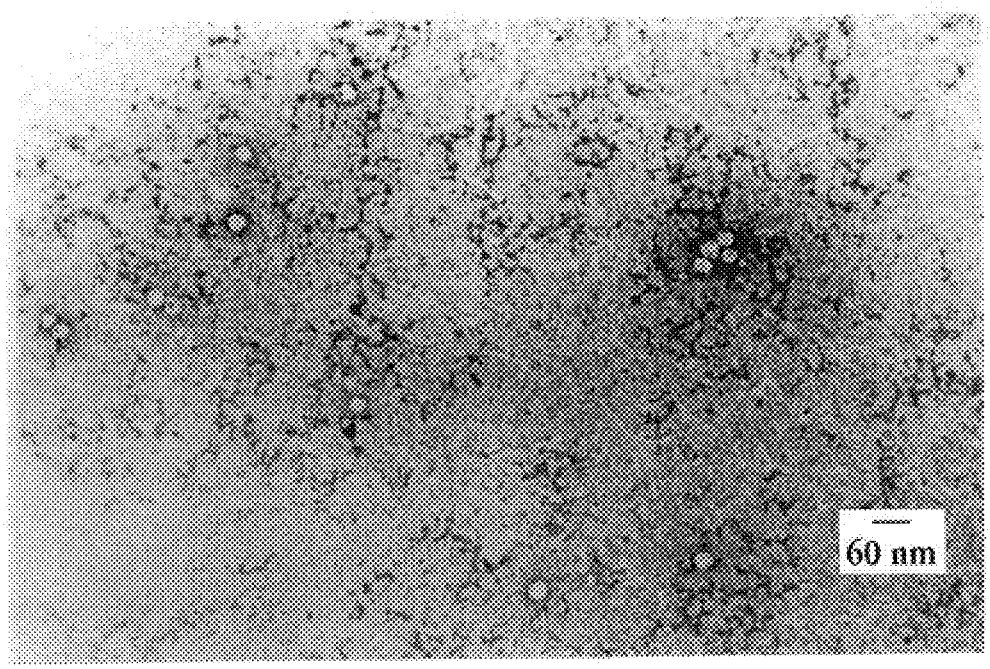
FIGS. 11A and 11B, show a comparison between electron micrographs of the purified recombinant ORF2 proteins c62K and 73K, respectively.
Figure 11B:
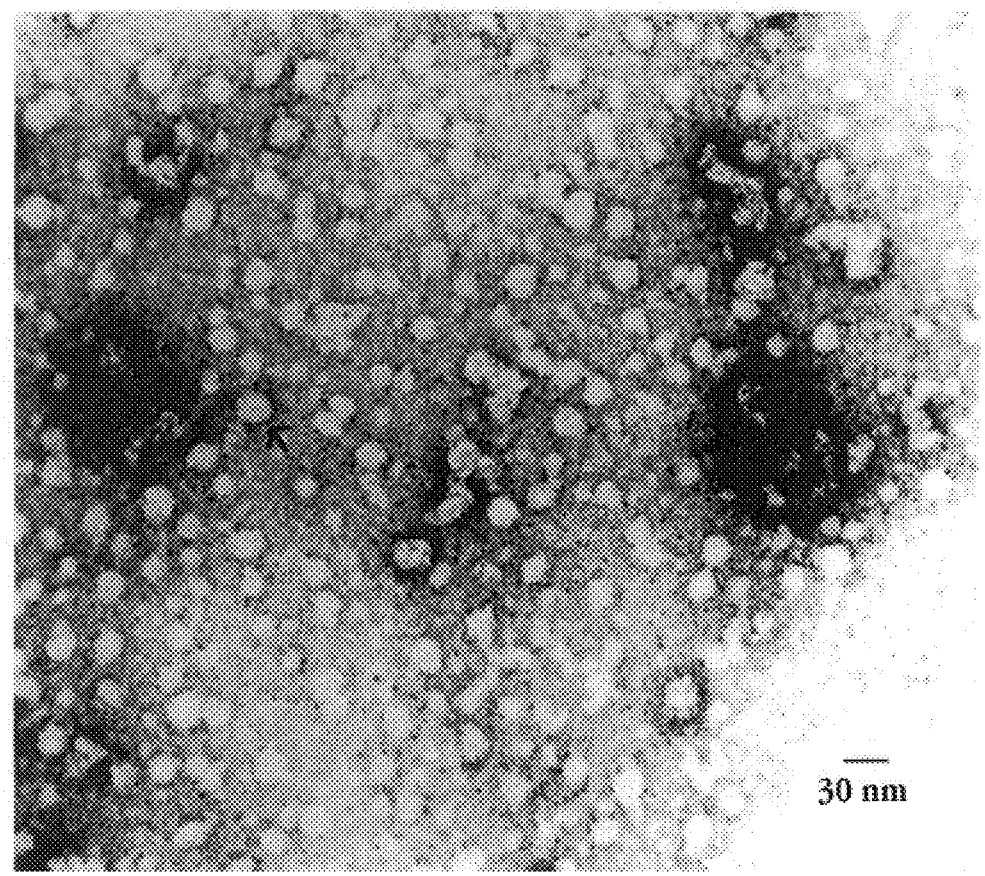
Figure 12:
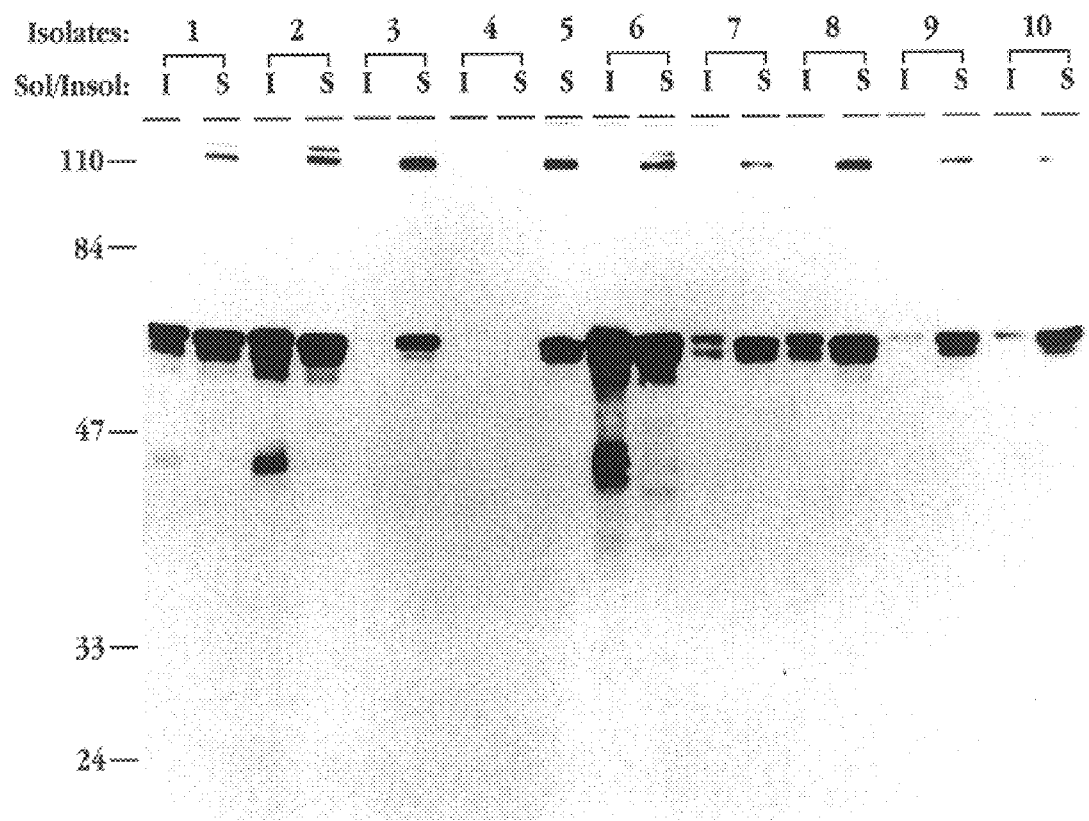
FIG. 12 shows the expression of multiple isolates of BBIII-62K in spinner cells.
Figure 13:
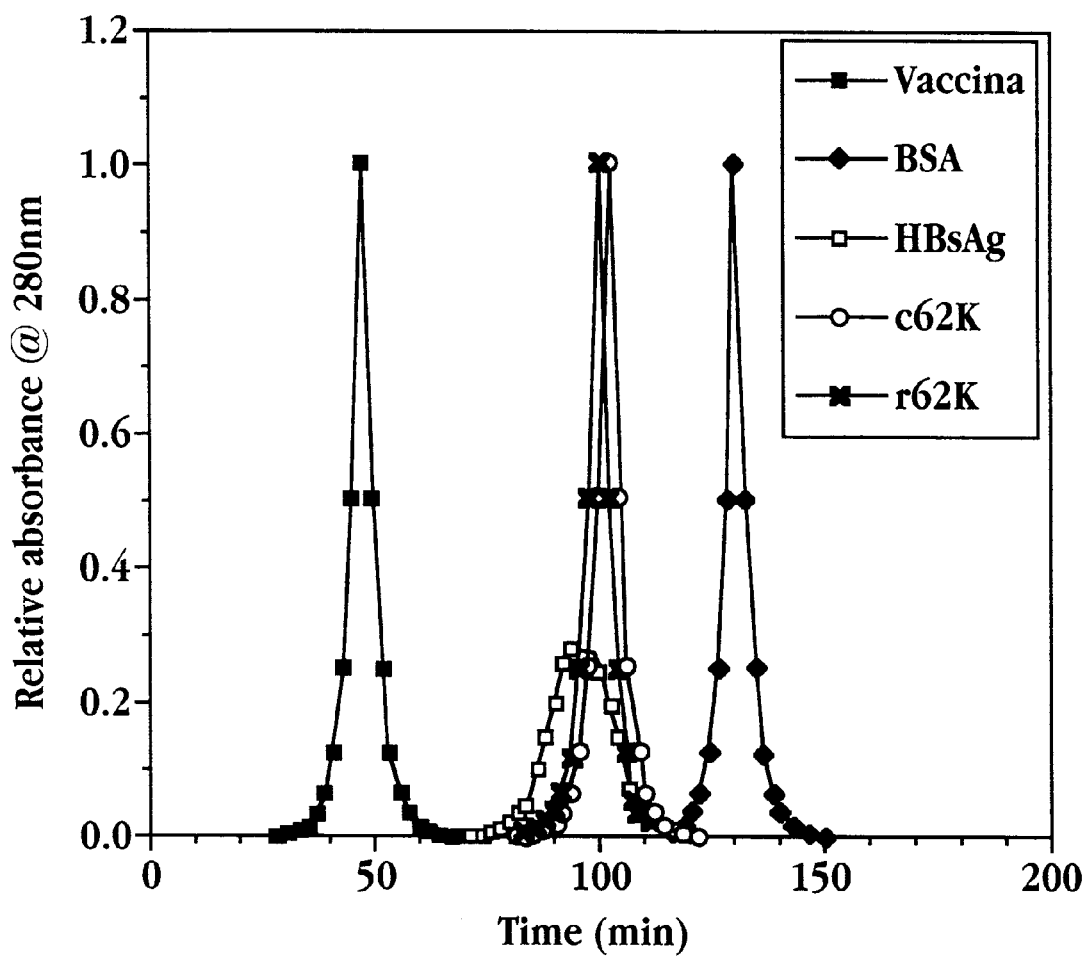
FIG. 13 shows the determination of re-engineered r62K and cleaved c62K viral particle size by Sephacryl S-1000 size exclusion chromatography. Virus particle standards (vaccinia virus and hepatitis B surface antigen, HBsAg), bovine serum albumin (BSA), and purified c62K and r62K preparations were chromatographed on a Waters AP-2 2×60 cm AP-2 column packed with Sephacryl S-1000 Superfine resin at a superficial linear velocity of 120 cm/hr. Retention times (minutes) and relative absorbance (280 nm) are indicated for the individual samples.

Purified recombinant 73K and c62K proteins were negative-stained and examined by direct electron microscopy. Electron micrographs of c62K protein revealed determinant particles (FIG. 11a) approximately 30 nm in size which agrees well with published reports describing authentic virus particles (28–34 nm) found in stool and bile (Bradley 1988, Reyes 1993). Refolded 73K protein generated a range of pleiomorphic particles 25–40 nm in size, most of which exhibit indeterminant morphology (FIG. 11b).

6. N-terminal Sequence of c62K Protein.

The virus-like particle structure displayed by the purified c62K protein, as well as its solubility, suggested that this protein may exhibit a conformational structure similar to the native virion; i.e., a viral particle or virus-like particle. However, relying on a cleavage process in which the specific mechanism is unknown is not desirable for large scale production purposes. Therefore, identification of the specific coding sequence corresponding to the c62K protein and subsequent expression in suspension cell culture may permit the ability to by-pass the cleavage process for the production of this protein. For this reason, the N-terminal sequence analysis of purified c62K protein was performed. The sequence of the first 10 amino acids sequenced was determined to be: Ala-Val-Ala-Pro-Ala-His-Asp-Thr-Pro-Pro. This sequence was perfectly homologous to amino acid residues starting at residue position 112 in ORF-2 (SEQ ID NO:13). Thus, the cleavage occurred between Thr and Ala which correspond to amino acids 111 and 112, respectively. There was no evidence that proteolytic cleavage occurred at the 3' end of ORF2 since the 62K protein reacted with antiserum 1L6 which was specifically generated to the C-terminal 42 amino acids of ORF-2 (data not shown).

Thus, a c62K protein may be produced by transfecting insect cells with a baculovirus expression vector containing a nucleic acid sequence encoding the capsid protein of HEV. More generally, it will be appreciated that only the essential portion of the ORF2 nucleotide sequence, that encoding the c62K fragment (nucleotides 112–660 represented by SEQ ID Nos. 3 and 4), and homologous sequences therewith need be expressed as a protease will cleave the excess N-terminal amino acids to the c62K protein. Other baculoviruses are known to those of skill in the art, for example, *Orygia psuedotsugata* is a commonly used vector. Baculoviruses have relatively narrow host ranges are generally confined to replication in Lepidopteran insect cells. Suitable Leptidopteran cell lines other than *Spodoptera frugiperda* are known to those of skill in the art, for example, *Lamantria dispar*, and *Helicos zea*.

It will also be appreciated by those skilled in the art that while the preferable expression system is a baculovirus expression system, the ORF2 sequence containing the coding region for the essential 549 amino acids may be expressed in other expression systems as well and may be cleaved by proteinases inherent in these systems, or they may be subsequently cleaved by a baculovirus infected cell extract in vitro. It will also be appreciated that HEV capsid proteins may be obtained from HEV propagated in human or monkey liver in vivo or in vitro as described above, and that these capsid proteins may be cleaved with baculovirus infected insect cell lysate to form the 62K antigens as well.

Additionally, the cleavage site contained in the capsid protein may be used as an artifically inserted cleavage site for use in recombinant protein products, expression systems and industrial processes for making said products. For example, it is beneficial to construct recombinant proteins such that they are generated as fusion proteins. One benefit is that the fusion partner may be used as means for purifying the recombinant protein of interest. For example, one particularly useful fusion partner is a poly histidine fragment which is efficiently purified by means of a metal chelate affinity chromatography on NTA resin, described in U.S. Pat. No. 5,310,663, herein incorporated by reference. It is useful to have a cleavage site engineered inbetween the fusion partner and the recombinant protein such that the recombinant protein may be freed from the fusion partner after purification. Thus, the discovery of a novel baculovirus specific cleavage site provides an alternative to the conventional sites currently used for recombinant proteins produced in non-baculovirus systems.

The cleavage site may be advantageous for baculovirus systems as well. For example, a fusion partner useful for directing the new polypeptide to the cytoplasm may be preferentially cleaved once in the cytoplasm.

The boundaries defining the amino acids which comprise the cleavage site may be determined by techniques known to those skilled in the art. One such technique employs the use of site directed mutagenesis to alter individual amino acids flanking the cleavage site and subsequent testing of proteinase activity on the mutant peptides.

In addition, the identity of the baculovirus specific proteinase may be determined and its nucleic acid sequence cloned and expressed by techniques known to those skilled in the art. This will enable use of the specific proteinase in a purified form rather than baculovirus infected cell lysate.

7. Recombinant Production and Purification of a Re-engineered r62K HEV Antigen.

The question remained as to whether or not a "re-engineered" 62K protein species, referred to as r62K, would result in the formation of a stable protein with similar biochemical and structural properties to the processed form of c62K. Therefore, the DNA sequence from amino acid 112 to the last amino acid of the 3' end of ORF2 was cloned into baculovirus expression vector pBluBacIII as shown in FIG. 5 and described in Example 4. A methionine codon was incorporated at 5' end to ensure proper translation initiation. After transfection and 4 rounds of plaque purifications, viral stocks and cell lysates were prepared from 10 individual plaque isolates. Western blot analysis was performed to screen for the viral isolates which produced soluble r62K protein at the highest level (FIG. 12). Nearly all the viral isolates produced soluble r62K. The solubility of r62K ranged from approximately 60–70% of total extract. One isolate was chosen for amplification for further studies.

The r62K was found to be completely soluble in the lysis buffer with quantitative recovery of the molecule in the cell lysis supernatant (data not shown). The lysis supernatant was subsequently processed through three chromatography steps to obtain purified r62K protein, according to Example 6b. The initial chromatography step was performed on an E. Merck DEAE EMD 650(S) column. It was found that the use of the EMD DEAE derivative greatly enhanced recovery of the r62K as compared to other similar weak anion exchange resins (Toyopearl 650(S), DEAE Sepharose Fast Flow, etc.). The enhanced recovery was attributed to the "tentacle arm" structure of the E. Merck derivatized resin. Further purification was conducted on a Sephacryl S-100 column which was used primarily for buffer exchange with some minor purification. The final material was obtained from peak fractions purified on a Poros HQ/F strong anion exchange resin. The final material was determined to be essentially endotoxin free by limulus amebocyte lysate assay. For purposes of Western blotting, the corresponding gel samples were diluted 1:10 prior to SDS-PAGE and transfer to PVDF membrane. The r62K band appears as a doublet which suggests the existence of a modified form of the r62K. N-terminal sequence analysis, peptide mapping, and mass spectroscopy data support the existence of a single primary amino acid sequence for the re-engineered 62K.

8. Size Determination of 62K subunit VLPs.

Gel filtration is an attractive technique for the purification and analytical characterization of viral particles as it is much less time consuming than density gradient ultracentrifugation and permits chromatographic resolution and removal of particles larger or smaller than the desired viral particle. Sephacryl S-1000 Superfine has very high porosity which makes the resin suitable for applications involving the separation of viral particles, subcellular particles, and microsomal vesicles such as Percoll. The exclusion limits of S-1000 Superfine correspond to particles approximately 300–400 nm in diameter.

The absorbance profile of the Sephacryl S-1000 Superfine chromatography of the purified c62K and r62K virus particles is shown in FIG. 13. Elution of the c62K and r62K particles corresponded to the peaks having a retention times of 95–105 minutes (data not shown). This corresponded to a particulate size of approximately 20–30 nm in diameter. The S-1000 column was also calibrated with three standards; two particulate, and one monomeric in structure. Vaccinia virus (250 nm) was found to have a retention time of approximately 48 minutes. Hepatitis B plasma derived surface antigen (HBsAg) particles (22 nm) were found to have a retention time of 95 minutes while bovine serum albumin (monomeric protein standard) had a retention time of 132 minutes.

62K antigens, consisting essentially of the C-terminal 549 amino acids encoded by HEV ORF2, and homologous sequences therewith, can similarly be prepared in other types of expression systems, preferably eucaryotic systems (e.g., mammalian and yeast), using the HEV genomic-insert plasmids above, with amplification of the desired sequences and cloning into a suitable expression vector. The coding sequences used in producing the re-engineered peptides can be derived from the cloning vectors described above and detailed elsewhere (Tam 1991-a), or from synthetic nucleotide synthesis using PCR splicing methods to join oligonucleotide fragments, according to known methods, in building up nucleotide sequences. Such modifications can be easily made by those of ordinary skill in the art.

62K antigens produced in this manner may be screened for antigenicity by the method described in Example 8. Briefly, the antigens are purified according to the method detailed in Example 6b, and plated onto wells of microtitre dishes. The polypeptides are washed with blocking solution and then reacted with sera known to contain anti-HEV antibodies. The unbound antibodies are washed away and a second antibody conjugated to a reporter molecule is then reacted with the peptide-antibody complexes. Results may be obtained, after washing away unbound second antibody, by detection of the reporter molecule.

62K antigens produced in this manner in accordance with the invention, are those that show substantially similar immunoreactivity to HEV positive sera as does a 62K antigen having the sequence of SEQ ID No.15 produced in insect cells. Immunoreactivity is substantial similar when the percentage of sera samples that are reactive with both antigens is, preferably, greater than 80%, more preferably greater than 90%, and even more preferably greater than 95%.

F. Synthetic Production of HEV Peptides

In addition to the procedures for producing the peptides described above, peptides of up to about fifty amino acids in length may be produced by conventional solid phase synthesis methods. Such methods are known to those skilled in the art. Peptides produced in this manner may be covalently linked to other peptides or protein conjugates or moieties, as would be formed, for example, recombinantly in a fusion protein.

III. Diagnostic Method

In a related aspect, the invention is directed to a method of diagnosing individuals with HEV infections wherein HEV derived peptide antigens are used to examine an individual's serum for the presence of anti-HEV antibodies.

A. Immunoreactivity of HEV Antigens

Following production of HEV antigens, in accordance with the invention, serum samples from individuals known to be infected with HEV are tested for their ability to bind to such antigens. Assays for antibody-antigen binding are well known in the art (Harlow, 1988). Solid-phase assays, such as enzyme-linked immunosorbent assay (ELISA) binding assays are particularly suitable for measuring antibody-peptide antigen binding. Such assays may be carried out in direct or competitive binding assay format. In the direct method, the test peptide is adsorbed to a solid phase. Test anti-HEV antisera is added to the peptide, and binding of human antibody to the peptide is measured, for example, as in the method of Example 8.

Alternatively, when peptides are expressed as fusion proteins of sufficient size to be retained by an SDS-PAGE, western blots may be used to determine binding of the peptide portion of the fusion protein to a serum sample.

Clones 406.3-2(M) and 406.4-2(M) were shown to encode immunoreactive peptides in co-owned U.S. patent application, Ser. No. 07/505,888, incorporated herein by reference. In continuing studies with these peptides and their analogs from the Burma strain, with HEV-positive human sera (from five different epidemics), peptide 406.3-2 (M) was immunoreactive with eight of eleven samples tested, peptide 406.4-2(M) was immunoreactive with nine of eleven samples tested, and peptides 406.3-2(B) and 406.4-2 were both immunoreactive with all six of six samples tested Yarbough 1991, herein incorporated by reference. A description of experiments leading to the above results may be found in Example 1. Peptide antigen SG3 was shown to be highly immunoreactive with infected sera in co-owned U.S. patent application, Ser. No. 08/240,049, filed May 9, 1994.

In the present invention, to evaluate the antigenicity of purified c62K protein, immunoassays were performed using a panel of human acute phase and convalescent phase sera taken during various hepatitis E epidemics. Sera were tested by ELISA for IgG and IgM antibodies to HEV according to the method of Example 8. Three antigens derived from the putative capsid protein of HEV were used: (1) SG3, 327 amino acids of ORF2 (SEQ ID NO:17) expressed in *E. coli*; (2) 73K, 660 amino acids of ORF2 (SEQ ID NO:13) expressed in baculovirus; and (3) c62K, 549 amino acids of ORF2 (SEQ ID NO:15) processed by a baculovirus proteinase(s).

Serum samples were from confirmed and suspected hepatitis E cases in endemic regions. As shown in Table 1 below, the c62K protein expressed in baculovirus detected measurable antibody to HEV in several pedigreed specimens from acute hepatitis E cases that would have gone undetected when using SG3, our best HEV antigen expressed in *E. coli* (Yarbough 1994). Specimens that tested positive to only the c62K antigen are denoted by an asterisk. For IgG anti-HEV, 3/18 serum samples (17%) scored as antibody positive uniquely with the c62K protein. For IgM anti-HEV, 7/18 serum samples (39%) scored as antibody positive uniquely with the c62K protein. In most cases, the O.D. values suggested that the anti-HEV detected by the SG3 protein or the 73K protein were just below the threshold of credible detection.

TABLE 1

COMPARATIVE ANTIGENICITY STUDIES
*E. coli* and Baculovirus Expressed Proteins

| | SG3 | c62K | 73K |
|---|---|---|---|
| ELISA FOR ANTI-HEV IgG | | | |
| Borneo S89 | 0.895 | 2.579 | 1.077 |
| FVH 3 | 0.338 | 1.298 | 0.374 |
| FVH 11 | 1.237 | 2.416 | 1.247 |
| FVH 26 | 0.397 | 1.353 | 0.571 |
| FVH 29 | 0.515 | 1.051 | 0.540 |
| FVH 31 | 0.401 | 2.474 | 0.494 |
| MB0283 | 2.602 | 2.771 | 2.558 |
| MB0288 | 2.088 | 2.506 | 2.311 |
| Som 002 | 1.357 | 2.616 | 1.301 |
| Som 010 | 2.489 | 2.617 | 2.588 |
| Som 032 | 2.456 | 2.503 | 2.351 |
| Som 055 | 1.930 | 2.386 | 1.539 |
| *Som 428 | 0.284 | 1.687 | 0.312 |
| *Som 443 | 0.246 | 0.727 | 0.337 |
| *Som 458 | 0.206 | 2.441 | 0.257 |
| Som Pool #3 | 2.305 | 2.474 | 2.235 |
| Sudan 54 | 2.159 | 2.717 | 2.310 |
| Sudan 60 | 2.264 | 2.541 | 2.402 |
| ELISA FOR ANTI-HEV ZgM | | | |
| *Boreno S89 | 0.237 | 2.527 | 0.356 |
| FVH 3 | 0.064 | 0.164 | 0.061 |
| *FVH 11 | 0.091 | 0.405 | 0.115 |
| *FVH 26 | 0.077 | 0.319 | 0.069 |
| *FVH 29 | 0.149 | 0.493 | 0.115 |
| FVH 31 | 0.080 | 0.223 | 0.061 |
| *MB0283 | 0.123 | 0.892 | 0.147 |
| *MB0288 | 0.083 | 0.335 | 0.090 |
| Som 002 | 0.508 | 2.598 | 0.681 |
| Som 010 | 0.534 | 2.526 | 0.939 |
| Som 032 | 0.722 | 2.861 | 0.877 |
| Som 055 | 1.342 | 2.560 | 1.283 |
| Som 428 | 1.165 | 2.463 | 0.863 |
| Som 443 | 0.411 | 1.106 | 0.392 |
| *Som 458 | 0.279 | 1.525 | 0.248 |
| Som Pool #3 | 0.942 | 2.397 | 1.428 |
| Sudan 54 | 0.532 | 2.652 | 0.754 |
| Sudan 60 | 0.396 | 0.529 | 0.414 |

Altogether the results demonstrated that the sensitivity and specificity of the assay was significantly improved using c62K as an antigen source. This observation suggests that structural determinants present on c62K recognized by anti-HEV antibodies engendered during a natural infection more closely resemble the native virion as opposed to the baculovirus 73K and *E. coli* expressed recombinant proteins. Taken collectively, the c62K protein is a significant advancement for detecting low levels of antibody directed to the hepatitis E virus.

B. Comparison of Immunoreactivity Between c62K and r62K

Comparative ELISA assays were performed to measure the antigenic similarities between these two proteins and further support the identity of the r62K and c62K proteins.

In accordance with the method of Example 8, equivalent amounts of c62K and r62K proteins were used to measure the antigenic similarities between these two proteins. IgG anti-HEV detection with miscellaneous serum samples showed that cleaved (c) and re-engineered (r) 62K protein species were comparable in their specificity and sensitivity to detect anti-HEV (Table 3, below).

TABLE 2

COMPARATIVE ANTIGENICITY STUDIES
Endpoint Titrations for *E. coli* and
Baculovirus Expressed Proteins ELISA FOR ANTI-HEV IgG

|  | SG3 | r62K | 73K |
|---|---|---|---|
| Cyno 9004 | 1:1000 | 1:5000 | 1:500 |
| Chimp Rusten | 1:500 | 1:5000 | 1:200 |
| K. Sa | 1:1000 | 1:5000 | 1:500 |
| A. Za | 1:200 | 1:5000 | nd |
| Mex 367 | 1:2500 | 1:10000 | 1:1000 |
| Sudan 60 | 1:1000 | 1:5000 | 1:500 |
| ABTD 80 | 1:1000 | 1:25000 | 1:200 |
| Som Pool | 1:1000 | 1:25000 | 1:200 |

ELISA FOR ANTI-HEV IgM

|  | SG3 | 62K | 73k |
|---|---|---|---|
| Cyno 9004 | nd | nd | nd |
| Chimp Rusten | nd | 1:1000 | nd |
| K. Sa | nd | 1:200 | nd |
| A. Za | 1:100 | 1:2000 | nd |
| Mex 387 | nd | 1:200 | nd |
| Sudan 60 | nd | nd | nd |
| ABTD 80 | 1:200 | 1:5000 | nd |
| Som Pool | 1:100 | 1:5000 | nd |

C. Sensitivity of the r62K Antigen

A small subset of human and non-human primate sera was diluted and assayed for anti-HEV IgG and IgM to define the sensitivity of the r62K protein (Table 2, above). Diluted sera was tested with each of the *E. coli* and baculovirus expressed antigens. The ELISA endpoint was defined as the greatest dilution of sera that still permitted a positive result in the assay. Endpoint titration data established that the r62K protein has a limit of detection for anti-HEV IgG that minimally exceeds 5-fold that of the currently used *E. coli* expressed SG3 antigen. The detection of anti-HEV IgM was consequentially increased 25-fold by using the r62K protein as the antigen of choice. The 62K protein is a significant advancement for detecting low levels of antibody directed to the hepatitis E virus.

TABLE 3

COMPARATIVE ANTIGENICITY STUDIES
Cleaved and Re-engineered Baculovirus Expressed Proteins
ELISA for anti-HEV IgG

|  | c62K | r62K | 73K |
|---|---|---|---|
| Confirmed cases in endemic regions | | | |
| ABTD 80 | 2.212 | 2.229 | 0.344 |
| ABTD 86 | 1.689 | 2.399 | 0.309 |
| MB 2/88 | 2.083 | 1.961 | 0.724 |
| Mex F387 | 2.664 | 2.635 | 1.069 |
| Som Pool | 1.679 | 2.264 | 0.342 |
| Sudan 60 | 2.493 | 2.298 | 1.024 |
| Travellers to endemic regions | | | |
| A. Za (1/100) | 1.598 | 1.887 | 0.138 |

TABLE 3-continued

COMPARATIVE ANTIGENICITY STUDIES
Cleaved and Re-engineered Baculovirus Expressed Proteins
ELISA for anti-HEV IgG

|  | c62K | r62K | 73K |
|---|---|---|---|
| A. Za (1/500) | 0.807 | 1.060 | 0.045 |
| K. Sa (1/100) | 1.983 | 1.905 | 0.800 |
| K. Sa (1/500) | 1.226 | 1.314 | 0.219 |
| B. Ka (1/100) | 0.097 | 0.080 | 0.105 |
| B. Ka (1/500) | 0.058 | 0.050 | 0.054 |
| S. Ha (1/100) | 0.116 | 0.122 | 0.122 |
| S. Ha (1/500) | 0.088 | 0.062 | 0.047 |
| Sporadic cases-acute hepatitis | | | |
| HEP 31 | 0.071 | 0.075 | 0.078 |
| HEP 35 | 0.541 | 0.542 | 0.157 |
| HEP 69 | 0.085 | 0.090 | 0.086 |
| HEP 28 | 0.087 | 0.083 | 0.090 |

IV. Antigens for HEV Assays

This section describes the peptide antigens which are employed in the assay kit and assay method described in Section V below.

A. HEV Specific Peptide Antigens

In accordance with the invention, HEV antigens, characterized as useful for diagnosis of HEV herein, include a 62K (B) or (M) antigen consisting essentially of an amino acid sequence selected from the group consisting of SEQ ID NO:15 and SEQ ID NO:16, or a homologous sequence therewith. The 62K antigen may be produced by cleavage of either native or recombinant ORF2 derived proteins with a protease, preferably a baculovirus protease. Alternatively the 62K antigen may be re-engineered and expressed in a recombinant expression system. Re-engineered 62K antigen or "r62K" preferably contains a methionine at the N-terminus and is preferably produced by a baculovirus expression vector in an insect cell.

The 62K antigens are derived from the carboxyl-terminal 549 residues of the capsid protein which is encoded by open reading frame-2. These peptide antigens can be prepared as described in Section II above and in Example 4 which follows.

Studies conducted in support of the present invention, discussed above, demonstrate that the 62K antigen is specific for HEV; i.e., 62K immunoreacts with antibodies present in the serum of HEV infected individuals. The antigen may not detect all HEV positive sera, and may pick up some false positives; i.e., non-infected individuals. The 62K antigen derived from the Mexico strain of HEV can be expected to be specifically immunoreactive with HEV positive sera.

Several peptide antigens have been previously characterized in co-owned U.S. patent applications "Enterically Transmitted Non-A/Non-B Hepatitis Viral Agent and Characteristic Epitopes Thereof", Ser. No. 07/420,921, filed Apr. 5, 1990, now abandoned, and "HEV Peptides and Methods", Ser. No. 08/240,049 both of which are incorporated herein by reference. These peptides form part of the present invention when used in assays in combination with the 62K antigens.

A first antigen in the group of previously characterized HEV peptide antigens contains the epitope formed by the 406.4-2(B) peptide (SEQ ID NO:19), or the 406.4-2(M) peptide (SEQ ID NO:20). Also contemplated are peptide antigens containing the epitope formed by an amino acid sequence homologous with or an internally consistent variation between SEQ ID Nos: 19 and 20. This first peptide antigen is derived from the carboxyl terminus of the protein encoded by open reading frame-3. A second peptide antigen contains the epitope formed by the 406.3-2(B) peptide (SEQ ID NO:23) or the 406.3-2(M) peptide (SEQ ID NO:24). Also contemplated as a second peptide antigen are peptide antigens containing the epitope formed by an amino acid sequence homologous with or an internally consistent variation between SEQ ID Nos: 11 and 12. A third peptide antigen contains the epitope formed by the SG3(B) peptide (SEQ ID NO:17) or the SG3(M) peptide (SEQ ID NO:18). Also contemplated as a third peptide antigen are peptide antigens containing the epitope formed by an amino acid sequence homologous with or an internally consistent variation between SEQ ID Nos: 17 and 18. These second and third peptide antigens are derived from the carboxyl terminus of the capsid protein encoded by open reading frame-2. FIG. 3 shows the sequence of the 406.4-2(B) and (M) peptides and FIG. 4 shows the sequence of the 406.3-2(B) and (M) and SG3(B) and SG3(M) peptides. Methods for obtaining the confirmatory peptides are described above and detailed in the following Examples.

In accordance with the present invention, reactivity of antibodies in a serum sample taken from an individual suspected of being infected with a causative agent of hepatitis to a 62K antigen is a reliable method for diagnosing the causative agent as HEV. Also forming part of the present invention, reactivity to the known peptides used in conjunction with a 62K antigen may enhance the sensitivity and reliability of the diagnostic method described below.

V. Utility

This section describes uses of the antigenic peptides and proteins of the invention as diagnostic reagents for diagnosing hepatitis E viral infection and in vaccine compositions for protecting an individual from infection with HEV.

A. Diagnostic Methods and Kits

Three basic types of diagnostic applications of the antigens will be described. The first is based on inhibition of complement-mediated, antibody-dependent cytolysis by the antigen. In this method, serum from a test individual is reacted with HEV-infected cultured human hepatocytes in the presence of complement. The presence of anti-HEV antibody is evidenced by cell lysis, as judged, for example, by trypan blue dye exclusion. Where cell lysis is observed, the specificity of the anti-HEV antibody for the HEV antigen is demonstrated by first reacting the serum with excess antigen, then mixing the serum with the cells in the presence of complement. Antibody specificity is indicated by a substantial decrease in cell lysis. The method can also be used to quantitate the antibody titre in the analyte serum, by titrating the serum with increasing amounts of antigen concentration where a noticeable effect on the extent of cell lysis is first observed.

The second general assay type is a solid-phase immunoassay. In this method, a solid phase reagent having surface-bound antigen is reacted with analyte serum, under conditions which allow antibody binding to the antigen on the reagent. After washing the reagent to remove unbound serum components, the reagent is reacted with reporter-labeled anti-human antibody to bind reporter to the reagent in proportion to the amount of bound anti-HEV antibody on the solid support. The reagent is again washed to remove unbound labeled antibody, and the amount of reporter associated with the reagent is determined. Typically, as in the system described in Example 1, the reporter is an enzyme which is detected by incubating the solid reagent in the presence of a suitable fluorometric or colorimetric substrate. However, radiolabel and other reporters may be used.

After reacting the analyte serum with the solid-phase bound antigen and washing to remove the unbound serum components, one may alternatively use the antigen itself bound to reporter as a detection reagent instead of using an anti-human antibody as a reporter mediator. The competitive assay takes advantage of antibody bivalency. The same reporters may be used in this embodiment of the solid-phase assay as was described above.

Multiple antigens may be used in conjunction or in tandem in each of the assays described above. In addition, reaction to each antigen may be distinguished. For example, in the solid-phase assay described above, two or more different antigens may be bound to solid phase in separate locations so that reaction to each antigen may be quantitated separately. Alternatively, antigens labeled with distinguishable reporters may be used to detect antigens which are interspersed on the solid support.

The solid surface reagent in the above assay is prepared by known techniques for attaching protein material to solid support material, such as polymeric beads, dip sticks, or filter material. These attachment methods generally include non-specific adsorption of the protein to the support or covalent attachment of the protein, typically through a free amine group to a chemically reactive group on the solid support, such as an activated carboxyl, hydroxyl, or aldehyde group.

The third general assay type is a homogeneous assay, in which antibody binding to a solid support produces some change in the reaction medium. Known general types of homogeneous assays proposed heretofore include: (a) spin-labeled reporters, where antibody binding to the antigen is detected by a change in reporter mobility (broadening of the spin splitting peaks); (b) fluorescent reporters, where binding is detected by a change in fluorescence efficiency; (c) enzyme reporters, where antibody binding effects enzyme/substrate interactions such as the system described in Example 4; and (d) liposome-bound reporters, where binding leads to liposome lysis and release of encapsulated reporter. The adaption of these methods to the antigens of the present invention follows conventional methods for preparation of homogeneous assay reagents.

In each of the three general assays described above, the assay method involves reacting the serum from a test individual with the antigen, and examining the antigen for the presence of bound antibody. In the first assay, the examining is done by observing the decrease in antibody-mediated cytolysis, when the antibody is bound to the antigen. In the solid-phase assay, the examining involves attaching a labeled anti-human antibody (or labeled antigen) to the antibody being examined, and measuring the amount of reporter bound to the solid support. And in the third assay type, the examining is done by observing the effect of antibody binding on a homogeneous assay reagent.

B. Vaccine Compositions and Methods

1. Preparation of Vaccine Compositions

The recombinant or cleaved 62K antigens described above are incorporated into a vaccine composition, according to known procedures, to enhance the antigenicity of the injected antigens.

In one composition, the HEV antigen is covalently coupled to a carrier protein, such as keyhole limpet hemocyanin, and injected either in solution form or in combination with an adjuvant. Alternatively, where the HEV antigen is prepared as part of a fusion protein, the non-HEV moiety of the protein may serve as the carrier protein. The derivatized or fusion protein is carried in a pharmaceutically acceptable carrier, such as in solution or in an adjuvant, such as converted alum.

Alternatively, the free antigen itself, e.g., the HEV 62K antigen, may be formulated in alum or used without adjuvant. A suitable adjuvanted vaccine has a preferred antigen concentration of about 1 mg antigen/mg alum, and not to exceed 80 mg of alum per injection.

2. Antigen Vaccine Method

In a related aspect, the invention is directed to a method of inhibiting infection of an individual by hepatitis E virus, by administering to the subject, by parenteral injection, e.g., intramuscular or intravenous injection, the vaccine composition of the invention.

Preferred vaccine compositions, for use in the method are those in which the HEV antigen includes the sequence in the peptides identified by: Sequence ID No. 15; Sequence ID No. 16, with or without an amino terminal methionine and homologous sequences therewith. The antigen vaccine composition is preferably administered intramuscularly in a series of inoculations, for example, two-three injections given at four week intervals.

The following examples, which illustrate various methods and compositions in the invention, are intended to illustrate, but not limit the scope of the invention.

Materials

Enzymes: DNAse I and alkaline phosphatase were obtained from Boehringer Mannheim Biochemicals (BMB, Indianapolis, Ind.); EcoRI, EcoRI methylase, DNA ligase, and DNA Polymerase I, from New England Biolabs (NEB, Beverly Mass.); and RNase A was obtained from Sigma (St. Louis, Mo.)

Other reagents: EcoRI linkers were obtained from NEB; and nitro blue tetrazolium (NBT), 5-bromo-4-chloro-3-indolyl phosphate (BCIP), 5-bromo-4-chloro-3-indolyl-B-D-galactopyranoside (Xgal), p-Nitrophenyl phosphate, and isopropyl B-D-thiogalactopyranoside (IPTG) were obtained from Sigma. cDNA synthesis kit and random priming labeling kits are available from Boehringer-Mannheim Biochemical (BMB, Indianapolis, Ind.).

Cloning and Expression vectors such as pBluescript™ (pBS), can be obtained from Stratagene Cloning Systems (La Jolla, Calif.), the pGEX™ expression vector can be obtained from Pharmacia (Piscataway, N.J.), and the pBluBacIII can be obtained from Invitrogen (San Diego, Calif.).

Immunodiagnostic Test Kits for Hepatitis A Virus (HAV), Hepatitis B Virus (HBV), Hepatitis C Virus (HCV), are available from Abbott Diagnostics (Abbott Park, Ill., USA). Immunodiagnostic Test Kits for Hepatitis E Virus (HEV) are available from Genelabs Diagnostics USA (Redwood City, Calif.).

EXAMPLE 1

Preparation of 406.3-2, 406.4-2, and SG3 Antigens

A. Production of Random HEV DNA Fragments.

A pBET1 plasmid is digested with EcoRI to release the insert which is purified from the linearized plasmid by gel electrophoresis. The purified fragment is suspended in a standard digest buffer (0.5M Tris HCl, pH 7.5; 1 mg/ml BSA; 10 mM MnC12) to a concentration of about 1 mg/ml and digested with DNAse I at room temperature for about 5 minutes. These reaction conditions are determined from a prior calibration study, in which the incubation time required to produce predominantly 100–300 basepair fragments is determined. The material is extracted with phenol/chloroform before ethanol precipitation.

The fragments in the digest mixture are blunt-ended and ligated with EcoRI linkers. The resultant fragments are analyzed by electrophoresis (5–10V/cm) on 1.2% agarose gel, using PhiX174/HaeIII and lambda/HindIII size markers. The 100–300 bp fraction is eluted onto NA45 strips (Schleicher and Schuell), which are then placed into 1.5 ml microtubes with eluting solution (1 M NaCl, 50 mM arginine, pH 9.0), and incubated at 67° C. for 30–60 minutes. The eluted DNA is phenol/chloroform extracted and then precipitated with two volumes of ethanol. The pellet is resuspended in 20 ml TE (0.01 M Tris HCl, pH 7.5, 0.001 M EDTA).

B. Cloning in an Expression Vector.

Lambda gt11 phage vector (Huynh) is obtained from Promega Biotec (Madison, Wis.). This cloning vector has a unique EcoRI cloning site 53 base pairs upstream from the beta-galactosidase translation termination codon. The genomic fragments from above, provided either directly from coding sequences or after amplification of cDNA, are introduced into the EcoRI site by mixing 0.5–1.0 ug EcoRI-cleaved gt11, 0.3–3 ul of the above sized fragments, 0.5 ul 10X ligation buffer (above), 0.5 ul ligase (200 units), and distilled water to 5 ul. The mixture is incubated overnight at 14° C., followed by in vitro packaging, according to standard methods (Maniatis, 1982, pp. 256–268).

The packaged phage are used to infect E. coli strain KM392, obtained from Dr. Kevin Moore, DNAX (Palo Alto, Calif.). Alternatively, E. Coli strain Y1090, available from the American Type Culture Collection (ATCC #37197), can be used. The infected bacteria are plated and the resultant colonies are checked for loss of beta-galactosidase activity-(clear plaques) in the presence of X-gal using a standard X-gal substrate plaque assay method (Maniatis). About 50% of the phage plaques will show loss of beta-galactosidase enzyme activity (recombinants).

C. Screening for HEV Recombinant Proteins.

HEV convalescent antiserum was obtained from patients infected during documented HEV outbreaks in Mexico, Borneo, Pakistan, Somalia, and Burma. The sera were immunoreactive with VLPs in stool specimens from each of several other patients with ETNANB hepatitis.

A lawn of *E. coli* KM392 cells infected with about $10^4$ pfu of the phage stock from above is prepared on a 150 mm plate and incubated, inverted, for 15–18 hours at 37° C. The lawn is overlaid with a nitrocellulose sheet, causing transfer of expressed HEV recombinant protein from the plaques to the paper. The plate and filter are indexed for matching corresponding plate and filter positions.

The filter is washed twice in TBST buffer (10 mM Tris, pH 8.0, 150 mM NaCl, 0.05% Tween 20), blocked with AIB (TBST buffer with 1% gelatin), washed again in TBST, and incubated overnight after addition of antiserum (diluted to 1:50 in AIB, 12–15 ml/plate). The sheet is washed twice in TBST and then contacted with enzyme-labeled anti-human antibody to attach the labeled antibody at filter sites containing prptides recognized by the antiserum. After a final washing, the filter is developed in a substrate medium containing 33 ml NBT (50 mg/ml stock solution maintained at 4° C.) mixed with 16 ml BCIP (50 mg/ml stock solution maintained at 4° C.) in 5 ml of alkaline phosphatase buffer (100 mM Tris, 9.5, 100 mM NaCl, 5 mM MgC12). Purple color appeared at points of peptide production, as recognized by the antiserum.

D. Screening Plating.

The areas of peptide production determined in the previous step are replated at about 100–200 pfu on an 82 mm plate. The above steps, beginning with a 15–18 hour incubation, through NBT-BCIP development, are repeated in order to plaque purify phage secreting an antigen capable of reacting with the HEV antibody. The identified plaques are picked and eluted in phage buffer (Maniatis, p. 443).

Two subclones which were selected are the 406.3-2 and 406.4-2 clones whose sequences are set forth above. These sequences were isolated from an amplified cDNA library derived from a human Mexico HEV stool specimen. Using the techniques described in this section, polypeptides expressed by these clones have been tested for immunoreactivity against a number of different human HEV-positive sera obtained from sources around the world. As shown in Table 4 below, 9 sera immunoreacted with the polypeptide expressed by the 406.4-2, and 8 sera immunoreacted with polypeptide expressed by the 406.3-2 clone.

For comparison, the Table also shows reactivity of the various human sera with the non structural peptide Y2. Only one of the sera reacted with the polypeptide expressed by this clone. No immunoreactivity was seen for normal expression products of the gt11 vector.

The amplified fragment is inserted into the EcoRI/BamHI site of a pBluescripth™ vector (Stratagene, La Jolla, Calif.), according to the manufacturer's instructions. After vector propagation and harvesting, the cloned insert is released by digestion with NcoI and BamHI, and gel purified. The purified fragment is inserted into the NcoI/BamHI site of a pGEX™ vector, and expressed in an *E. coli* expression system. Peptide expression of the SG3 peptide is similar to that described for the 406.3-2 fusion peptide.

H. Producing the Capsid Protein.

The capsid protein (B) is prepared substantially as described above by PCR amplification of the SEQ ID No. 1, from a pBET1 plasmid using a 5' primer containing an NcoI site and a 3' primer containing a BamHI site. The amplified fragment is inserted into the NcoI/BamHI site of a pGEX™ vector, and expressed in an *E. coli* expression system. The capsid protein (M) is similarly prepared.

I. Peptide Purification.

HEV peptide antigens which are soluable, such as 406.4-2 and 406.3-2, are purified by polyacrylamide gel electro-

TABLE 4

Immunoreactivity of HEV Recombinant Proteins: Human Sera

| Sera | Source | Stage | 406.4-2(M) | 406.3-2(M) | 406.4-2(B) | 406.3-2(B) | Y2 | Igt11 |
|---|---|---|---|---|---|---|---|---|
| FVH-21 | Burma | A | − | − | NT | NT | − | − |
| FVH-8 | Burma | A | + | − | NT | NT | + | − |
| B-IgG | Burma | C | + | + | + | + | NT | − |
| SOM-19 | Somalia | A | + | + | + | + | − | − |
| SOM-20 | Somalia | A | + | + | + | + | − | − |
| IM-35 | Borneo | A | + | + | NT | NT | − | − |
| IM-36 | Borneo | A | − | − | NT | NT | − | − |
| PAK-1 | Pakistan | A | + | + | NT | NT | − | − |
| FFI-4 | Mexico | A | + | + | + | + | − | − |
| FFI-125 | Mexico | A | + | + | + | + | − | − |
| F387-C | Mexico | C | + | + | + | + | NT | − |
| Normal | U.S. | | − | − | − | − | − | − |

Y2 represents an amino acid sequence encoded by a 157 basepair nucleic acid sequence from the first open reading frame of the HEV genome.
Acute-phase sera are collected between 1 and 12 days after the onset of HEV-related symptoms.
Convalescent-phase sera are collected between 30 and 90 days after the onset of jaundice.
+, reaction; −, no reaction; NT, not tested; A, acute; C, convalescent.

E. Producing the 406.3-2(M) Antigen.

The 406.3-2 gt11 plasmid from above is digested with EcoRI and the released HEV fragment is amplified by PCR in the presence of linkers which added an NcoI site at the 5' fragment end, and a BamHI site at the 3' fragment end. The amplified material is digested with NcoI and BamHI and inserted into the NcoI/BamHI site of the glutathione S-transferase vector pGEX™ expression vector, according to the manufacturer's instructions.

The pGEX™ plasmid is used to transform *E. coli* host cells, and cells which are successfully transformed with the pGEX™ vector are identified by immunofluorescence, using anti-HEV human antisera.

F. Producing the 406.4-2 Antigen.

The 406.4-2 gt11 plasmid from above is digested with EcoRI and the released HEV fragment is amplified by PCR, and the amplified fragment is inserted into the NcoI/BamHI site of the pGEX™ expression vector, as above. Peptide expression of the 406.4-2 peptide is similar to that described for the 406.3-2 fusion peptide.

G. Producing the SG3 Antigen.

The SG3 peptide is prepared by first amplifying the SEQ ID No. 7 sequence with 5' EcoRI-NcoI and 3' BamHI primer-linkers, using a gt10 phage BET1 clone plasmid containing the entire ORF2 and ORF3 regions of HEV (B).

phoresis of bacterially expressed whole cell lysates. Crude lysate preparations are loaded on 7.5% SDS-PAGE gels and run until size markers corresponding to the predicted size of each protein have nearly run off each gel. The gel running buffer is replaced with fresh buffer and the gel is allowed to continue to run for 5 minute intervals. The gel running buffer is collected after each interval and replaced with fresh buffer. The fractions are dialyzed and concentrated, and each fraction tested for immunoreactivity to a pGEX™ fusion partner, glutathione S-transferase, specific monoclonal antibody. Highly reactive fractions are pooled.

Alternatively, the peptides when expressed as GST fusions (pGEX™) are purified by column chromatography using Gluathione Sepharose, 4B (Pharmacia, Piscataway, N.J.). Briefly, non-GST fusion proteins are washed away from the column and bound protein is then eluted with 10 mM glutathione in 50mM Tris HCl pH 8.0.

Insoluble HEV peptides, such as SG3, are purified as follows. Cells induced to express the pGEX™ fusion protein are lysed with two passes through a french-press. The lysate is layered on a 40% solution of glycerol and spun at 3500 rpm in a J-20 rotor in a Beckman J221 centrifuge for 5 minutes. The pellet is resuspended in PBS then repelleted. The pellet is then resuspended in 6 M urea, 6 M guanadine in PBS pH 8.0 with homogenization for 5 minutes and repelleted. The suspension is filtered through a 0.22 um filter (Nalgene) and loaded on an IMAC column (Pharmacia) containing Fast Flow Chelating Sepharose™ (Pharmacia) loaded with 3 column volumes of a $CoCl_2$ solution according to the manufacturer's instructions. Elute the bound protein with a 2 column gradient of 6 M urea, 6 M guanadine, and between 0–1 M imidazole in PBS with a pH range of 8.0 to 6.0. Strip with 0.1 M EDTA in PBS and analyze fractions; e.g., by the ELISA protocol detailed in Example 4.

EXAMPLE 2

Human Primary Hepatocytes in Culture

A. Isolation of Hepatocytes.

Hepatocytes were isolated from human liver obtained from Stanford University Medical Center. The liver was either perfused in situ or excised as a wedge for perfusion in laboratory. The initial perfusion was performed for 10 minutes at 60 ml/min using $Ca^{++}$-, $Mg^{++}$-free Hanks' balanced salt solution supplemented with 10 mM HEPES (pH7.4) and 0.5 mM [ethylene bis(oxyethylenenitrillo]-tetraacetic acid. Perfusion was continued for additional 20 minutes using Williams' medium E (WME) supplemented with 10 mM HEPES (pH7.4) and 100 U/ml collagenase (type I, Sigma Chemical Co., St. Louis, Mo.).

After perfusion the liver capsule was removed using fine forceps, and hepatocytes were dislodged by gentle shaking in collagenase solution. The hepatocyte suspension was filtered through several layers of gauze and mixed with an equal volume of WMW containing 10% fetal bovine serum (FBS). Hepatocytes were sedimented by centrifugation at 50×X g for 5 minutes and resuspended in WME containing 5% FBS. Hepatocytes were sedimented and resuspended in the manner for 2 additional times. The final cell preparation was further filtered through several layers of gauze before examining for viability using trypan blue. The cells were plated at a density of $2 \times 10^6$ cells per 60-mm Primaria plates (Falcon) pre-coated with collagen (Collaborative Research).

Cultures were incubated at 37° C. in 5% $CO_2$ for 3 hours to allow attachment and the medium was changed to a serum-free formulation and every 48 hrs thereafter. The serum-free formulation was a WME-based medium supplemented with growth factors, hormones, 10 mM HEPES (pH7.4), 100 ug/ml gentamicin, as has been described (Lanford, 1989).

B. Detection of Liver-Specific Proteins.

Human hepatocyte cultures were maintained in serum-free medium for various periods of time and labeled with [$^{35}$S]-methionine for 24 hrs. The medium was adjusted to contain 1 mM PMSF, 1 mM EDTA, and 1% NP40. Antibodies specific for the different plasma proteins were bound to protein A-agarose beads, the beads were washed with PBS, and aliquots of the labeled medium were incubated for 16 hrs at 4° C. with the antibody-bead complexes. The beads were washed 3 times with a buffer containing 1% NP40, and immunoprecipitated proteins were eluted with gel electrophoresis sample buffer containing 2% SDS and 2% 2-mercaptoethanol. Samples were analyzed by gradient SDS-PAGE (4 to 15%) and autoradiography.

EXAMPLE 3

In Vitro HEV Infection of Primary Human Hepatocytes

A. HEV Infection of Human Hepatocytes.

The HEV-infected cynomolgus monkey #73 stool pool (fourth passage) was used as an inoculum for infections of primary human hepatocytes. Various amounts of inoculum was diluted in 1 ml of serum-free medium (SFM) and applied to the culture during a 3 hr incubation period. This solution was then supplemented with 2 ml of fresh SFM and the entire mixture was incubated overnight. The next day, cell monolayers were washed with WME (10 mM HEPES, pH7.4) for three times and changed to fresh SFM, which was changed at two day intervals thereafter.

B. Immunofluorescence Staining Assay.

Primary cynomolgus monkey hepatocytes were isolated and plated in tissue culture plates with collagen-coated coverslips as described. Cells on coverslips were infected with either the HEV-infected cynomolgus monkey #73 stool pool or the NIH normal human serum three days after initial plating. The infections were allowed to proceed for 2 weeks.

Cells on coverslips were fixed in 90% acetone at room temperature for 1 minute. The coverslips were then air-dried. The coverslips were blocked in 1% goat serum in PBS for 1 hour, washed with PBS three times, and incubated with a mixture of rabbit antisera against HEV recombinant proteins 406.3-2(B), 406.4-2(M), and 406.4-2(B) at room temperature for 3 hours. The coverslips were again washed with PBS 3 times and reacted with fluorescein isothiocyanate-conjugated (FITC) goat anti-rabbit IgG(H+L) (Zymed) diluted in PBS-1% goat serum for 30 minutes. After the coverslips were washed with PBS for 3 times and air-dried, they were mounted with FITC glycerol solution and examined under a fluorescent microscope.

C. Reverse Transcription/Polymerase Chain Reaction (RT/PCR).

HEV infection of primary cynomolgus macaque hepatocytes was evaluated by RT/PCR assays. The primers for cDNA synthesis and PCR were based on the nucleotide sequences of the full-length HEV cDNA (A. Tam et al.). Primers HEV3.2SF1 (nt 6578–6597) and HEV3.2SF2 (nt 6650–6668) are of sense polarity from the ORF2 region of the viral genome and HEV3.2SR1 (nt 7108–7127) and HEV3.2SR2 (nt 7078–7097) are antisense primers within the region.

Following extraction of total cellular RNA from HEV-infected cells using one-step guanidinium procedure or HEV-infected supernatants according to the method of Chomczynski et al. (Chomzynski, 1987), aliquots of RNA samples were heat-denatured at 95° C. for 5 minutes and subjected to reverse transcription at room temperature for 5 minutes and 42° C. for 60 minutes using 200 units per reaction of MMLV-reverse transcriptase (BRL) in a 20 ul reaction volume containing 20 units of RNasin (Promega), 1×PCR buffer (Perkin-Elmer Cetus), with a concentration of 1 mM each deoxyribonucleotide (Perkin-Elmer Cetus), and 2.5 uM of HEV3.2SR1 primer. The reaction mixture was then heat-treated at 95° C. for 5 minutes to denature the MMLV-reverse transcriptase.

Ten microliters of the cDNA synthesis product was used for PCR in a final volume of 50 ul with 0.5 uM HEV3.2SF1 primer, 1.25 units Taq DNA polymerase (AmpliTaq, Perkin-Elmer Cetus), and 1×PCR buffer, overlayed with 50 ul of mineral oil, and subjected to 40 cycles of PCR in a Perkin-Elmer thermocycler (95° C.×1 minute; 52° C.×2 minutes; 72° C. ×30 seconds). Ten microliters of the first-round PCR product then underwent another 40 cycles of nested PCR (95° C. ×1 minute; 55° C.×2 minutes; 72° C.×30 seconds) in a total volume of 50 ul containing the internal PCR primers HEV3.2SF2 and HEV3.2SR2.

First- and second-round PCR products were subjected to agarose electrophoresis, ethidium bromide stained and photographed under UV light. Southern transfer was performed and filters were hybridized with [$^{32}$P-dCTP]-labeled internal probe HEVORF2-7 exclusive of the primers (nt 6782–6997), and autoradiography performed.

EXAMPLE 4

Preparation of a 62 kDa HEV Antigen

The 62K antigens can be produced by a baculovirus expression system in insect cells as follows:

A. Insect Tissue Culture.

*Spodoptera frugiperda* (Sf9) monolayer and spinner cells are maintained at 27° C. in Grace's insect medium (Gibco/BRL, Cat No.11605-011) supplemented with 5% fetal bovine serum, 50 ug/ml gentamicin (Gibco/BRL, Cat No. 15710-015), and 0.1% Pluronic F-68 (Gibco/BRL, Cat No. 24040-016) according to protocols described (Invitrogen, San Diego).

B. Construction of Recombinant Baculoviruses.

Recombinant baculovirus ORF-2-rAcNPV expressing the entire ORF-2 of Burma strain of hepatitis E virus is constructed as described previously, He, J., et al., J. Clin. Microbiology, 31:2167 (1993), herein incorporated by reference.

Figure 5:
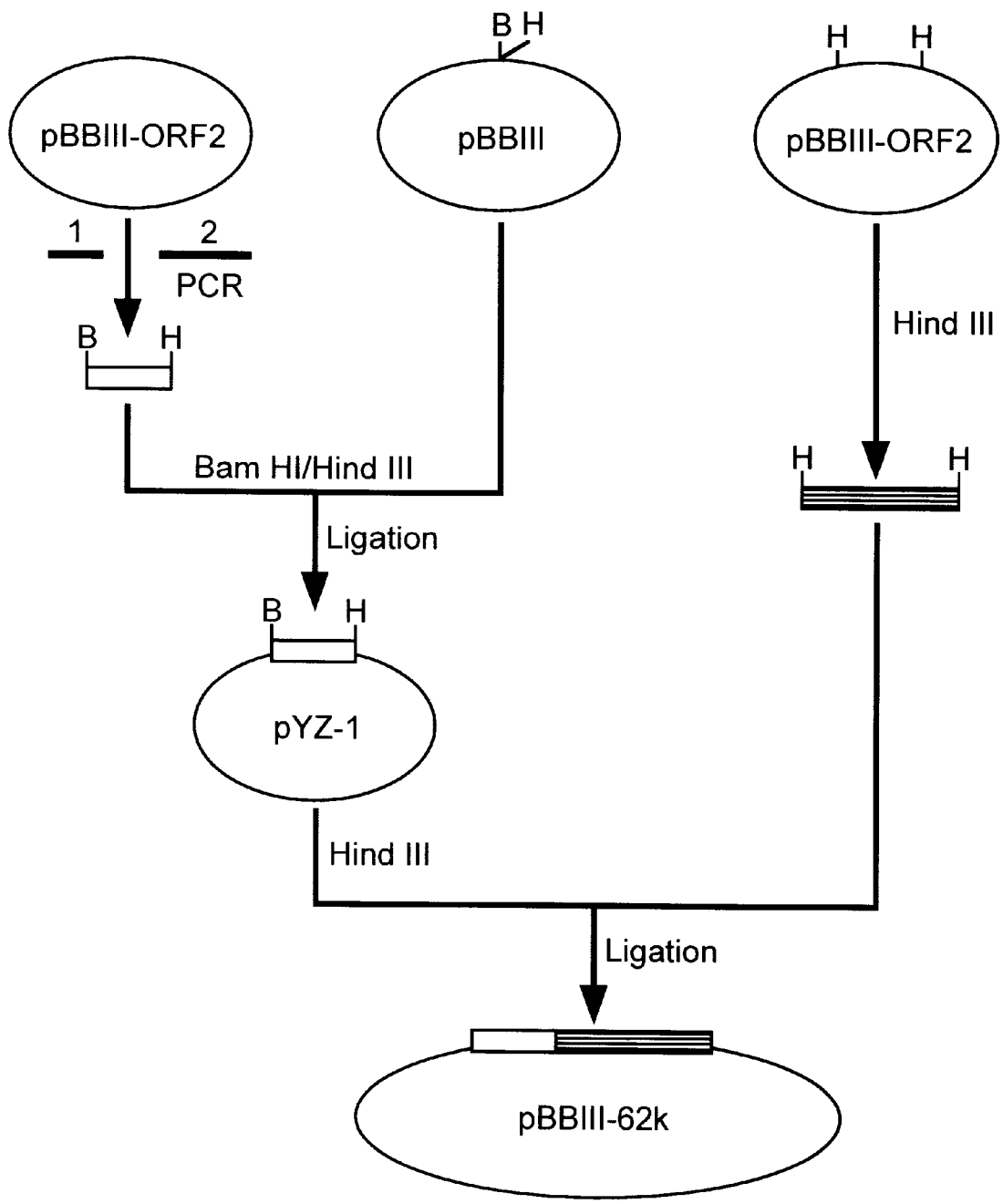
FIG. 5, presents a schematic diagram of the construction of a plasmid for expression of the re-engineered r62K antigen in baculovirus, showing a flow chart of the construction of pBBIII-62K. The bars represent the DNA fragments encoding r62K.

Construction of recombinant baculovirus pBBIII-62K expressing the C-terminal 549 amino acids of ORF2 is described as follows below and summarized in FIG. 5. In brief, a 204 base-pair (bp) DNA fragment containing nucleotides 5480 to 5684 of ORF-2 from the Burma strain of HEV (FIG. 2) is synthesized using polymerase chain reaction (PCR) and a HEV cDNA plasmid template pBBIII-ORF2, together with two primers (1)GGGGGGGATCCATAT GGCGGTCGCTCCGGCCCATGACACCCCG (5'primer), and ATTAGAAGCTTCCGTGGCCATTATATG (3'primer). The 5' primer contains a BamHI site and the 3' primer has a HindIII site to facilitate plasmid construction. The PCR product is digested with BamHI/HindIII and ligated to a baculovirus expression vector pBluBacIII (Invitrogen, San Diego) which has been previously digested with the same restriction endonucleases to form plasmid pYZ1 (FIG. 1). A 1.5 kilobase-pair (kbp) HindIII DNA fragment, corresponding to 3' portion of HEV ORF-2, is excised from a previously constructed plasmid pBBIII-OF2 and inserted into the plasmid pYZ1 at the HindIII site to form the final baculovirus transfer vector pBBIII-62K, which is subsequently used in recombinant virus construction. The nucleotide sequence derived from PCR is confirmed by DNA sequencing and the correct orientation of the HindIII/HindIII insert in pBBIII-62K is verified by restriction digestion analysis. Transfection, plaque purification, and virus amplification of recombinant baculovirus BBIII-62K is carried out according to protocols described (Invitrogen, San Diego).

C. Infection of Sf9 with Recombinant Baculovirus.

Sf9 suspension culture cells are grown to a density of 2×10$^6$ per ml and subsequently pelleted by centrifugation. The cell pellet is resuspended in 1/10 of original volume of medium containing the amount of virus which give a multiplicity of infection (MOI) of 2 plaque forming units (PFU) per cell. Virus infection is for one hour at 27° C. without stirring. The infected cells are diluted to the original density with fresh medium and maintained at 27° C. for 2–7 days with agitation (75–95 rpm). Procedures for infection of monolayer cells are described in protocols supplied by Invitrogen, Inc.

EXAMPLE 5

SDS PAGE and Immunoblot of ORF2 Produced in Sf-9 Spinner and Monolayer Cells

Figure 6A:
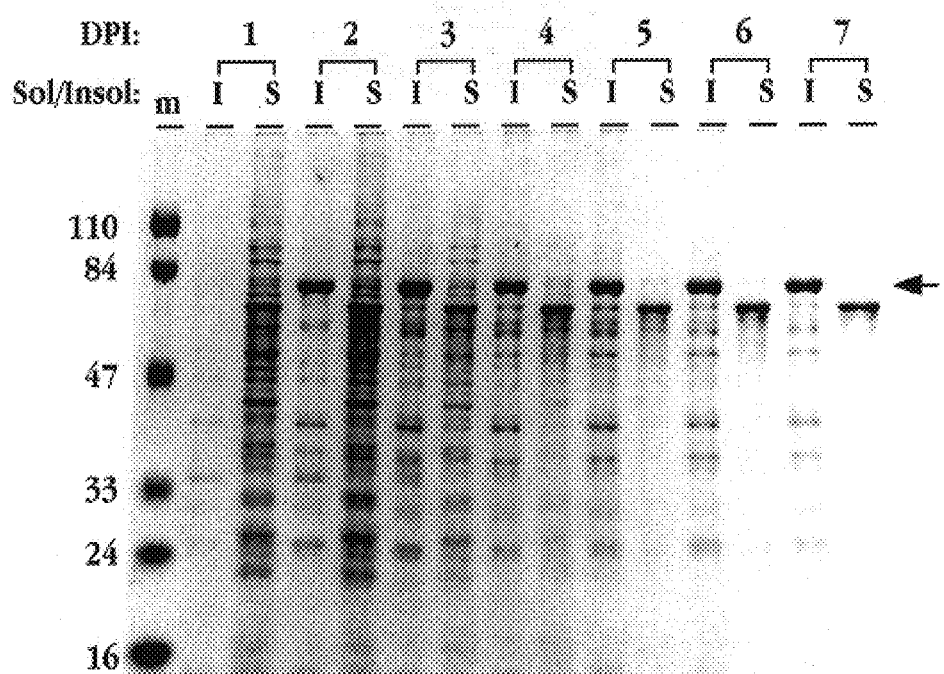
FIGS. 6A and 6B present data concerning the generation of full length ORF2 73K protein in Sf9 suspension culture and cleavage of 73K to form the 62K species in Sf9 monolayer cells.
Figure 6B:
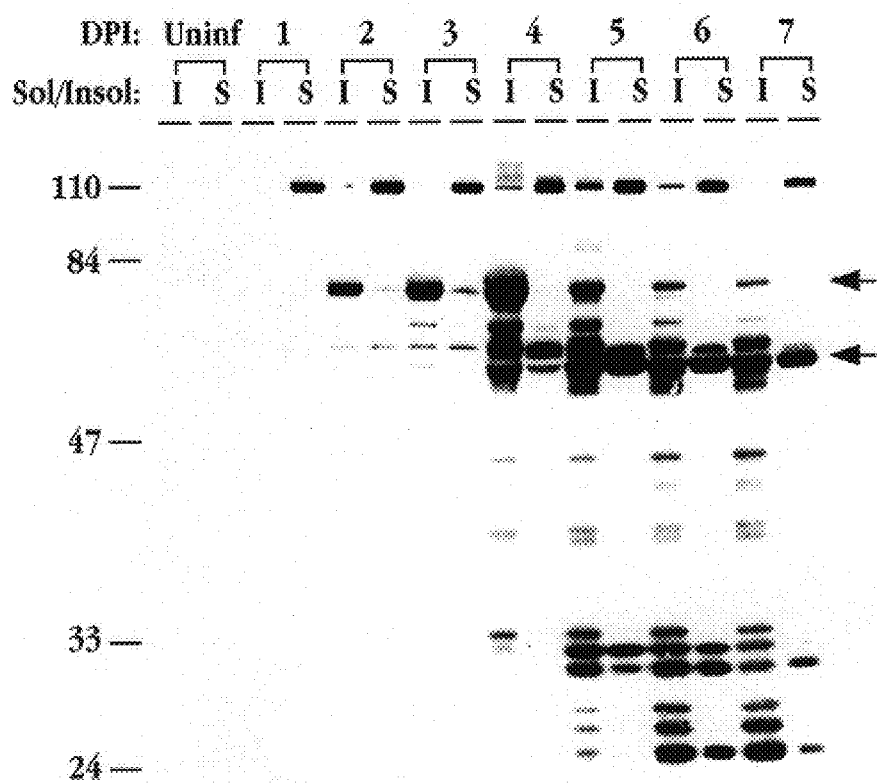
Figure 7:
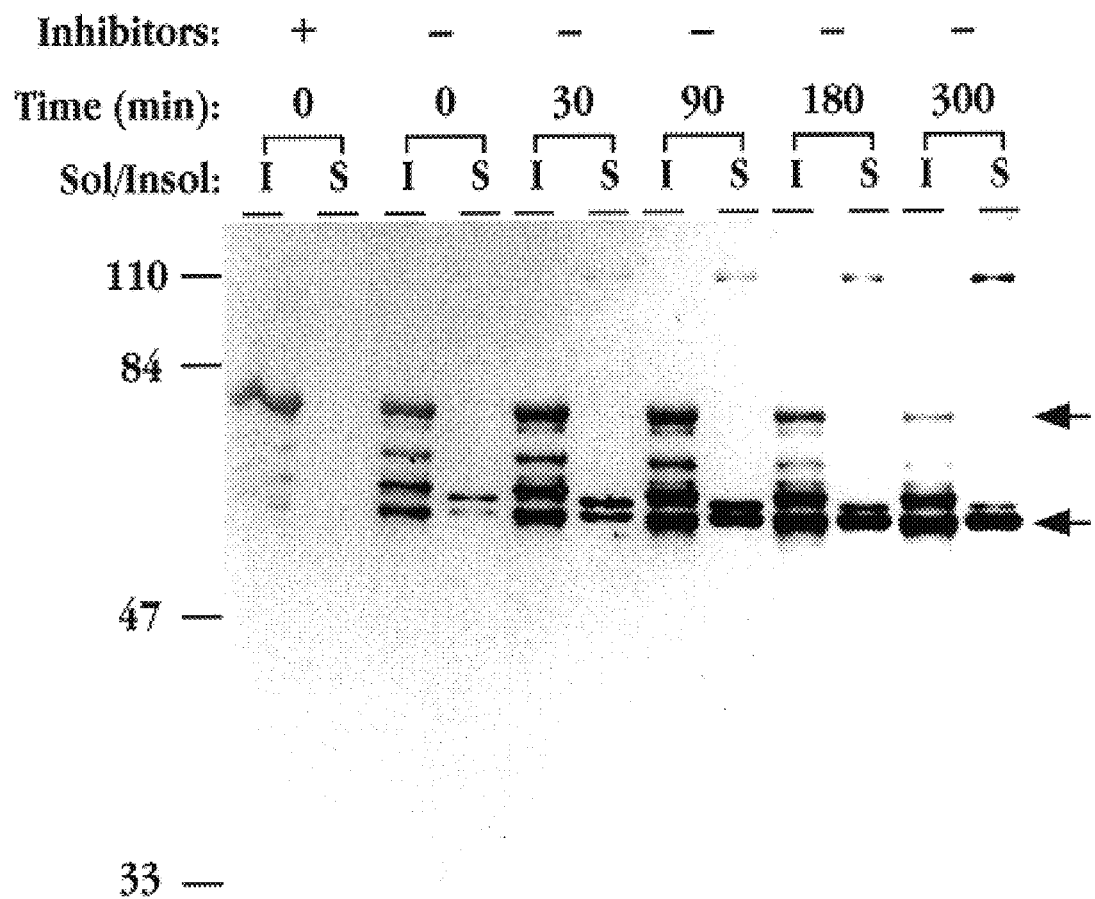
FIG. 7 shows the in vitro cleavage of the 73K full length ORF2 protein insoluble (I) protein to the 62K soluble (S) protein at various time points. The presence (+) or absence (−) of proteinase inhibitors are indicated.

Infected cell lysates from Example 5, above, prepared after various times post infection are separated by centrifugation to generate both phosphate-buffered saline (PBS)-soluable and insoluble fractions. Proteins from both fractions are electrophoresed on SDS-polyacrylamide gels, which are either stained with Coomassie-blue solution (FIG. 6*a*) or transferred to nitrocellulose paper followed by a Western blot analysis (FIG. 6*b*), as follows:

A. Anti-HEV Antiserum.

Two rabbit polyclonal antisera, anti-SG3 and anti-1L6, were generated to the 3' portion of ORF-2, 327 and 42 amino acids in length sharing the same C-terminus of ORF-2 from the Burma strain of HEV as described previously (Yarbough 1991, 1994), herein incorporated by reference.

B. SDS-PAGE and Immunoblot.

To prepare protein samples for SDS-PAGE, approximately 2×10$^6$ baculovirus-infected Sf9 cells are pelleted in mircrocentrifuge and resuspended in 150 ul of phosphate-buffered saline. Cells are lysed by sonication. The lysate is subjected to centrifugation in a microcentrifuge at 4° C. for 15 min. The supernatant and pellet are separated and denatured in protein denaturation buffer containing 20 mM Tris (pH 6.8), 10% 2-mercaptoethanol, 2% SDS, 30% (vol/vol) glycerol, and 0.1 mg/ml bromophenol blue. Protein samples are electrophoresed on 4–20% polyacrylamide-SDS gels which are then transferred to a PVDF membrane. Immunoblot is carried out using rabbit polyclonal antisera described above and a chemiluminescence detection assay (ECL kit of Amersham).

EXAMPLE 6

Purification of 73K, c62K and r62K ORF2 Products

A. Purification of Full-Length ORF2 (73K).

Recombinant baculovirus ORF2-rAcNPV infected cell pellets are resuspended in phosphate buffered saline (PBS) containing 1 mM EDTA, 1 ug/mL aprotinin, 10 ug/mL leupeptin, 0.5 mg/mL Pefabloc SC, and 10 ug/mL pepstatin at a cell density of 20% (w/v). The suspension is lysed by three passages through a Microfluidics microfluidizer M-110S at a liquid pressure of 14,000 PSI followed by centrifugation of the lysate at 10,000×g for 30 minutes at 5° C. The supernatant is decanted and the insoluble pellet is resuspended in 25 mM BICINE at pH 8.5. The suspension is recentrifuged under the same conditions and the washed pellet is extracted in 25 mM BICINE containing 0.5% SDS (w/v) for 30 minutes at ambient temperature. The extracted material is centrifuged for 30 minutes at 10,000×g at ambient temperature with the resultant supernatant separated and diluted 1:5 in 25 mM BICINE pH 8.5 in 8M urea. This material is chromatographed on a Hyper-D-S strong cation exchange column in the same buffer at a superficial linear velocity of 3000 cm/hr. Following loading and washing of the column, the 73K protein is eluted in a linear gradient of 0–400 mM NaCl in the same buffer.

The 73K protein containing fractions from the Hyper-D-S column are dialyzed against a 500 volume excess of water overnight followed by centrifugation of the dialyzate at 10,000×g at 4° C. The supernatant is discarded and the pellet extracted with 0.5% SDS in 25 mM Tris pH 8.5. Solid Cleland's Reagent (DTT) is added to a concentration of 50 mM and the solution is heated to 100° C. for three minutes followed by immediate dilution into a 100 fold volumetric excess solution containing 50 mM glycine pH 10.5, 10% glycerol, 5 mM glutathione (reduced), 0.5 mM glutathione (oxidized), and 1 g/L PEG 3500. The solution is allowed to air oxidize overnight. Following oxidation, the solution is concentrated and diafiltered by tangential cross flow filtration to 25 mM Tris pH 8.5. The material is further concentrated by centrifical ultrafiltration.

B. Purification of Processed and Re-Engineered 62K.

Recombinant baculovirus ORF2-rAcNPV or BBIII-62K infected Sf9 cell pellets are resuspended in PBS plus protease inhibitors (see above for 73K) at a cell density of 20% (w/v). The suspension is then lysed by three passages through a Microfluidics microfluidizer M-110S at a liquid pressure of 14,000 PSI followed by centrifugation of the cell lysate at 10,000×g for 30 minutes at 5° C. The decanted supernatant is pretreated by addition of solid Cleland's Reagent (DTT) to a final concentration of 50 mM followed by dialysis against two changes of a 500 volume excess of 10 mM Tris pH 8.5, 50 mM NaCl. The dialyzed material is prefiltered through a Millipore 0.22 micron filter followed by weak anion exchange chromatography on an E. Merck DEAE EMD 650(S) column at a superficial linear velocity of 100 cm/hr. The 62K protein fraction is eluted in a linear gradient from 50–500 mM NaCl over 20 column volumes. The 62K protein is further purified and buffer exchanged on a 60 cm Sephacyl S-100 column equilibrated in 25 mM Tris pH 7.2. 62K containing fractions are then chromatographed on a Poros HQ/F strong anion exchange column with the 62K eluting in a NaCl gradient of 0–1 M NaCl. The Poros HQ/F column is operated at a superficial linear velocity of 5000 cm/hr. The 62K protein is buffer exchanged by tangential cross flow diafiltration using a spiral wound cartridge (Millipore Prep TFF).

All chromatographic procedures are performed on a Waters 650E chromatography workstation utilizing Millenium 2010 software for process control and monitoring. Buffer conductivities and pH's are monitored with a Radiometer Copenhagen CDM 83 conductivity meter and a PHM 93 reference standard pH meter respectively. All buffer constituents are either biotechnology or USP grade and determined to be essentially pyrogen free by limulus amebocyte lysate assay.

EXAMPLE 7

Electron Microscopy

Protein samples are applied to Formvar-coated carbon grids and stained with 2% uranyl acetate or 2% phosphotungstic acid, pH 6.5, before they are viewed on a electron microscope. When fixation is required, protein samples are fixed in PBS containing 2% glutaraldehyde for 30 min. Buffer exchange is then carried out by centrifugation in Centricon-30 to change the sample buffer to PBS.

EXAMPLE 8

ELISA Assays

ELISA was used to compare the antigenicity of HEV protein products expressed in E. coli and baculovirus. Small scale paneling of coded sera was used to define the sensitivity and specificity of a diagnostic incorporating baculovirus expressed proteins.

A. Human Sera.

Human sera are from stored panels previously collected by our collaborators during various epidemics of hepatitis E at various geographical locations. Sera from non-human primates are from cynos and chimps experimentally infected with the hepatitis E virus at the Center for Disease Control, Atlanta, Ga.

B. ELISA.

The proteins used for immunodiagnosis include: (1) SG3 encoding 327 amino acids of ORF2 expressed as a fusion protein in E. coli (SEQ ID NO:17), (2) 73K encoding 660 amino acids of ORF2 expressed in baculovirus, and (3) 62K encoding 549 amino acids of ORF2 expressed in baculovirus. Antigens are coated individually onto the wells of polystyrene microtiter plates according to the method of Yarbough 1994, herein incorporated by reference. Each well is incubated overnight at 4° C. with 200 ng of each protein in 100 ul 0.05 M sodium carbonate pH 9.5 (1.59 g $Na_2CO_3$, 2.93 g $NaHCO_3$, 0.02% sodium azide, pH 9.5, bring to 1000 ul) buffer. After washing in PBS-0.05% polyaxyethylene (20) monolaurate "Tween 20™" (Sigma) and blocking with 200 ul of 1% bovine serum albumin (BSA) in PBS for 1.5 hours at room temperature, serum samples are diluted 1:100 in antibody diluent (1000 ml Tris buffered saline (40 mM Tris pH 7.5, 1 M NaCl), 30 ml goat serum, 10 g bovine serum albumin, fraction V, 10 g non fat milk (Carnation), 1 g gelatin (EIA) grade, and 0.2 g thimersol (preservative), see Antibody Diluent Production, following) and incubated for 30 minutes at 37° C. After removal of the primary antibody and washing to remove any unbound 1st antibody, the wells are incubated for 30 minutes at 37° C. with secondary antibody, HRP conjugated goat anti-human IgG (gamma chain specific) or goat anti-human IgM (mu chain specific). After final washing, substrate is added and the plates are read at an absorbance of 490 nm. Sera producing an O.D. value of 0.300 or greater are scored positive for HEV antibodies. This concurs with a P/N ration of greater than 3.0 and a minimum of 5 standard deviations above the mean of the normal sera.

C. Antibody Diluent Production.

Antibody Diluent is made as follows: Heat 200 ml of TBS to 60° C. and melt lg gelatin. Bring to 1000 ml with TBS. Add 10 g BSA when the temperature has cooled to 40° C. Stir at room temperature until BSA is in solution, then add 30 ul of goat serum. Add thimeresol to 0.02%. Reagent can be stored for two weeks at 4° C. Stir in milk to 1% at room temperature for 30 minutes, prior to use.

While the invention has been described with reference to particular embodiments, methods, construction and use, it will be apparent to those skilled in the art that various changes and modifications can be made without departing from the invention. For example, short peptides spanning only the immunoreactive region(s) contained in the larger peptides described herein can be substituted for the larger peptides in the methods and kits described and claimed.

It is claimed:

1. A purified 62k antigen, consisting essentially of: an amino acid sequence selected from the group consisting of SEQ ID NO:15. SEQ ID NO:16, and internally consistent variations between SEQ ID NOS:15 and 16, and having an N-terminal methionine.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:

(A) LENGTH: 2049 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (vi) ORIGINAL SOURCE:
            (C) INDIVIDUAL ISOLATE: Hepatitis E Virus (Burma strain)
                ORF-2

(xi) SEQUENCE DESCRIPTION: SEQ ID NO:1:

```
ATGCGCCCTC GGCCTATTTT GTTGCTGCTC CTCATGTTTT TGCCTATGCT GCCCGCGCCA       60

CCGCCCGGTC AGCCGTCTGG CCGCCGTCGT GGGCGGCGCA GCGGCGGTTC CGGCGGTGGT      120

TTCTGGGGTG ACCGGGTTGA TTCTCAGCCC TTCGCAATCC CCTATATTCA TCCAACCAAC      180

CCCTTCGCCC CCGATGTCAC CGCTGCGGCC GGGGCTGGAC CTCGTGTTCG CCAACCCGCC      240

CGACCACTCG GCTCCGCTTG GCGTGACCAG GCCCAGCGCC CCGCCGTTGC CTCACGTCGT      300

AGACCTACCA CAGCTGGGGC CGCGCCGCTA ACCGCGGTCG CTCCGGCCCA TGACACCCCG      360

CCAGTGCCTG ATGTCGACTC CCGCGGCGCC ATCTTGCGCC GGCAGTATAA CCTATCAACA      420

TCTCCCCTTA CCTCTTCCGT GGCCACCGGC ACTAACCTGG TTCTTTATGC CGCCCCTCTT      480

AGTCCGCTTT TACCCCTTCA GGACGGCACC AATACCCATA TAATGGCCAC GGAAGCTTCT      540

AATTATGCCC AGTACCGGGT TGCCCGTGCC ACAATCCGTT ACCGCCCGCT GGTCCCCAAT      600

GCTGTCGGCG GTTACGCCAT CTCCATCTCA TTCTGGCCAC AGACCACCAC CACCCCGACG      660

TCCGTTGATA TGAATTCAAT AACCTCGACG GATGTTCGTA TTTTAGTCCA GCCCGGCATA      720

GCCTCTGAGC TTGTGATCCC AAGTGAGCGC CTACACTATC GTAACCAAGG CTGGCGCTCC      780

GTCGAGACCT CTGGGGTGGC TGAGGAGGAG GCTACCTCTG GTCTTGTTAT GCTTTGCATA      840

CATGGCTCAC TCGTAAATTC CTATACTAAT ACACCCTATA CCGGTGCCCT CGGGCTGTTG      900

GACTTTGCCC TTGAGCTTGA GTTTCGCAAC CTTACCCCCG GTAACACCAA TACGCGGGTC      960

TCCCGTTATT CCAGCACTGC TCGCCACCGC CTTCGTCGCG GTGCGGACGG GACTGCCGAG     1020

CTCACCACCA CGGCTGCTAC CCGCTTTATG AAGGACCTCT ATTTTACTAG TACTAATGGT     1080

GTCGGTGAGA TCGGCCGCGG GATAGCCCTC ACCCTGTTCA ACCTTGCTGA CACTCTGCTT     1140

GGCGGCCTGC CGACAGAATT GATTTCGTCG GCTGGTGGCC AGCTGTTCTA CTCCCGTCCC     1200

GTTGTCTCAG CCAATGGCGA GCCGACTGTT AAGTTGTATA CATCTGTAGA GAATGCTCAG     1260

CAGGATAAGG GTATTGCAAT CCCGCATGAC ATTGACCTCG GAGAATCTCG TGTGGTTATT     1320

CAGGATTATG ATAACCAACA TGAACAAGAT CGGCCGACGC CTTCTCCAGC CCATCGCGC     1380

CCTTTCTCTG TCCTTCGAGC TAATGATGTG CTTTGGCTCT CTCTCACCGC TGCCGAGTAT     1440

GACCAGTCCA CTTATGGCTC TTCGACTGGC CCAGTTTATG TTTCTGACTC TGTGACCTTG     1500

GTTAATGTTG CGACCGGCGC GCAGGCCGTT GCCCGGTCGC TCGATTGGAC CAAGGTCACA     1560

CTTGACGGTC GCCCCCTCTC CACCATCCAG CAGTACTCGA AGACCTTCTT TGTCCTGCCG     1620

CTCCGCGGTA AGCTCTCTTT CTGGGAGGCA GGCACAACTA AAGCCGGGTA CCCTTATAAT     1680

TATAACACCA CTGCTAGCGA CCAACTGCTT GTCGAGAATG CCGCCGGGCA CCGGGTCGCT     1740

ATTTCCACTT ACACCACTAG CCTGGGTGCT GGTCCCGTCT CCATTTCTGC GGTTGCCGTT     1800

TTAGCCCCCC ACTCTGCGCT AGCATTGCTT GAGGATACCT TGGACTACCC TGCCCGCGCC     1860

CATACTTTTG ATGATTTCTG CCCAGAGTGC CGCCCCCTTG GCCTTCAGGG CTGCGCTTTC     1920
```

```
CAGTCTACTG TCGCTGAGCT TCAGCGCCTT AAGATGAAGG TGGGTAAAAC TCGGGAGTTG      1980

TAGTTTATTT GCTTGTGCCC CCCTTCTTTC TGTTGCTTAT TTCTCATTTC TGCGTTCCGC      2040

GCTCCCTGA                                                              2049

(2) INFORMATION FOR SEQ ID NO:2:

(i) SEQUENCE CHARACTERISTICS:
        (A) LENGTH: 2055 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E Virus (Mexico Strain)
            ORF-2 region (xi) SEQUENCE DESCRIPTION: SEQ ID NO:2:

ATGCGCCCTA GGCCTCTTTT GCTGTTGTTC CTCTTGTTTC TGCCTATGTT GCCCGCGCCA        60

CCGACCGGTC AGCCGTCTGG CCGCCGTCGT GGGCGGCGCA GCGGCGGTAC CGGCGGTGGT       120

TTCTGGGGTG ACCGGGTTGA TTCTCAGCCC TTCGCAATCC CCTATATTCA TCCAACCAAC       180

CCCTTTGCCC AGACGTTGCC GCTGCGTCC GGGTCTGGAC CTCGCCTTCG CCAACCAGCC        240

CGGCCACTTG GCTCCACTTG GCGAGATCAG GCCCAGCGCC CCTCCGCTGC CTCCCGTCGC       300

CGACCTGCCA CAGCCGGGGC TGCGGCGCTG ACGGCTGTGG CGCCTGCCCA TGACACCTCA       360

CCCGTCCCGG ACGTTGATTC TCGCGGTGCA ATTCTACGCC GCCAGTATAA TTTGTCTACT       420

TCACCCCTGA CATCCTCTGT GGCCTCTGGC ACTAATTTAG TCCTGTATGC AGCCCCCCTT       480

AATCCGCCTC TGCCGCTGCA GGACGGTACT AATACTCACA TTATGGCCAC AGAGGCCTCC       540

AATTATGCAC AGTACCGGGT TGCCCGCGCT ACTATCCGTT ACCGGCCCCT AGTGCCTAAT       600

GCAGTTGGAG GCTATGCTAT ATCCATTTCT TTCTGGCCTC AAACAACCAC AACCCCTACA       660

TCTGTTGACA TGAATTCCAT TACTTCCACT GATGTCAGGA TTCTTGTTCA ACCTGGCATA       720

GCATCTGAAT TGGTCATCCC AAGCGAGCGC CTTCACTACC GCAATCAAGG TTGGCGCTCG       780

GTTGAGACAT CTGGTGTTGC TGAGGAGGAA GCCACCTCCG GTCTTGTCAT GTTATGCATA       840

CATGGCTCTC CAGTTAACTC CTATACCAAT ACCCCTTATA CCGGTGCCCT TGGCTTACTG       900

GACTTTGCCT TAGAGCTTGA GTTTCGCAAT CTCACCACCT GTAACACCAA TACACGTGTG       960

TCCCGTTACT CCAGCACTGC TCGTCACTCC GCCCGAGGGG CCGACGGGAC TGCGGAGCTG      1020

ACCACAACTG CAGCCACCAG GTTCATGAAA GATCTCCACT TTACCGGCCT TAATGGGGTA      1080

GGTGAAGTCG GCCGCGGGAT AGCTCTAACA TTACTTAACC TTGCTGACAC GCTCCTCGGC      1140

GGGCTCCCGA CAGAATTAAT TTCGTCGGCT GGCGGGCAAC TGTTTTATTC CCGCCCGGTT      1200

GTCTCAGCCA ATGGCGAGCC AACCGTGAAG CTCTATACAT CAGTGGAGAA TGCTCAGCAG      1260

GATAAGGGTG TTGCTATCCC CCACGATATC GATCTTGGTG ATTCGCGTGT GGTCATTCAG      1320

GATTATGACA ACCAGCATGA GCAGGATCGG CCCACCCCGT CGCCTGCGCC ATCTCGGCCT      1380

TTTTCTGTTC TCCGAGCAAA TGATGTACTT TGGCTGTCCC TCACTGCAGC CGAGTATGAC      1440

CAGTCCACTT ACGGGTCGTC AACTGGCCCG GTTTATATCT CGGACAGCGT GACTTTGGTG      1500

AATGTTGCGA CTGGCGCGCA GGCCGTAGCC CGATCGCTTG ACTGGTCCAA AGTCACCCTC      1560

GACGGGCGGC CCCTCCCGAC TGTTGAGCAA TATTCCAAGA CATTCTTTGT GCTCCCCCTT      1620
```

-continued

```
CGTGGCAAGC TCTCCTTTTG GGAGGCCGGC ACAACAAAAG CAGGTTATCC TTATAATTAT     1680

AATACTACTG CTAGTGACCA GATTCTGATT GAAAATGCTG CCGGCCATCG GGTCGCCATT     1740

TCAACCTATA CCACCAGGCT TGGGGCCGGT CCGGTCGCCA TTTCTGCGGC CGCGGTTTTG     1800

GCTCCACGCT CCGCCCTGGC TCTGCTGGAG GATACTTTTG ATTATCCGGG GCGGGCGCAC     1860

ACATTTGATG ACTTCTGCCC TGAATGCCGC GCTTTAGGCC TCCAGGGTTG TGCTTTCCAG     1920

TCAACTGTCG CTGAGCTCCA GCGCCTTAAA GTTAAGGTGG GTAAAACTCG GGAGTTGTAG     1980

TTTATTTGGC TGTGCCCACC TACTTATATC TGCTGATTTC CTTTATTTCC TTTTTCTCGG     2040

TCCCGCGCTC CCTGA                                                     2055
```

(2) INFORMATION FOR SEQ ID NO:3:

(i) SEQUENCE CHARACTERISTICS:
        (A) LENGTH: 1647 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E virus (Burma) r62kDa,
            FIGURE 2

(xi) SEQUENCE DESCRIPTION: SEQ ID NO:3:

```
GCGGTCGCTC CGGCCCATGA CACCCCGCCA GTGCCTGATG TCGACTCCCG CGGCGCCATC       60

TTGCGCCGGC AGTATAACCT ATCAACATCT CCCCTTACCT CTTCCGTGGC CACCGGCACT      120

AACCTGGTTC TTTATGCCGC CCCTCTTAGT CCGCTTTTAC CCCTTCAGGA CGGCACCAAT      180

ACCCATATAA TGGCCACGGA AGCTTCTAAT TATGCCCAGT ACCGGGTTGC CCGTGCCACA      240

ATCCGTTACC GCCCGCTGGT CCCCAATGCT GTCGGCGGTT ACGCCATCTC CATCTCATTC      300

TGGCCACAGA CCACCACCAC CCCGACGTCC GTTGATATGA ATTCAATAAC CTCGACGGAT      360

GTTCGTATTT TAGTCCAGCC CGGCATAGCC TCTGAGCTTG TGATCCCAAG TGAGCGCCTA      420

CACTATCGTA ACCAAGGCTG GCGCTCCGTC GAGACCTCTG GGGTGGCTGA GGAGGAGGCT      480

ACCTCTGGTC TTGTTATGCT TTGCATACAT GGCTCACTCG TAAATTCCTA TACTAATACA      540

CCCTATACCG GTGCCCTCGG GCTGTTGGAC TTTGCCCTTG AGCTTGAGTT TCGCAACCTT      600

ACCCCCGGTA ACACCAATAC GCGGGTCTCC CGTTATTCCA GCACTGCTCG CCACCGCCTT      660

CGTCGCGGTG CGGACGGGAC TGCCGAGCTC ACCACCACGG CTGCTACCCG CTTTATGAAG      720

GACCTCTATT TTACTAGTAC TAATGGTGTC GGTGAGATCG GCCGCGGGAT AGCCCTCACC      780

CTGTTCAACC TTGCTGACAC TCTGCTTGGC GGCCTGCCGA CAGAATTGAT TTCGTCGGCT      840

GGTGGCCAGC TGTTCTACTC CCGTCCCGTT GTCTCAGCCA ATGGCGAGCC GACTGTTAAG      900

TTGTATACAT CTGTAGAGAA TGCTCAGCAG GATAAGGGTA TTGCAATCCC GCATGACATT      960

GACCTCGGAG AATCTCGTGT GGTTATTCAG GATTATGATA ACCAACATGA ACAAGATCGG     1020

CCGACGCCTT CTCCAGCCCC ATCGCGCCCT TTCTCTGTCC TTCGAGCTAA TGATGTGCTT     1080

TGGCTCTCTC TCACCGCTGC CGAGTATGAC CAGTCCACTT ATGGCTCTTC GACTGGCCCA     1140

GTTTATGTTT CTGACTCTGT GACCTTGGTT AATGTTGCGA CCGGCGCGCA GGCCGTTGCC     1200

CGGTCGCTCG ATTGGACCAA GGTCACACTT GACGGTCGCC CCCTCTCCAC CATCCAGCAG     1260

TACTCGAAGA CCTTCTTTGT CCTGCCGCTC CGCGGTAAGC TCTCTTTCTG GGAGGCAGGC     1320
```

-continued

```
ACAACTAAAG CCGGGTACCC TTATAATTAT AACACCACTG CTAGCGACCA ACTGCTTGTC   1380

GAGAATGCCG CCGGGCACCG GGTCGCTATT TCCACTTACA CCACTAGCCT GGGTGCTGGT   1440

CCCGTCTCCA TTTCTGCGGT TGCCGTTTTA GCCCCCCACT CTGCGCTAGC ATTGCTTGAG   1500

GATACCTTGG ACTACCCTGC CCGCGCCCAT ACTTTTGATG ATTTCTGCCC AGAGTGCCGC   1560

CCCCTTGGCC TTCAGGGCTG CGCTTTCCAG TCTACTGTCG CTGAGCTTCA GCGCCTTAAG   1620

ATGAAGGTGG GTAAAACTCG GGAGTTG                                       1647
```

(2) INFORMATION FOR SEQ ID NO:4:

(i) SEQUENCE CHARACTERISTICS:
(A) LENGTH: 1644 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E virus (Mexico strain) r62kDa, FIGURE 2

(xi) SEQUENCE DESCRIPTION: SEQ ID NO:4:

```
GCTGTGGCGC CTGCCCATGA CACCTCACCC GTCCCGGACG TTGATTCTCG CGGTGCAATT     60

CTACGCCGCC AGTATAATTT GTCTACTTCA CCCCTGACAT CCTCTGTGGC CTCTGGCACT    120

AATTTAGTCC TGTATGCAGC CCCCCTTAAT CCGCCTCTGC CGCTGCAGGA CGGTACTAAT    180

ACTCACATTA TGGCCACAGA GGCCTCCAAT TATGCACAGT ACCGGGTTGC CCGCGCTACT    240

ATCCGTTACC GGCCCCTAGT GCCTAATGCA GTTGGAGGCT ATGCTATATC CATTTCTTTC    300

TGGCCTCAAA CAACCACAAC CCCTACATCT GTTGACATGA ATTCCATTAC TTCCACTGAT    360

GTCAGGATTC TTGTTCAACC TGGCATAGCA TCTGAATTGG TCATCCCAAG CGAGCGCCTT    420

CACTACCGCA ATCAAGGTTG GCGCTCGGTT GAGACATCTG GTGTTGCTGA GGAGGAAGCC    480

ACCTCCGGTC TTGTCATGTT ATGCATACAT GGCTCTCCAG TTAACTCCTA TACCAATACC    540

CCTTATACCG GTGCCCTTGG CTTACTGGAC TTTGCCTTAG AGCTTGAGTT TCGCAATCTC    600

ACCACCTGTA ACACCAATAC ACGTGTGTCC CGTTACTCCA GCACTGCTCG TCACTCCGCC    660

CGAGGGGCCG ACGGGACTGC GGAGCTGACC ACAACTGCAG CCACCAGGTT CATGAAAGAT    720

CTCCACTTTA CCGGCCTTAA TGGGGTAGGT GAAGTCGGCC GCGGGATAGC TCTAACATTA    780

CTTAACCTTG CTGACACGCT CCTCGGCGGG CTCCCGACAG AATTAATTTC GTCGGCTGGC    840

GGGCAACTGT TTTATTCCCG CCCGGTTGTC TCAGCCAATG GCGAGCCAAC CGTGAAGCTC    900

TATACATCAG TGGAGAATGC TCAGCAGGAT AAGGGTGTTG CTATCCCCCA CGATATCGAT    960

CTTGGTGATT CGCGTGTGGT CATTCAGGAT TATGACAACC AGCATGAGCA GGATCGGCCC   1020

ACCCCGTCGC CTGCGCCATC TCGGCCTTTT TCTGTTCTCC GAGCAAATGA TGTACTTTGG   1080

CTGTCCCTCA CTGCAGCCGA GTATGACCAG TCCACTTACG GGTCGTCAAC TGGCCCGGTT   1140

TATATCTCGG ACAGCGTGAC TTTGGTGAAT GTTGCGACTG GCGCGCAGGC CGTAGCCCGA   1200

TCGCTTGACT GGTCCAAAGT CACCCTCGAC GGGCGGCCCC TCCCGACTGT TGAGCAATAT   1260

TCCAAGACAT TCTTTGTGCT CCCCCTTCGT GGCAAGCTCT CCTTTTGGGA GGCCGGCACA   1320

ACAAAAGCAG GTTATCCTTA TAATTATAAT ACTACTGCTA GTGACCAGAT TCTGATTGAA   1380

AATGCTGCCG GCCATCGGGT CGCCATTTCA ACCTATACCA CCAGGCTTGG GGCCGGTCCG   1440
```

-continued

```
GTCGCCATTT CTGCGGCCGC GGTTTTGGCT CCACGCTCCG CCCTGGCTCT GCTGGAGGAT   1500

ACTTTTGATT ATCCGGGGCG GGCGCACACA TTTGATGACT TCTGCCCTGA ATGCCGCGCT   1560

TTAGGCCTCC AGGGTTGTGC TTTCCAGTCA ACTGTCGCTG AGCTCCAGCG CCTTAAAGTT   1620

AAGGTGGGTA AAACTCGGGA GTTG                                          1644
```

(2) INFORMATION FOR SEQ ID NO:5:

(i) SEQUENCE CHARACTERISTICS:
(A) LENGTH: 984 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E Virus (Burma strain) SG3 region (xi) SEQUENCE DESCRIPTION: SEQ ID NO:5:

```
GGTGCGGACG GGACTGCCGA GCTCACCACC ACGGCTGCTA CCCGCTTTAT GAAGGACCTC     60

TATTTTACTA GTACTAATGG TGTCGGTGAG ATCGGCCGCG GGATAGCCCT CACCCTGTTC    120

AACCTTGCTG ACACTCTGCT TGGCGGCCTG CCGACAGAAT TGATTTCGTC GGCTGGTGGC    180

CAGCTGTTCT ACTCCCGTCC CGTTGTCTCA GCCAATGGCG AGCCGACTGT TAAGTTGTAT    240

ACATCTGTAG AGAATGCTCA GCAGGATAAG GGTATTGCAA TCCCGCATGA CATTGACCTC    300

GGAGAATCTC GTGTGGTTAT TCAGGATTAT GATAACCAAC ATGAACAAGA TCGGCCGACG    360

CCTTCTCCAG CCCCATCGCG CCCTTTCTCT GTCCTTCGAG CTAATGATGT GCTTTGGCTC    420

TCTCTCACCG CTGCCGAGTA TGACCAGTCC ACTTATGGCT CTTCGACTGG CCCAGTTTAT    480

GTTTCTGACT CTGTGACCTT GGTTAATGTT GCGACCGGCG CGCAGGCCGT TGCCCGGTCG    540

CTCGATTGGA CCAAGGTCAC ACTTGACGGT CGCCCCCTCT CCACCATCCA GCAGTACTCG    600

AAGACCTTCT TTGTCCTGCC GCTCCGCGGT AAGCTCTCTT TCTGGGAGGC AGGCACAACT    660

AAAGCCGGGT ACCCTTATAA TTATAACACC ACTGCTAGCG ACCAACTGCT TGTCGAGAAT    720

GCCGCCGGGC ACCGGGTCGC TATTTCCACT TACACCACTA GCCTGGGTGC TGGTCCCGTC    780

TCCATTTCTG CGGTTGCCGT TTTAGCCCCC CACTCTGCGC TAGCATTGCT TGAGGATACC    840

TTGGACTACC CTGCCCGCGC CCATACTTTT GATGATTTCT GCCCAGAGTG CCGCCCCCTT    900

GGCCTTCAGG GCTGCGCTTT CCAGTCTACT GTCGCTGAGC TTCAGCGCCT TAAGATGAAG    960

GTGGGTAAAA CTCGGGAGTT GTAG                                           984
```

(2) INFORMATION FOR SEQ ID NO:6:

(i) SEQUENCE CHARACTERISTICS:
(A) LENGTH: 984 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatits E Virus (Mexico strain) SG3 region (xi) SEQUENCE DESCRIPTION: SEQ ID NO:6:

```
GGGGCCGACG GGACTGCGGA GCTGACCACA ACTGCAGCCA CCAGGTTCAT GAAAGATCTC      60

CACTTTACCG GCCTTAATGG GGTAGGTGAA GTCGGCCGCG GGATAGCTCT AACATTACTT     120

AACCTTGCTG ACACGCTCCT CGGCGGGCTC CCGACAGAAT TAATTTCGTC GGCTGGCGGG     180

CAACTGTTTT ATTCCCGCCC GGTTGTCTCA GCCAATGGCG AGCCAACCGT GAAGCTCTAT     240

ACATCAGTGG AGAATGCTCA GCAGGATAAG GGTGTTGCTA TCCCCCACGA TATCGATCTT     300

GGTGATTCGC GTGTGGTCAT TCAGGATTAT GACAACCAGC ATGAGCAGGA TCGGCCCACC     360

CCGTCGCCTG CGCCATCTCG GCCTTTTTCT GTTCTCCGAG CAAATGATGT ACTTTGGCTG     420

TCCCTCACTG CAGCCGAGTA TGACCAGTCC ACTTACGGGT CGTCAACTGG CCCGGTTTAT     480

ATCTCGGACA GCGTGACTTT GGTGAATGTT GCGACTGGCG CGCAGGCCGT AGCCCGATCG     540

CTTGACTGGT CCAAAGTCAC CCTCGACGGG CGGCCCCTCC CGACTGTTGA GCAATATTCC     600

AAGACATTCT TTGTGCTCCC CCTTCGTGGC AAGCTCTCCT TTTGGGAGGC CGGCACAACA     660

AAAGCAGGTT ATCCTTATAA TTATAATACT ACTGCTAGTG ACCAGATTCT GATTGAAAAT     720

GCTGCCGGCC ATCGGGTCGC CATTTCAACC TATACCACCA GGCTTGGGGC CGGTCCGGTC     780

GCCATTTCTG CGGCCGCGGT TTTGGCTCCA CGCTCCGCCC TGGCTCTGCT GGAGGATACT     840

TTTGATTATC CGGGGCGGGC GCACACATTT GATGACTTCT GCCCTGAATG CCGCGCTTTA     900

GGCCTCCAGG GTTGTGCTTT CCAGTCAACT GTCGCTGAGC TCCAGCGCCT TAAAGTTAAG     960

GTGGGTAAAA CTCGGGAGTT GTAG                                            984

(2) INFORMATION FOR SEQ ID NO:7:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E Virus (Burma strain)
            406.3-2

(xi) SEQUENCE DESCRIPTION: SEQ ID NO:7:

ACCTTGGACT ACCCTGCCCG CGCCCATACT TTTGATGATT TCTGCCCAGA GTGCCGCCCC      60

CTTGGCCTTC AGGGCTGCGC TTTCCAGTCT ACTGTCGCTG AGCTTCAGCG CCTTAAGATG     120

AAGGTGGGTA AAACTCGGGA GTTGTAG                                         147

(2) INFORMATION FOR SEQ ID NO:8:

(i) SEQUENCE CHARACTERISTICS:
        (A) LENGTH: 147 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E Virus (Mexico strain)
            406.3-2

(xi) SEQUENCE DESCRIPTION: SEQ ID NO:8:
```

-continued

```
ACTTTTGATT ATCCGGGGCG GGCGCACACA TTTGATGACT TCTGCCCTGA ATGCCGCGCT     60

TTAGGCCTCC AGGGTTGTGC TTTCCAGTCA ACTGTCGCTG AGCTCCAGCG CCTTAAAGTT    120

AAGGTGGGTA AAACTCGGGA GTTGTAG                                        147
```

(2) INFORMATION FOR SEQ ID NO:9:

(i) SEQUENCE CHARACTERISTICS:
(A) LENGTH: 372 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E Virus (Burma Strain) ORF-3 region (xi) SEQUENCE DESCRIPTION: SEQ ID NO:9:

```
ATGAATAACA TGTCTTTTGC TGCGCCCATG GGTTCGCGAC CATGCGCCCT CGGCCTATTT     60

TGTTGCTGCT CCTCATGTTT TTGCCTATGC TGCCCGCGCC ACCGCCCGGT CAGCCGTCTG    120

GCCGCCGTCG TGGGCGGCGC AGCGGCGGTT CCGGCGGTGG TTTCTGGGGT GACCGGGTTG    180

ATTCTCAGCC CTTCGCAATC CCCTATATTC ATCCAACCAA CCCCTTCGCC CCCGATGTCA    240

CCGCTGCGGC CGGGGCTGGA CCTCGTGTTC GCCAACCCGC CCGACCACTC GGCTCCGCTT    300

GGCGTGACCA GGCCCAGCGC CCCGCCGTTG CCTCACGTCG TAGACCTACC ACAGCTGGGG    360

CCGCGCCGCT AA                                                        372
```

(2) INFORMATION FOR SEQ ID NO:10:

(i) SEQUENCE CHARACTERISTICS:
(A) LENGTH: 372 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E Virus (Mexico Strain) ORF-3 region (xi) SEQUENCE DESCRIPTION: SEQ ID NO:10:

```
ATGAATAACA TGTGGTTTGC TGCGCCCATG GGTTCGCCAC CATGCGCCCT AGGCCTCTTT     60

TGCTGTTGTT CCTCTTGTTT CTGCCTATGT TGCCCGCGCC ACCGACCGGT CAGCCGTCTG    120

GCCGCCGTCG TGGGCGGCGC AGCGGCGGTA CCGGCGGTGG TTTCTGGGGT GACCGGGTTG    180

ATTCTCAGCC CTTCGCAATC CCCTATATTC ATCCAACCAA CCCCTTTGCC CCAGACGTTG    240

CCGCTGCGTC CGGGTCTGGA CCTCGCCTTC GCCAACCAGC CCGGCCACTT GGCTCCACTT    300

GGCGAGATCA GGCCCAGCGC CCCTCCGCTG CCTCCCGTCG CCGACCTGCC ACAGCCGGGG    360

CTGCGGCGCT GA                                                        372
```

(2) INFORMATION FOR SEQ ID NO:11:

(i) SEQUENCE CHARACTERISTICS:
(A) LENGTH: 99 base pairs
(B) TYPE: nucleic acid
(C) STRANDEDNESS: double (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: Hepatitis E Virus (Burma strain)
            406.4-2 region (xi) SEQUENCE DESCRIPTION: SEQ ID NO:11:

```
GCCAACCCGC CCGACCACTC GGCTCCGCTT GGCGTGACCA GGCCCAGCGC CCCGCCGTTG     60

CCTCACGTCG TAGACCTACC ACAGCTGGGG CCGCGCCGC                            99
```

(2) INFORMATION FOR SEQ ID NO:12:

(i) SEQUENCE CHARACTERISTICS:
(A) LENGTH: 99 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (vi) ORIGINAL SOURCE:
(C) INDIVIDUAL ISOLATE: Hepatitis E Virus (Mexico strain) 406.4-2 region (xi) SEQUENCE DESCRIPTION: SEQ ID NO:12:

```
GCCAACCAGC CCGGCCACTT GGCTCCACTT GGCGAGATCA GGCCCAGCGC CCCTCCGCTG     60

CCTCCCGTCG CCGACCTGCC ACAGCCGGGG CTGCGGCGC                            99
```

(2) INFORMATION FOR SEQ ID NO:13:

(i) SEQUENCE CHARACTERISTICS:
(A) LENGTH: 660 amino acids
(B) TYPE: amino acid
(D) TOPOLOGY: linear (ii) MOLECULE TYPE: protein (iii) HYPOTHETICAL: NO (vi) ORIGINAL SOURCE:
(C) INDIVIDUAL ISOLATE: Hepatitis E Virus (Burma strain) ORF-2

(xi) SEQUENCE DESCRIPTION: SEQ ID NO:13:

```
Met Arg Pro Arg Pro Ile Leu Leu Leu Leu Leu Met Phe Leu Pro Met
1               5                   10                  15

Leu Pro Ala Pro Pro Pro Gly Gln Pro Ser Gly Arg Arg Arg Gly Arg
            20                  25                  30

Arg Ser Gly Gly Ser Gly Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Pro Val Pro Asp Val Asp Ser Arg
```

```
              115                 120                 125
Gly Ala Ile Leu Arg Arg Gln Tyr Asn Leu Ser Thr Ser Pro Leu Thr
        130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Leu Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu Tyr Phe Thr Ser Thr Asn Gly Val Gly Glu Ile Gly Arg Gly Ile
        355                 360                 365

Ala Leu Thr Leu Phe Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
        515                 520                 525

Ile Gln Gln Tyr Ser Lys Thr Phe Phe Val Leu Pro Leu Arg Gly Lys
    530                 535                 540
```

```
Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
                580                 585                 590

Val Ser Ile Ser Ala Val Ala Val Leu Ala Pro His Ser Ala Leu Ala
            595                 600                 605

Leu Leu Glu Asp Thr Leu Asp Tyr Pro Ala Arg Ala His Thr Phe Asp
    610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660
```

(2) INFORMATION FOR SEQ ID NO:14:

(i) SEQUENCE CHARACTERISTICS:
        (A) LENGTH: 659 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Mexico Strain)
            ORF-2

(xi) SEQUENCE DESCRIPTION: SEQ ID NO:14:

```
Met Arg Pro Arg Pro Leu Leu Leu Phe Leu Leu Phe Leu Pro Met
1               5                   10                  15

Leu Pro Ala Pro Pro Thr Gly Gln Pro Ser Gly Arg Arg Arg Gly Arg
                20                  25                  30

Arg Ser Gly Gly Thr Gly Gly Gly Phe Trp Gly Asp Arg Val Asp Ser
            35                  40                  45

Gln Pro Phe Ala Ile Pro Tyr Ile His Pro Thr Asn Pro Phe Ala Pro
50                  55                  60

Asp Val Ala Ala Ala Ser Gly Ser Gly Pro Arg Leu Arg Gln Pro Ala
65                  70                  75                  80

Arg Pro Leu Gly Ser Thr Trp Arg Asp Gln Ala Gln Arg Pro Ser Ala
                85                  90                  95

Ala Ser Arg Arg Arg Pro Ala Thr Ala Gly Ala Ala Ala Leu Thr Ala
                100                 105                 110

Val Ala Pro Ala His Asp Thr Ser Pro Val Pro Asp Val Asp Ser Arg
            115                 120                 125

Gly Ala Ile Leu Arg Arg Gln Tyr Asn Leu Ser Thr Ser Pro Leu Thr
            130                 135                 140

Ser Ser Val Ala Ser Gly Thr Asn Leu Val Leu Tyr Ala Ala Pro Leu
145                 150                 155                 160

Asn Pro Pro Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
                180                 185                 190
```

```
Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Thr Cys Asn Thr Asn Thr Arg Val
305                 310                 315                 320

Ser Arg Tyr Ser Ser Thr Ala Arg His Ser Ala Arg Gly Ala Asp Gly
                325                 330                 335

Thr Ala Glu Leu Thr Thr Thr Ala Ala Thr Arg Phe Met Lys Asp Leu
            340                 345                 350

His Phe Thr Gly Leu Asn Gly Val Gly Glu Val Gly Arg Gly Ile Ala
            355                 360                 365

Leu Thr Leu Leu Asn Leu Ala Asp Thr Leu Leu Gly Gly Leu Pro Thr
    370                 375                 380

Glu Leu Ile Ser Ser Ala Gly Gly Gln Leu Phe Tyr Ser Arg Pro Val
385                 390                 395                 400

Val Ser Ala Asn Gly Glu Pro Thr Val Lys Leu Tyr Thr Ser Val Glu
                405                 410                 415

Asn Ala Gln Gln Asp Lys Gly Val Ala Ile Pro His Asp Ile Asp Leu
            420                 425                 430

Gly Asp Ser Arg Val Val Ile Gln Asp Tyr Asp Asn Gln His Glu Gln
            435                 440                 445

Asp Arg Pro Thr Pro Ser Pro Ala Pro Ser Arg Pro Phe Ser Val Leu
450                 455                 460

Arg Ala Asn Asp Val Leu Trp Leu Ser Leu Thr Ala Ala Glu Tyr Asp
465                 470                 475                 480

Gln Ser Thr Tyr Gly Ser Ser Thr Gly Pro Val Tyr Ile Ser Asp Ser
                485                 490                 495

Val Thr Leu Val Asn Val Ala Thr Gly Ala Gln Ala Val Ala Arg Ser
            500                 505                 510

Leu Asp Trp Ser Lys Val Thr Leu Asp Gly Arg Pro Leu Pro Thr Val
            515                 520                 525

Glu Gln Tyr Ser Lys Thr Phe Phe Val Leu Pro Leu Arg Gly Lys Leu
            530                 535                 540

Ser Phe Trp Glu Ala Gly Thr Thr Lys Ala Gly Tyr Pro Tyr Asn Tyr
545                 550                 555                 560

Asn Thr Thr Ala Ser Asp Gln Ile Leu Ile Glu Asn Ala Ala Gly His
                565                 570                 575

Arg Val Ala Ile Ser Thr Tyr Thr Arg Leu Gly Ala Gly Pro Val
            580                 585                 590

Ala Ile Ser Ala Ala Ala Val Leu Ala Pro Arg Ser Ala Leu Ala Leu
            595                 600                 605

Leu Glu Asp Thr Phe Asp Tyr Pro Gly Arg Ala His Thr Phe Asp Asp
```

```
                  610                 615                 620
Phe Cys Pro Glu Cys Arg Ala Leu Gly Leu Gln Gly Cys Ala Phe Gln
625                 630                 635                 640

Ser Thr Val Ala Glu Leu Gln Arg Leu Lys Val Lys Val Gly Lys Thr
                645                 650                 655

Arg Glu Leu (2) INFORMATION FOR SEQ ID NO:15:

(i) SEQUENCE CHARACTERISTICS:
        (A) LENGTH: 549 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (C) INDIVIDUAL ISOLATE: Hepatitis E virus (Burma strain)
             r62kDa, FIGURE 4

(xi) SEQUENCE DESCRIPTION: SEQ ID NO:15:

Ala Val Ala Pro Ala His Asp Thr Pro Pro Val Pro Asp Val Asp Ser
1               5                  10                  15

Arg Gly Ala Ile Leu Arg Arg Gln Tyr Asn Leu Ser Thr Ser Pro Leu
                20                  25                  30

Thr Ser Ser Val Ala Thr Gly Thr Asn Leu Val Leu Tyr Ala Ala Pro
            35                  40                  45

Leu Ser Pro Leu Leu Pro Leu Gln Asp Gly Thr Asn Thr His Ile Met
50                  55                  60

Ala Thr Glu Ala Ser Asn Tyr Ala Gln Tyr Arg Val Ala Arg Ala Thr
65                  70                  75                  80

Ile Arg Tyr Arg Pro Leu Val Pro Asn Ala Val Gly Gly Tyr Ala Ile
                85                  90                  95

Ser Ile Ser Phe Trp Pro Gln Thr Thr Thr Thr Pro Thr Ser Val Asp
            100                 105                 110

Met Asn Ser Ile Thr Ser Thr Asp Val Arg Ile Leu Val Gln Pro Gly
        115                 120                 125

Ile Ala Ser Glu Leu Val Ile Pro Ser Glu Arg Leu His Tyr Arg Asn
130                 135                 140

Gln Gly Trp Arg Ser Val Glu Thr Ser Gly Val Ala Glu Glu Glu Ala
145                 150                 155                 160

Thr Ser Gly Leu Val Met Leu Cys Ile His Gly Ser Leu Val Asn Ser
                165                 170                 175

Tyr Thr Asn Thr Pro Tyr Thr Gly Ala Leu Gly Leu Leu Asp Phe Ala
            180                 185                 190

Leu Glu Leu Glu Phe Arg Asn Leu Thr Pro Gly Asn Thr Asn Thr Arg
        195                 200                 205

Val Ser Arg Tyr Ser Ser Thr Ala Arg His Arg Leu Arg Arg Gly Ala
    210                 215                 220

Asp Gly Thr Ala Glu Leu Thr Thr Thr Ala Ala Thr Arg Phe Met Lys
225                 230                 235                 240

Asp Leu Tyr Phe Thr Ser Thr Asn Gly Val Gly Glu Ile Gly Arg Gly
                245                 250                 255

Ile Ala Leu Thr Leu Phe Asn Leu Ala Asp Thr Leu Leu Gly Gly Leu
            260                 265                 270
```

```
Pro Thr Glu Leu Ile Ser Ser Ala Gly Gly Gln Leu Phe Tyr Ser Arg
            275                 280                 285
Pro Val Val Ser Ala Asn Gly Glu Pro Thr Val Lys Leu Tyr Thr Ser
        290                 295                 300
Val Glu Asn Ala Gln Gln Asp Lys Gly Ile Ala Ile Pro His Asp Ile
305                 310                 315                 320
Asp Leu Gly Glu Ser Arg Val Val Ile Gln Asp Tyr Asp Asn Gln His
                325                 330                 335
Glu Gln Asp Arg Pro Thr Pro Ser Pro Ala Pro Ser Arg Pro Phe Ser
            340                 345                 350
Val Leu Arg Ala Asn Asp Val Leu Trp Leu Ser Leu Thr Ala Ala Glu
        355                 360                 365
Tyr Asp Gln Ser Thr Tyr Gly Ser Ser Thr Gly Pro Val Tyr Val Ser
    370                 375                 380
Asp Ser Val Thr Leu Val Asn Val Ala Thr Gly Ala Gln Ala Val Ala
385                 390                 395                 400
Arg Ser Leu Asp Trp Thr Lys Val Thr Leu Asp Gly Arg Pro Leu Ser
                405                 410                 415
Thr Ile Gln Gln Tyr Ser Lys Thr Phe Phe Val Leu Pro Leu Arg Gly
            420                 425                 430
Lys Leu Ser Phe Trp Glu Ala Gly Thr Thr Lys Ala Gly Tyr Pro Tyr
        435                 440                 445
Asn Tyr Asn Thr Thr Ala Ser Asp Gln Leu Leu Val Glu Asn Ala Ala
    450                 455                 460
Gly His Arg Val Ala Ile Ser Thr Tyr Thr Thr Ser Leu Gly Ala Gly
465                 470                 475                 480
Pro Val Ser Ile Ser Ala Val Ala Val Leu Ala Pro His Ser Ala Leu
                485                 490                 495
Ala Leu Leu Glu Asp Thr Leu Asp Tyr Pro Ala Arg Ala His Thr Phe
            500                 505                 510
Asp Asp Phe Cys Pro Glu Cys Arg Pro Leu Gly Leu Gln Gly Cys Ala
        515                 520                 525
Phe Gln Ser Thr Val Ala Glu Leu Gln Arg Leu Lys Met Lys Val Gly
    530                 535                 540
Lys Thr Arg Glu Leu
545

(2) INFORMATION FOR SEQ ID NO:16:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E virus (Mexico strain)
            r62kDa, FIGURE 4

(xi) SEQUENCE DESCRIPTION: SEQ ID NO:16:

Ala Val Ala Pro Ala His Asp Thr Ser Pro Val Pro Asp Val Asp Ser
1               5                   10                  15
Arg Gly Ala Ile Leu Arg Arg Gln Tyr Asn Leu Ser Thr Ser Pro Leu
            20                  25                  30
```

-continued

```
Thr Ser Ser Val Ala Ser Gly Thr Asn Leu Val Leu Tyr Ala Ala Pro
         35                  40                  45

Leu Asn Pro Pro Leu Pro Leu Gln Asp Gly Thr Asn Thr His Ile Met
 50                  55                  60

Ala Thr Glu Ala Ser Asn Tyr Ala Gln Tyr Arg Val Ala Arg Ala Thr
 65                  70                  75                  80

Ile Arg Tyr Arg Pro Leu Val Pro Asn Ala Val Gly Tyr Ala Ile
                 85                  90                  95

Ser Ile Ser Phe Trp Pro Gln Thr Thr Thr Pro Thr Ser Val Asp
                100                 105                 110

Met Asn Ser Ile Thr Ser Thr Asp Val Arg Ile Leu Val Gln Pro Gly
        115                 120                 125

Ile Ala Ser Glu Leu Val Ile Pro Ser Glu Arg Leu His Tyr Arg Asn
130                 135                 140

Gln Gly Trp Arg Ser Val Glu Thr Ser Gly Val Ala Glu Glu Glu Ala
145                 150                 155                 160

Thr Ser Gly Leu Val Met Leu Cys Ile His Gly Ser Pro Val Asn Ser
                165                 170                 175

Tyr Thr Asn Thr Pro Tyr Thr Gly Ala Leu Gly Leu Leu Asp Phe Ala
                180                 185                 190

Leu Glu Leu Glu Phe Arg Asn Leu Thr Thr Cys Asn Thr Asn Thr Arg
            195                 200                 205

Val Ser Arg Tyr Ser Ser Thr Ala Arg His Ser Ala Arg Gly Ala Asp
        210                 215                 220

Gly Thr Ala Glu Leu Thr Thr Thr Ala Ala Thr Arg Phe Met Lys Asp
225                 230                 235                 240

Leu His Phe Thr Gly Leu Asn Gly Val Gly Glu Val Gly Arg Gly Ile
                245                 250                 255

Ala Leu Thr Leu Leu Asn Leu Ala Asp Thr Leu Leu Gly Gly Leu Pro
                260                 265                 270

Thr Glu Leu Ile Ser Ser Ala Gly Gly Gln Leu Phe Tyr Ser Arg Pro
            275                 280                 285

Val Val Ser Ala Asn Gly Glu Pro Thr Val Lys Leu Tyr Thr Ser Val
        290                 295                 300

Glu Asn Ala Gln Gln Asp Lys Gly Val Ala Ile Pro His Asp Ile Asp
305                 310                 315                 320

Leu Gly Asp Ser Arg Val Val Ile Gln Asp Tyr Asp Asn Gln His Glu
                325                 330                 335

Gln Asp Arg Pro Thr Pro Ser Pro Ala Pro Ser Arg Pro Phe Ser Val
            340                 345                 350

Leu Arg Ala Asn Asp Val Leu Trp Leu Ser Leu Thr Ala Ala Glu Tyr
        355                 360                 365

Asp Gln Ser Thr Tyr Gly Ser Ser Thr Gly Pro Val Tyr Ile Ser Asp
        370                 375                 380

Ser Val Thr Leu Val Asn Val Ala Thr Gly Ala Gln Ala Val Ala Arg
385                 390                 395                 400

Ser Leu Asp Trp Ser Lys Val Thr Leu Asp Gly Arg Pro Leu Pro Thr
                405                 410                 415

Val Glu Gln Tyr Ser Lys Thr Phe Phe Val Leu Pro Leu Arg Gly Lys
            420                 425                 430

Leu Ser Phe Trp Glu Ala Gly Thr Thr Lys Ala Gly Tyr Pro Tyr Asn
        435                 440                 445
```

```
Tyr Asn Thr Thr Ala Ser Asp Gln Ile Leu Ile Glu Asn Ala Ala Gly
    450                 455                 460

His Arg Val Ala Ile Ser Thr Tyr Thr Thr Arg Leu Gly Ala Gly Pro
465                 470                 475                 480

Val Ala Ile Ser Ala Ala Val Leu Ala Pro Arg Ser Ala Leu Ala
                485                 490                 495

Leu Leu Glu Asp Thr Phe Asp Tyr Pro Gly Arg Ala His Thr Phe Asp
            500                 505                 510

Asp Phe Cys Pro Glu Cys Arg Ala Leu Gly Leu Gln Gly Cys Ala Phe
            515                 520                 525

Gln Ser Thr Val Ala Glu Leu Gln Arg Leu Lys Val Lys Val Gly Lys
            530                 535                 540

Thr Arg Glu Leu
545

(2) INFORMATION FOR SEQ ID NO:17:

(i) SEQUENCE CHARACTERISTICS:
        (A) LENGTH: 327 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Burma strain) SG3

-continued

```
    210                 215                 220

Pro Tyr Asn Tyr Asn Thr Thr Ala Ser Asp Gln Leu Leu Val Glu Asn
225                 230                 235                 240

Ala Ala Gly His Arg Val Ala Ile Ser Thr Tyr Thr Thr Ser Leu Gly
                245                 250                 255

Ala Gly Pro Val Ser Ile Ser Ala Val Ala Val Leu Ala Pro His Ser
            260                 265                 270

Ala Leu Ala Leu Leu Glu Asp Thr Leu Asp Tyr Pro Ala Arg Ala His
        275                 280                 285

Thr Phe Asp Asp Phe Cys Pro Glu Cys Arg Pro Leu Gly Leu Gln Gly
    290                 295                 300

Cys Ala Phe Gln Ser Thr Val Ala Glu Leu Gln Arg Leu Lys Met Lys
305                 310                 315                 320

Val Gly Lys Thr Arg Glu Leu
                325
```

(2) INFORMATION FOR SEQ ID NO:18:

(i) SEQUENCE CHARACTERISTICS:
(A) LENGTH: 327 amino acids
(B) TYPE: amino acid
(D) TOPOLOGY: linear (ii) MOLECULE TYPE: protein (iii) HYPOTHETICAL: NO (vi) ORIGINAL SOURCE:
(C) INDIVIDUAL ISOLATE: Hepatitis E Virus (Mexico strain) SG3 region (xi) SEQUENCE DESCRIPTION: SEQ ID NO:18:

```
Gly Ala Asp Gly Thr Ala Glu Leu Thr Thr Thr Ala Ala Thr Arg Phe
1               5                   10                  15

Met Lys Asp Leu His Phe Thr Gly Leu Asn Gly Val Gly Glu Val Gly
            20                  25                  30

Arg Gly Ile Ala Leu Thr Leu Leu Asn Leu Ala Asp Thr Leu Leu Gly
        35                  40                  45

Gly Leu Pro Thr Glu Leu Ile Ser Ser Ala Gly Gly Gln Leu Phe Tyr
    50                  55                  60

Ser Arg Pro Val Val Ser Ala Asn Gly Glu Pro Thr Val Lys Leu Tyr
65                  70                  75                  80

Thr Ser Val Glu Asn Ala Gln Gln Asp Lys Gly Val Ala Ile Pro His
                85                  90                  95

Asp Ile Asp Leu Gly Asp Ser Arg Val Val Ile Gln Asp Tyr Asp Asn
            100                 105                 110

Gln His Glu Gln Asp Arg Pro Thr Pro Ser Pro Ala Pro Ser Arg Pro
        115                 120                 125

Phe Ser Val Leu Arg Ala Asn Asp Val Leu Trp Leu Ser Leu Thr Ala
    130                 135                 140

Ala Glu Tyr Asp Gln Ser Thr Tyr Gly Ser Ser Thr Gly Pro Val Tyr
145                 150                 155                 160

Ile Ser Asp Ser Val Thr Leu Val Asn Val Ala Thr Gly Ala Gln Ala
                165                 170                 175

Val Ala Arg Ser Leu Asp Trp Ser Lys Val Thr Leu Asp Gly Arg Pro
            180                 185                 190

Leu Pro Thr Val Glu Gln Tyr Ser Lys Thr Phe Phe Val Leu Pro Leu
        195                 200                 205

```
Arg Gly Lys Leu Ser Phe Trp Glu Ala Gly Thr Thr Lys Ala Gly Tyr
    210                 215                 220

Pro Tyr Asn Tyr Asn Thr Thr Ala Ser Asp Gln Ile Leu Ile Glu Asn
225                 230                 235                 240

Ala Ala Gly His Arg Val Ala Ile Ser Thr Tyr Thr Thr Arg Leu Gly
                245                 250                 255

Ala Gly Pro Val Ala Ile Ser Ala Ala Ala Val Leu Ala Pro Arg Ser
            260                 265                 270

Ala Leu Ala Leu Leu Glu Asp Thr Phe Asp Tyr Pro Gly Arg Ala His
        275                 280                 285

Thr Phe Asp Asp Phe Cys Pro Glu Cys Arg Ala Leu Gly Leu Gln Gly
    290                 295                 300

Cys Ala Phe Gln Ser Thr Val Ala Glu Leu Gln Arg Leu Lys Val Lys
305                 310                 315                 320

Val Gly Lys Thr Arg Glu Leu
            325
```

(2) INFORMATION FOR SEQ ID NO:19:

(i) SEQUENCE CHARACTERISTICS:
        (A) LENGTH: 33 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Burma strain)
        406.4-2

(xi) SEQUENCE DESCRIPTION: SEQ ID NO:19:

```
Ala Asn Pro Pro Asp His Ser Ala Pro Leu Gly Val Thr Arg Pro Ser
1               5                   10                  15

Ala Pro Pro Leu Pro His Val Val Asp Leu Pro Gln Leu Gly Pro Arg
            20                  25                  30

Arg
```

(2) INFORMATION FOR SEQ ID NO:20:

(i) SEQUENCE CHARACTERISTICS:
(A) LENGTH: 33 amino acids
(B) TYPE: amino acid
(D) TOPOLOGY: linear (ii) MOLECULE TYPE: protein (iii) HYPOTHETICAL: NO (vi) ORIGINAL SOURCE:
(C) INDIVIDUAL ISOLATE: Hepatitis E Virus (Mexico strain) 406.4-2

(xi) SEQUENCE DESCRIPTION: SEQ ID NO:20:

```
Ala Asn Gln Pro Gly His Leu Ala Pro Leu Gly Glu Ile Arg Pro Ser
1               5                   10                  15

Ala Pro Pro Leu Pro Pro Val Ala Asp Leu Pro Gln Pro Gly Leu Arg
            20                  25                  30

Arg
```

(2) INFORMATION FOR SEQ ID NO:21:

```
    (i) SEQUENCE CHARACTERISTICS:
        (A) LENGTH: 124 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Burma Strain)
            ORF-3

(xi) SEQUENCE DESCRIPTION: SEQ ID NO:21:

Met Asn Asn Met Ser Phe Ala Ala Pro Met Gly Ser Arg Pro Cys Ala
1               5                   10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
            35                  40                  45

Ala Val Pro Ala Val Val Ser Gly Val Thr Gly Leu Ile Leu Ser Pro
        50                  55                  60

Ser Gln Ser Pro Ile Phe Ile Gln Pro Thr Pro Ser Pro Pro Met Ser
65                  70                  75                  80

Pro Leu Arg Pro Gly Leu Asp Leu Val Phe Ala Asn Pro Pro Asp His
                85                  90                  95

Ser Ala Pro Leu Gly Val Thr Arg Pro Ser Ala Pro Leu Pro His
            100                 105                 110

Val Val Asp Leu Pro Gln Leu Gly Pro Arg Arg Glx
        115                 120

(2) INFORMATION FOR SEQ ID NO:22:

(i) SEQUENCE CHARACTERISTICS:
        (A) LENGTH: 124 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Mexico Strain)
            ORF-3

(xi) SEQUENCE DESCRIPTION: SEQ ID NO:22:

Met Asn Asn Met Trp Phe Ala Ala Pro Met Gly Ser Pro Pro Cys Ala
1               5                   10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
            35                  40                  45

Ala Val Pro Ala Val Val Ser Gly Val Thr Gly Leu Ile Leu Ser Pro
        50                  55                  60

Ser Gln Ser Pro Ile Phe Ile Gln Pro Thr Pro Leu Pro Gln Thr Leu
65                  70                  75                  80

Pro Leu Arg Pro Gly Leu Asp Leu Ala Phe Ala Asn Gln Pro Gly His
                85                  90                  95

Leu Ala Pro Leu Gly Glu Ile Arg Pro Ser Ala Pro Pro Leu Pro Pro
            100                 105                 110
```

```
Val Ala Asp Leu Pro Gln Pro Gly Leu Arg Arg Glx
        115                 120
```

(2) INFORMATION FOR SEQ ID NO:23:

(i) SEQUENCE CHARACTERISTICS:
        (A) LENGTH: 48 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Burma strain)
            406.3-2

(xi) SEQUENCE DESCRIPTION: SEQ ID NO:23:

```
Thr Leu Asp Tyr Pro Ala Arg Ala His Thr Phe Asp Asp Phe Cys Pro
1               5                   10                  15

Glu Cys Arg Pro Leu Gly Leu Gln Gly Cys Ala Phe Gln Ser Thr Val
            20                  25                  30

Ala Glu Leu Gln Arg Leu Lys Met Lys Val Gly Lys Thr Arg Glu Leu
            35                  40                  45
```

(2) INFORMATION FOR SEQ ID NO:24:

(i) SEQUENCE CHARACTERISTICS:
        (A) LENGTH: 48 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: Hepatitis E Virus (Mexico strain)
            406.3-2 region (xi) SEQUENCE DESCRIPTION: SEQ ID NO:24:

```
Thr Phe Asp Tyr Pro Gly Arg Ala His Thr Phe Asp Asp Phe Cys Pro
1               5                   10                  15

Glu Cys Arg Ala Leu Gly Leu Gln Gly Cys Ala Phe Gln Ser Thr Val
            20                  25                  30

Ala Glu Leu Gln Arg Leu Lys Val Lys Val Gly Lys Thr Arg Glu Leu
            35                  40                  45
```